US009649185B2

(12) United States Patent
Bangera et al.

(10) Patent No.: US 9,649,185 B2
(45) Date of Patent: May 16, 2017

(54) ADJUNCTS FOR GASTROINTESTINAL DEVICES

(71) Applicant: Elwha LLC, Bellevue, WA (US)

(72) Inventors: Mahalaxmi Gita Bangera, Renton, WA (US); William David Duncan, Mill Creek, WA (US); Roderick A. Hyde, Redmond, WA (US); Wayne R. Kindsvogel, Seattle, WA (US); Elizabeth A. Sweeney, Seattle, WA (US)

(73) Assignee: Elwha LLC, Bellevue, WA (US)

( * ) Notice: Subject to any disclaimer, the term of this patent is extended or adjusted under 35 U.S.C. 154(b) by 99 days.

(21) Appl. No.: 14/533,400

(22) Filed: Nov. 5, 2014

(65) Prior Publication Data

US 2016/0058543 A1    Mar. 3, 2016

Related U.S. Application Data

(63) Continuation-in-part of application No. 14/471,169, filed on Aug. 28, 2014, and a continuation-in-part of application No. 14/471,224, filed on Aug. 28, 2014.

(51) Int. Cl.

| A61M 5/00 | (2006.01) |
|---|---|
| A61F 2/04 | (2013.01) |
| A61L 29/16 | (2006.01) |
| A61L 29/14 | (2006.01) |
| A61K 45/06 | (2006.01) |
| A61K 9/00 | (2006.01) |
| A61F 5/00 | (2006.01) |

(Continued)

(52) U.S. Cl.
CPC .............. *A61F 2/04* (2013.01); *A61F 5/0036* (2013.01); *A61F 5/0076* (2013.01); *A61K 9/0092* (2013.01); *A61K 9/7023* (2013.01); *A61K 35/74* (2013.01); *A61K 45/06* (2013.01); *A61K 47/34* (2013.01); *A61L 29/148* (2013.01); *A61L 29/16* (2013.01); *A61F 2/82* (2013.01); *A61F 2002/045* (2013.01); *A61F 2210/0004* (2013.01); *A61F 2210/0076* (2013.01); *A61F 2220/0016* (2013.01); *A61F 2240/001* (2013.01); *A61L 2300/30* (2013.01); *A61L 2300/64* (2013.01)

(58) Field of Classification Search
CPC ..... A61F 5/0076; A61F 5/0036; A61K 35/74; A61L 29/16
USPC .......................................................... 604/8
See application file for complete search history.

(56) References Cited

U.S. PATENT DOCUMENTS

| 3,331,772 A | 7/1967 | Brownscombe et al. |
|---|---|---|
| 5,275,766 A | 1/1994 | Gadkaree et al. |

(Continued)

OTHER PUBLICATIONS

Allegretti et al.; "Restoring the gut microbiome for the treatment of inflammatory bowel diseases"; World Journal of Gastroenterology; Apr. 7, 2014; pp. 3468-3474; vol. 20, Issue 13; Baishideng Publishing Group Co.

(Continued)

*Primary Examiner* — Leslie Deak

(57) ABSTRACT

An adjunct for a gastrointestinal device and a system including said adjunct are described herein and include a substrate configured to attach to a gastrointestinal device, the substrate including a first surface and a second surface, and a plurality of at least one type of commensal microbe associated with at least a portion of at least one of the first surface and the second surface of the substrate.

34 Claims, 19 Drawing Sheets

(51) Int. Cl.
| | |
|---|---|
| *A61K 9/70* | (2006.01) |
| *A61K 35/74* | (2015.01) |
| *A61K 47/34* | (2017.01) |
| *A61F 2/82* | (2013.01) |

(56) References Cited

U.S. PATENT DOCUMENTS

| | | | |
|---|---|---|---|
| 5,662,713 | A | 9/1997 | Andersen et al. |
| 7,025,791 | B2 | 4/2006 | Levine et al. |
| 7,037,344 | B2 | 5/2006 | Kagan et al. |
| 7,101,565 | B2 | 9/2006 | Monte |
| 7,976,488 | B2 | 7/2011 | Levine et al. |
| 7,998,060 | B2 | 8/2011 | Ferren et al. |
| 8,282,561 | B2 | 10/2012 | Towe |
| 8,753,387 | B2 | 6/2014 | Headley et al. |
| 8,753,407 | B2 | 6/2014 | Nguyen |
| 2005/0049718 | A1 | 3/2005 | Dann et al. |
| 2008/0060995 | A1 | 3/2008 | Zhang et al. |
| 2011/0021888 | A1 | 1/2011 | Sing et al. |
| 2012/0158026 | A1 | 6/2012 | Behan |
| 2012/0184893 | A1 | 7/2012 | Thompson et al. |
| 2012/0232460 | A1* | 9/2012 | Raven ............... A61B 5/0031 604/9 |
| 2013/0030351 | A1 | 1/2013 | Belhe et al. |
| 2013/0131765 | A1 | 5/2013 | Polkinghorne et al. |
| 2013/0281911 | A1 | 10/2013 | Babkes et al. |
| 2013/0331759 | A1 | 12/2013 | Neisz et al. |
| 2014/0012178 | A1 | 1/2014 | Chin |
| 2014/0200502 | A1 | 7/2014 | Belhe et al. |
| 2015/0265660 | A1* | 9/2015 | Kaznessis ............ A01N 63/00 424/93.4 |

OTHER PUBLICATIONS

Andersson et al.; "Comparative Analysis of Human Gut Microbiota by Barcoded Pyrosequencing"; Plos One; Jul. 2008; pp. 1-8; vol. 3, Issue 7.
Bakken et al.; "Treating Clostridium difficile Infection with Fecal Microbiota Transplantation"; National Institutes of Health Public Access; Dec. 2011; pp. 1-13; vol. 9, Issue 12; Elsevier Inc.
Baxter et al.; "Structure of the gut microbiome following colonization with human feces determines colonic tumor burden"; Microbiome; bearing a date of Mar. 5, 2014; pp. 1-11; vol. 2, Issue 20; BioMed Central Ltd.
Borody et al.; "Fecal Microbiota Transplantation: Indications, Methods, Evidence, and Future Directions"; Curr Gastroenterol Rep; Accessed on Jun. 23, 2014; pp. 1-7; vol. 15, Issue 337.
Cox et al.; "Pathways in Microbe-Induced Obesity"; National Institutes of Health Public Access; Jun. 4, 2013; pp. 1-21; vol. 17, Issue 6; Elsevier Inc.
Damaskos et al.; "Probiotics and prebiotics in inflammatory bowel disease: microflora 'on the scope'"; British Journal of Clinical Pharmacology; bearing a date of Sep. 11, 2007; pp. 453-467; vol. 65, Issue 4; Blackwell Publishing Ltd.
Derrien et al.; "Mucin-bacterial interactions in the human oral cavity and digestive tract"; Gut Microbes; Jul./Aug. 2010; pp. 254-268; vol. 1, Issue 4; Landes Bioscience.
Di Bella et al.; "Fecal microbiota transplantation: the state of the art"; Infectious Disease Reports 2013; bearing a date of Jun. 4, 2013; pp. 43-45; vol. 5, Issue e13.
Escalona et al.; "Weight Loss and Metabolic Improvement in Morbidly Obese Subjects Implanted for 1 Year With an Endoscopic Duodenal-Jejunal Bypass Liner"; Annals of Surgery; Jun. 2012; pp. 1080-1085; vol. 255, Issue 6; Lippincott Williams & Wilkins.
Espinet-Coll et al.; "Current endoscopic techniques in the treatment of obesity"; Revista Española De Enfermedades Digestivas; Accessed on Aug. 8, 2014; pp. 72-87; vol. 104, Issue 2; Arán Ediciones, S.L.
Fan et al.; Structures in *Bacillus subtilis* are Recognized by CD14 in a Lipopolysaccharide Binding Protein-Dependent Reaction; Infection and Immunity; Jun. 1999; pp. 2964-2968; vol. 64, Issue 6; American Society for Microbiology.
Fujii et al.; "Culturing intestinal stem cells: applications for colorectal cancer research"; Frontiers in Genetics; Jun. 5, 2014; pp. 1-5; vol. 5, Article 169.
Gauglitz et al.; "Host Defence Against *Candida albicans* and the Role of Pattern-recognition Receptors"; Acta Derm Venereol; bearing a date of Aug. 15, 2011; pp. 291-300; vol. 92; Acta Dermato-Venereologica.
Gomes et al.; "Natural and Genetically Engineered Proteins for Tissue Engineering"; National Institutes of Health Public Access; bearing a date of Jan. 1, 2012; pp. 1-32; vol. 37, Issue 1; Elsevier Ltd.
Grover et al.; "Probiotics for human health—new innovations and emerging trends"; Gut Pathogens; bearing a date of Nov. 13, 2012; pp. 1-14; vol. 4, Issue 15; BioMed Central Ltd.
Hamilton et al.; "High-thoughput DNA sequence analysis reveals stable engraftment of gut microbiota following transplantation of previously frozen fecal bacteria"; Gut Microbes; Mar./Apr. 2013; pp. 125-135; vol. 4, Issue 2; Landes Bioscience.
Hardy et al.; "Probiotics, Prebiotics and Immunomodulation of Gut Mucosal Defences: Homeostasis and Immunopathology"; Nutrients 2013; bearing a date of Mar. 5, 2013; pp. 1869-1912.
Harley et al.; "Obesity and the gut microbiome: Striving for causality"; Molecular Metabolism; bearing a date of Jun. 10, 2012; pp. 21-31; vol. 1; Elsevier GmbH.
Hoffman et al.; "Archaea and Fungi of the Human Gut Microbiome: Correlations with Diet and Bacterial Residents"; PLOS One; Jun. 2013; pp. 1-12; vol. 8, Issue 6.
Kadooka et al.; "Regulation of abdominal adiposity by probiotics (*Lactobacillus gasseri* SBT2055) in adults with obese tendencies in a randomized controlled trial"; European Journal of Clinical Nutrition; bearing a date of Aug. 14, 2009; pp. 636-643; vol. 64; Macmillan Publishers Limited.
Kong et al.; "Controlling Rigidity and Degradation of Alginate Hydrogels via Molecular Weight Distribution"; Biomacromolecules; bearing a date of Feb. 25, 2004; pp. 1720-1727; vol. 5; American Chemical Society.
Kubinak et al.; "Toll-Like Receptors Promote Mutually Beneficial Commensal-Host Interactions"; PLOS Pathogens; Jul. 2012; pp. 1-3; vol. 8, Issue 7.
Kumar et al.; "AnimalLectinDb: An integrated animal lectin database"; Bioinformation—Discovery at the interface of physical and biological sciences; bearing a date of Feb. 25, 2011; pp. 134-136; vol. 6, Issue 3; Biomedical Informatics.
Lawley et al.; "Targeted Restoration of the Intestinal Microbiota with a Simple, Defined Bacteriotherapy Resolves Relapsing *Clostridium difficile* Disease in Mice"; PLOS Pathogens; Oct. 2012; pp. 1-14; vol. 8, Issue 10.
Lieleg et al.; "Biological Hydrogels as Selective Diffusion Barriers"; National Institutes of Health Public Access; Trends Cell Biol.; bearing a date of Sep. 2011; pp. 1-19; vol. 21, Issue 9.
Lin et al.; "Hydrogels in controlled release formulations: Network design and mathematical modeling"; Science Direct—Advanced Drug Delivery Reviews; bearing a date of Aug. 15, 2006; pp. 1379-1408; Elsevier B.V.
Lotfipour et al.; "Evaluation of the effect of $CaCl_2$ and alginate concentrations and hardening time on the characteristics of *Lactobacillus acidophilus* loaded alginate beads using response surface analysis"; Advanced Pharmaceutical Bulletin; bearing a date of Feb. 10, 2012; pp. 71-78; vol. 2, Issue 1; Tabriz University of Medical Sciences.
Makadia et al.; "Poly Lactic-co-Glycolic Acid (PLGA) as Biodegradable Controlled Drug Delivery Carrier"; Polymers; bearing a date of Aug. 26, 2011; pp. 1377-1397; vol. 3.
Marzorati et al.; The HMI™ module: a new tool to study the Host-Microbiota Interaction in the human gastrointestinal tract in vitro; BMC Microbiology Methodology Article; bearing a date of May 22, 2014; pp. 1-14; vol. 14, Issue 133; BioMed Central Ltd.
Mattar et al.; "Probiotics up-regulate MUC-2 mucin gene expression in a Caco-2 cell-culture model"; Pediatr Surg. Int; bearing a date of Sep. 21, 2002; pp. 586-590; Springer-Verlag.

(56) References Cited

OTHER PUBLICATIONS

Maynard et al.; "Reciprocal interactions of the intestinal microbiota and immune system"; Nature; Sep. 13, 2012; pp. 231-241; vol. 489.
Miyata et al.; "Tumor marker-responsive behavior of gels prepared by biomolecular imprinting"; PNAS; Jan. 31, 2006; pp. 1190-1193; vol. 103, Issue 5; The National Academy of Sciences of the USA.
Modlin et al.; "Innate Immunity: Ignored for decades, but not forgotten"; National Institutes of Health Public Access; J. Invest Dermatol; bearing a date of Mar. 2012; vol. 132, Issue 3; pp. 1-9.
Moreno-Indias et al.; "Impact of the gut microbiota on the development of obesity and type 2 diabetes mellitus"; Frontiers in Microbiology; Apr. 2014; pp. 1-10; vol. 5, Issue 190.
Morowitz et al.; "Contributions of Intestinal Bacteria to Nutrition and Metabolism in the Critically Ill"; National Institutes of Health Public Access; Surg Clin North Am.; bearing a date of Aug. 2011; pp. 1-15; vol. 91, Issue 4; Elsevier Inc.
Neumann et al.; "Differences in signalling by directly and indirectly binding ligands in bacterial chemotaxis"; The Embo Journal; bearing a date of Sep. 10, 2010; pp. 3484-3495; vol. 29, Issue 20; European Molecular Biology Organization.
Ouwehand et al.; "[13] Microbial Interactions to Intestinal Mucosal Models"; Methods in Enzymology; accessed on Aug. 8, 2014; pp. 200-212; vol. 337; Academic Press.
"Polyethylene-co-vinyl acetate 70:30 (wt) MW 55,000"; located at http://www.polysciences.com/Catalog/Department/Product/98/categoryid--286/productid--3186/search--polyethylene-co-vinyl/; Polysciences Inc.; printed on Jul. 28, 2014; pp. 1-2.
Rohde et al.; "Effect of the EndoBarrier Gastrointestinal Liner on obesity and type 2 diabetes: protocol for systematic review and meta-analysis of clinical studies"; BMJ Open; downloaded Jun. 11, 2014; pp. 1-5; vol. 3; group.bmj.com.
Schmaljohann, Dirk; "Thermo- and pH-responsive polymers in drug delivery"; ScienceDirect—Advanced Drug Delivery Reviews; bearing a date of Oct. 18, 2006; pp. 1655-1670; vol. 58; Elsevier B.V.
Tilg et al.; "Gut microbiome, obesity, and metabolic dysfunction"; The Journal of Clinical Investigation; Jun. 2011; pp. 2126-2132; vol. 121, Issue 6.
Urgesi et al.; "A randomized double-blind placebo-controlled clinical trial on efficacy and safety of association of simethicone and *Bacillus coagulans* (Colinox®) in patients with irritable bowel syndrome"; European Review for Medical and Pharmacological Sciences; accessed on Jun. 23, 2014; pp. 1344-1353; vol. 18.
Van Boeckel et al.; "Fully covered self-expandable metal stents (SEMS), partially covered SEMS and self-expandable plastic stents for the treatment of benign esophageal ruptures and anastomotic leaks"; BMC Gastroenterology; accessed Jun. 23, 2014; pp. 1-7; vol. 12, Issue 19; BioMed Central Ltd.
Van Tassell et al.; "*Lactobacillus* Adhesion to Mucus"; Nutrients; bearing a date of May 20, 2011; pp. 613-636.
Vert et al.; "Terminology for biorelated polymers and applications (IUPAC Recommendations 2012)"; Pure Appl. Chem.; Jan. 11, 2012; pp. 377-410; vol. 84, Issue 2; IUPAC.
Wang et al.; "Upper gastrointestinal microbiota and digestive diseases"; World of Gastroenterology; Mar. 14, 2013; pp. 1541-1550; vol. 19, Issue 10; Baishindeng.
Wu et al.; "Analysis of the Human Gut Microbiome and Association With Disease"; Clinical Gastroenterology and Hepatology—Advances in Translational Science; accessed on Jun. 23, 2014; pp. 774-777.
Wu et al.; "The role of gut microbiota in immune homeostasis and autoimmunity"; Gut Microbes; Jan./Feb. 2012; pp. 4-14; vol. 3, Issue 1; Landes Bioscience.
Yang et al.; "Engineering Target-Responsive Hydrogels Based on Aptamer-Target Interactions"; J. Am. Chem. Soc.; Apr. 29, 2008; pp. 6320-6321; vol. 130, Issue 20; American Chemical Society.
Zoetendal et al.; "The human small intestinal microbiota is driven by rapid uptake and conversion of simple carbohydrates"; The ISME Journal; bearing a date of Jan. 19, 2012; pp. 1415-1426; vol. 6; International Society for Microbial Ecology.
PCT International Search Report; International App. No. PCT/US2015/046650; Dec. 1, 2015; pp. 1-3.

* cited by examiner

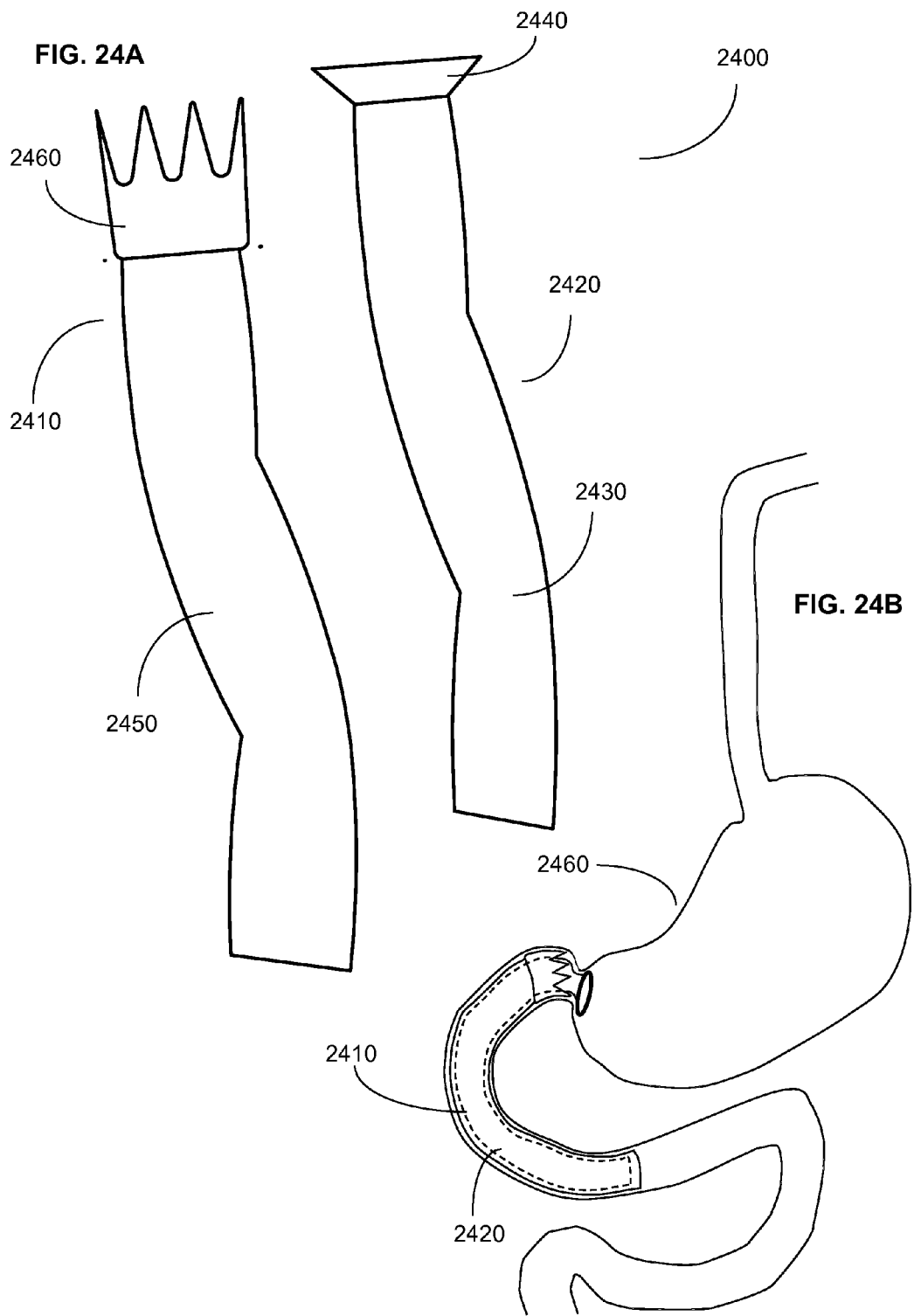

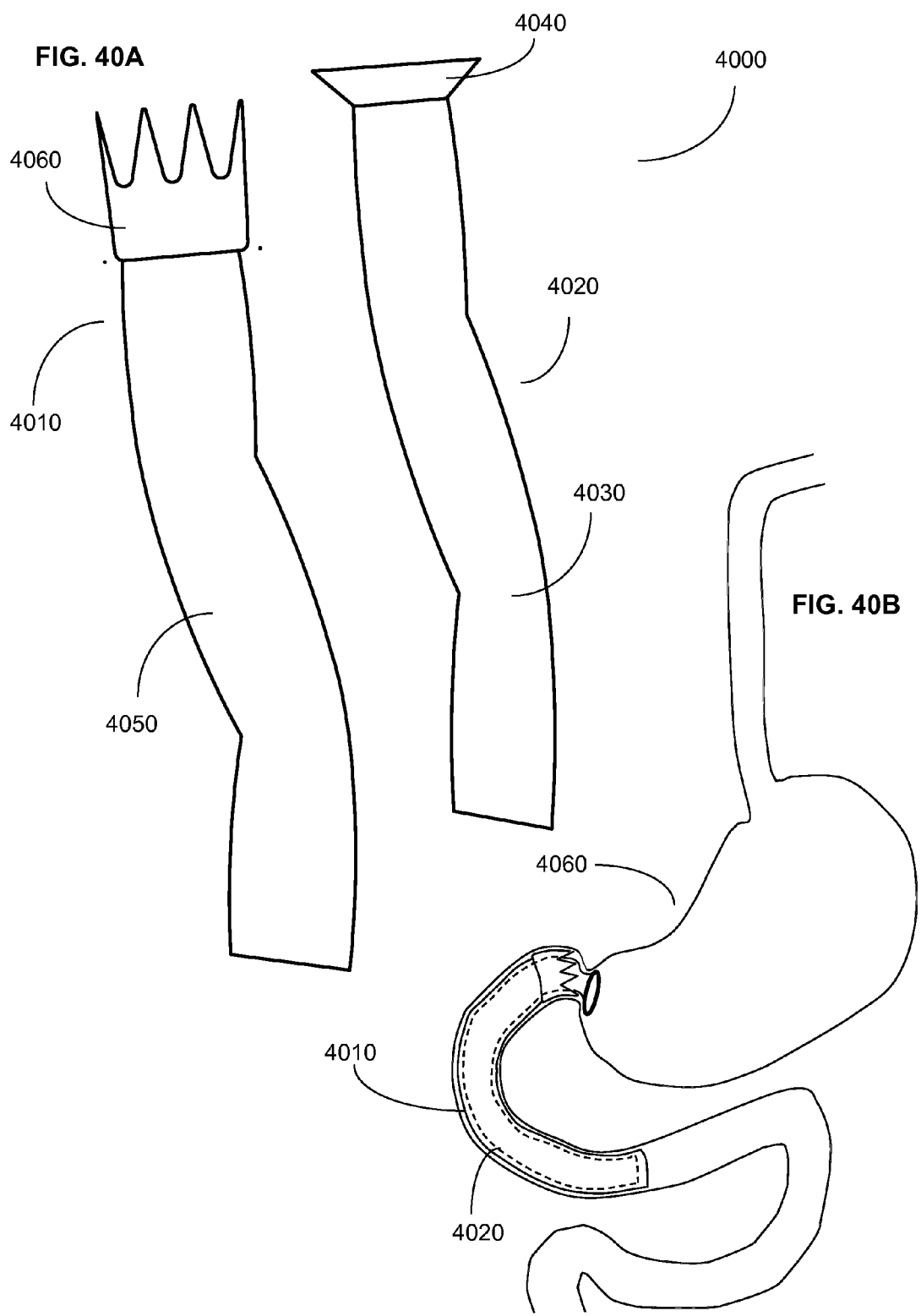

ADJUNCTS FOR GASTROINTESTINAL DEVICES

If an Application Data Sheet (ADS) has been filed on the filing date of this application, it is incorporated by reference herein. Any applications claimed on the ADS for priority under 35 U.S.C. §§119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 USC §119(e) for provisional patent applications, for any and all parent, grandparent, great-grandparent, etc. applications of the Priority application(s)).

PRIORITY APPLICATIONS

The present application constitutes a continuation-in-part of U.S. patent application Ser. No. 14/471,169, entitled GASTROINTESTINAL DEVICE WITH ASSOCIATED COMMENSAL MICROBES, naming Mahalaxmi G. Bangera, William D. Duncan, Roderick A. Hyde, Wayne R. Kindsvogel, and Elizabeth A. Sweeney as inventors, filed 28, Aug. 2014, which is currently co-pending or is an application of which a currently co-pending application is entitled to the benefit of the filing date.

The present application constitutes a continuation-in-part of U.S. patent application Ser. No. 14/471,224, entitled GASTROINTESTINAL DEVICE WITH ASSOCIATED MICROBE-PROMOTING AGENTS, naming Mahalaxmi G. Bangera, William D. Duncan, Roderick A. Hyde, Wayne R. Kindsvogel, and Elizabeth A. Sweeney as inventors, filed 28, Aug. 2014, which is currently co-pending or is an application of which a currently co-pending application is entitled to the benefit of the filing date.

If the listings of applications provided above are inconsistent with the listings provided via an ADS, it is the intent of the Applicant to claim priority to each application that appears in the Domestic Benefit/National Stage Information section of the ADS and to each application that appears in the Priority Applications section of this application.

All subject matter of the Priority Applications and of any and all applications related to the Priority Applications by priority claims (directly or indirectly), including any priority claims made and subject matter incorporated by reference therein as of the filing date of the instant application, is incorporated herein by reference to the extent such subject matter is not inconsistent herewith.

SUMMARY

In an aspect, an adjunct for a gastrointestinal device includes, but is not limited to, a substrate configured to attach to a gastrointestinal device, the substrate including a first surface and a second surface; and a plurality of at least one type of commensal microbe associated with at least a portion of at least one of the first surface and the second surface of the substrate. In addition to the foregoing, other aspects of a device are described in the claims, drawings, and text forming a part of the present disclosure.

In an aspect, an adjunct for a gastrointestinal device includes, but is not limited to, a flexible tubular substrate configured to attach to a gastrointestinal device, the flexible tubular substrate including an inner surface and an outer surface; and a plurality of at least one type of commensal microbe associated with at least a portion of at least one of the inner surface and the outer surface of the substrate. In addition to the foregoing, other aspects of a device are described in the claims, drawings, and text forming a part of the present disclosure.

In an aspect, a gastrointestinal system includes, but is not limited, a gastrointestinal device; and an adjunct configured to attach to the gastrointestinal device, the adjunct including a substrate, the substrate including a first surface and a second surface, and a plurality of at least one type of commensal microbe associated with at least a portion of at least one of the first surface and the second surface of the substrate. In addition to the foregoing, other aspects of a system are described in the claims, drawings, and text forming a part of the present disclosure.

In an aspect, an adjunct for a gastrointestinal device includes, but is not limited to, a substrate configured to attach to a gastrointestinal device, the substrate including a first surface and a second surface; and at least one microbe-promoting agent associated with at least one of the first surface and the second surface of the substrate, the at least one microbe-promoting agent configured to promote at least one of attraction, colonization, and growth of at least one type of commensal microbe. In addition to the foregoing, other aspects of a device are described in the claims, drawings, and text forming a part of the present disclosure.

In an aspect, an adjunct for a gastrointestinal device includes, but is not limited to, a flexible tubular substrate configured to attach to a gastrointestinal device, the flexible tubular substrate including an inner surface and an outer surface; and at least one microbe-promoting agent associated with at least one of the inner surface and the outer surface of the flexible tubular substrate, the at least one microbe-promoting agent configured to promote at least one of attraction, colonization, and growth of at least one type of commensal microbe. In addition to the foregoing, other aspects of a device are described in the claims, drawings, and text forming a part of the present disclosure.

In an aspect, a gastrointestinal system includes, but is not limited to, a gastrointestinal device; and an adjunct configured to attach to the gastrointestinal device, the adjunct including a substrate, the substrate including a first surface and a second surface, and at least one microbe-promoting agent associated with at least one of the first surface and the second surface of the substrate, the at least one microbe-promoting agent configured to promote at least one of attraction, colonization, and growth of at least one type of commensal microbe. In addition to the foregoing, other aspects of a system are described in the claims, drawings, and text forming a part of the present disclosure.

BRIEF DESCRIPTION OF THE FIGURES

FIG. 24A is a schematic of an embodiment of a gastrointestinal system including a gastrointestinal device and an adjunct for a gastrointestinal device including a plurality of at least one type of commensal microbe.

FIG. 24B is a schematic of an embodiment of a gastrointestinal system positioned in a gastrointestinal tract.

FIG. 40A is a schematic of an embodiment of a gastrointestinal system including a gastrointestinal device and an adjunct for a gastrointestinal device including at least one microbe-promoting agent.

FIG. 40B is a schematic of an embodiment of a gastrointestinal system positioned in a gastrointestinal tract.

DETAILED DESCRIPTION

Figure 1:
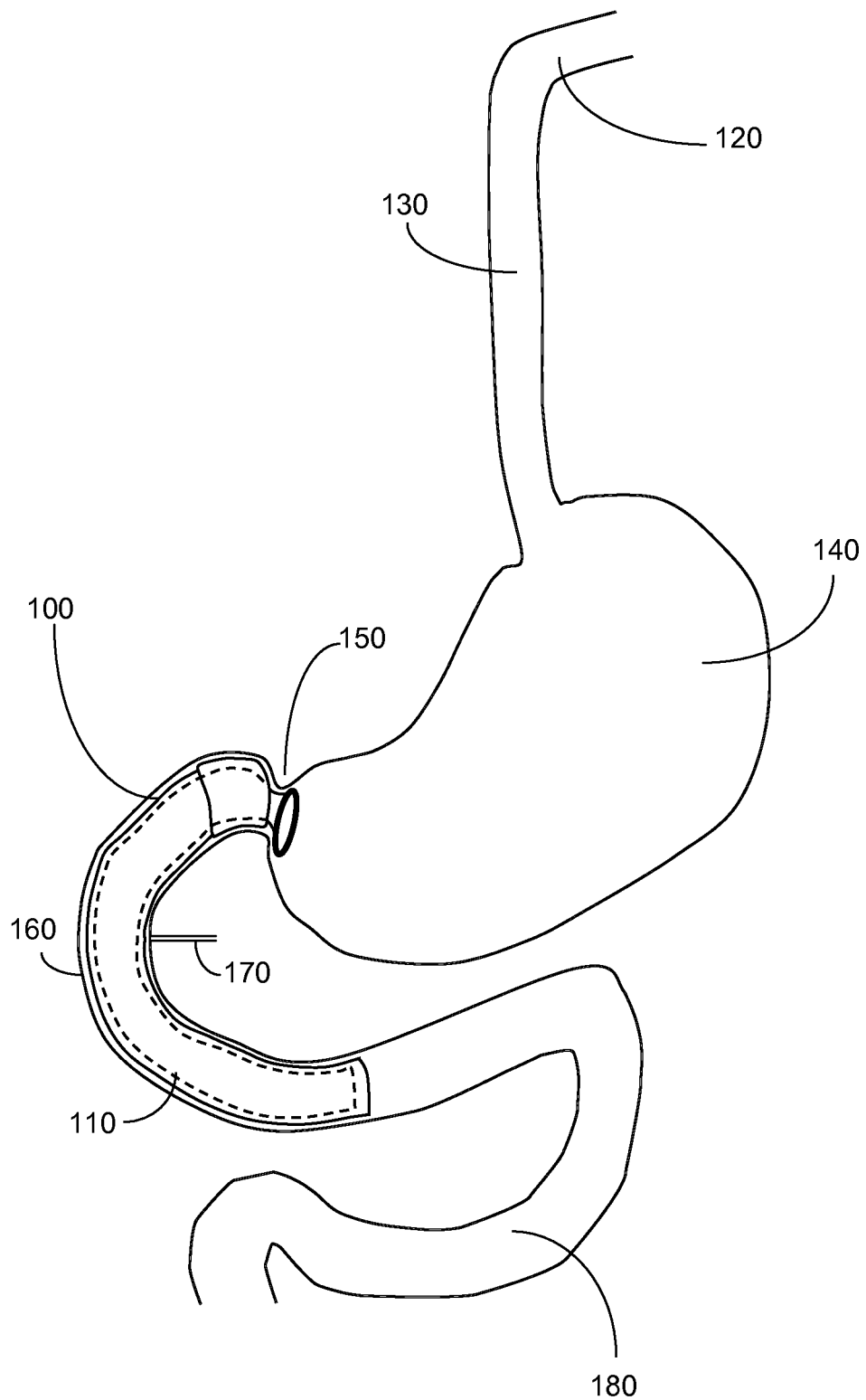
FIG. 1 is a schematic of an adjunct for a gastrointestinal device positioned in the gastrointestinal tract of a subject.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Described herein are devices and methods for establishing, maintaining, supporting, and/or altering the health of a mammalian digestive system, including its flora, to treat a medical condition (e.g., an inflammatory disease, metabolic disease, cancer, microbial infection, ischemia, stricture, obstruction, or trauma) and/or dietary need (e.g., nutritional need, weight control, and/or food sensitivity). Intraluminal devices are well known as means to treat disorders of the gastrointestinal tract and to promote dietary and weight control. These devices include gastrointestinal endoluminal sleeves, liners, and stents, which function, for example, to bypass a diseased or damaged portion of the gastrointestinal tract, to bypass a portion of the gastrointestinal tract (e.g., the small intestine) to reduce absorption (e.g., in weight loss), or to structurally support diseased or damaged portions of the gastrointestinal tract. Such devices, however, neglect the importance of commensal microbes that normally reside in the gastrointestinal tract and the roles they play in the coordinated function of the gastrointestinal tract. Disruption or bypass of the flow of food or chyme through the gut, and thus its normal exposure to commensal microbes, can result in complications including diarrhea and vitamin and micronutrient insufficiencies, as well as disruptions in normal flora in nearby tissues.

The mammalian gastrointestinal tract includes an array of endogenous microbes that make up the microbiota. The microbiota of gut flora includes bacteria, fungi, archaea, and viruses. For example, the human gut, defined here as any part of the alimentary canal or gastrointestinal tract, is home to approximately 100 trillion bacteria cells. Humans have co-evolved to exist with this microbial community largely in a mutualistic relationship where humans as host rely on these microorganisms for a number of key functions related to nutrition, energy balance, susceptibility to obesity, education of the immune system, and prevention of infection by pathogenic species. In turn, humans provide a source of nutrition to the microbial community in the form of mucus lining the inner surface of the gastrointestinal tract. Furthermore, the microbial lineages present in the gut appear to be at least partially dependent upon the types of foods ingested, the diet providing nutrients to both the host and microbial community. For example, abundant *Prevotella* correlate with consumption of carbohydrates, while abundant *Bacteroides* correlate with consumption of choline, fats, and amino acids. For example, a more diverse diet correlates with increased gut bacterial diversity. See, e.g., Hoffman et al. (2013) *PLoS ONE* 8(6): e66019, which is incorporated herein by reference. Thus, a healthy and intact microbiota is important to both digestive and general health, and disruptance of the microbiota has been associated with numerous disease processes including inflammatory bowel diseases, metabolic diseases (e.g., type 2 diabetes and obesity), cancer, and infection, particularly with *Clostridium difficile* infection. See, e.g., Wu & Lewis (2013) *Clin. Gastroenterol. Hepatol.* 11:774-777; Cox & Blaser (2013) *Cell Metab.* 17:883-894; Maynard et al. (2012) *Nature* 489:231-241, which are incorporated herein by reference.

With reference to FIG. 1, shown is a view of a portion of the gastrointestinal tract including a gastrointestinal device 100, e.g., a gastrointestinal sleeve. An adjunct 110 to a gastrointestinal device is shown disposed in and extending along the inner lumen of gastrointestinal device 100. During digestion, food enters the mouth 120, is chewed, and passes down the esophagus 130 to the stomach 140. The stomach 140 converts the ingested food into chyme, a thick semi-solid mass. The chyme passes through the pylorus 150 and into the duodenum 160 of the small intestine, past an inlet 170 from the bile duct and the pancreas, and onto the jejunum 180. In this non-limiting embodiment, gastrointestinal device 100 with attached adjunct 110 is positioned in the duodenum 160 distal to the pylorus 150. In some embodiments, gastrointestinal device 100 may be placed in a mouth, an esophagus, a stomach, a pylorus, a duodenum, a jejunum, an ileum, a caecum, a sphincter, a duct, a biliary duct, a pancreatic duct, a gland, an ascending colon, a transverse colon, a descending colon, a sigmoid colon, a rectum, an anus, or a combination thereof of a subject.

In an embodiment, an adjunct for a gastrointestinal device includes a substrate configured to attach to a gastrointestinal device, the substrate including a first surface and a second surface, and a plurality of at least one type of commensal microbe associated with at least a portion of at least one of the first surface and the second surface of the substrate.

In an embodiment, an adjunct for a gastrointestinal device includes a substrate configured to attach to a gastrointestinal device, the substrate including a first surface and a second surface, and at least one microbe-promoting agent associated with at least one of the first surface and the second surface of the substrate, the at least one microbe-promoting agent configured to promote at least one of attraction, colonization, and growth of at least one type of commensal microbe.

In an aspect, the adjunct for a gastrointestinal device includes an add-on, an appendage, an appurtenance, an enhancement, an attachment, an auxiliary portion, an addition, a supplement, or an addendum to a gastrointestinal device. In an aspect, the adjunct for a gastrointestinal device includes an adjunct device for a gastrointestinal device. For example, the adjunct includes a device configured to attach to a gastrointestinal device. For example, the adjunct device can include an add-on device, an appendage device, an appurtenance device, an enhancement device, an attachment device, an auxiliary device, an additional device, a supplemental device, or an addendum device to a gastrointestinal device.

The adjunct for a gastrointestinal device is configured to attach to a gastrointestinal device. In an aspect, the adjunct for a gastrointestinal device is configured to attach to a gastrointestinal device sized for placement in a portion of the gastrointestinal tract of the subject. In an aspect, the adjunct for a gastrointestinal device is configured to attach to a gastrointestinal device sized for placement in a mouth, an esophagus, a stomach, a pylorus, a duodenum, a jejunum, an ileum, a caecum, a sphincter, a duct, a biliary duct, a pancreatic duct, a gland, an ascending colon, a transverse colon, a descending colon, a sigmoid colon, a rectum, an anus, or a combination thereof of the subject. In an aspect, the adjunct for a gastrointestinal device is configured to attach to a gastrointestinal device sized for placement in a portion of the gastrointestinal tract, the gastrointestinal device including a flow conduit from a proximal end to a distal end in fluid communication with at least a portion of the gastrointestinal tract. For example, the adjunct for a gastrointestinal device a gastrointestinal device is configured to attach to a gastrointestinal device appropriately sized for allowing passage of ingested food and/or chyme through the internal portion of the gastrointestinal device without becoming obstructed.

In an aspect, the adjunct for a gastrointestinal device includes a substrate sized to attach to a gastrointestinal sleeve, a gastrointestinal liner, or a gastrointestinal stent. In an aspect, the adjunct for a gastrointestinal device includes a substrate sized to attach to a gastrointestinal device along the full length of the gastrointestinal device or any portion of the length of the gastrointestinal device. In an embodiment, the adjunct for the gastrointestinal device includes a substrate sized to fully match the width of the gastrointestinal device. In an embodiment, the adjunct for a gastrointestinal device includes a substrate configured as noncontiguous along at least a portion of the length and/or width of the gastrointestinal device.

In an aspect, the adjunct for a gastrointestinal device includes a substrate sized to attach to a gastrointestinal sleeve. For example, the substrate of the adjunct for a gastrointestinal device can be sized to attach to a gastrointestinal device that includes a sleeve with an anchoring mechanism, the sleeve configured to extend into the gastrointestinal tract. Non-limiting examples of gastrointestinal devices including a sleeve are described in U.S. Pat. No. 7,037,344 to Kagan et al. titled "Apparatus and Methods for Treatment of Morbid Obesity;" U.S. Patent Application No. 2013/0331759 from Neisz et al. titled "Device and Methods for Gastrointestinal Bypass;" and U.S. Patent Application No. 2014/0012178 from Chin titled "System and Methods for Bariatric Therapy," which are incorporated herein by reference. In an aspect, the adjunct for a gastrointestinal device includes a substrate sized to attach to a gastrointestinal liner. For example, the substrate of the adjunct for a gastrointestinal device can be sized to attach to a gastrointestinal device that includes an implantable gastrointestinal liner, for example, a duodenal-jejunal bypass liner. A non-limiting example of a duodenal-jejunal bypass liner is described in Escalona et al. (2012) "Weight Loss and Metabolic Improvement in Morbidly Obese Subjects Implanted for 1 Year with an Endoscopic Duodenal-Jejunal Bypass Liner," *Ann. Surg.* 255:1080-1085, which is incorporated herein by reference. For example, the gastrointestinal device can include a duodenal-jejunal bypass liner such as exemplified by the EndoBarrier liner (from GI Dynamics, Lexington, Mass.). In an aspect, the adjunct for a gastrointestinal device includes a substrate sized to attach to a gastrointestinal stent. For example, the substrate of the adjunct for a gastrointestinal device can be sized to attach to at least one of an esophageal stent, a biliary stent, a gastric stent, an enteral stent, and/or a colorectal stent. Non-limiting examples of gastrointestinal stents are described in Loch & Kahaleh (2007) "Stents for Gastrointestinal Tract and Nutritional Implications," *Practical Gastroenterology January* 2007: 48-57; and Lam-Tsai et al. (2011) "A Review of Gastrointestinal Stenting," *Gastroenterology & Endoscopy News*, June 2011: 1-8, which are incorporated herein by reference.

In an aspect, the adjunct for a gastrointestinal device is sized to attach to a gastrointestinal device that replaces or supports a defective or at risk portion of the gastrointestinal tract. In an aspect, the adjunct including the plurality of the at least one type of commensal microbe and a gastrointestinal device act as an artificial gut. For example, the adjunct for a gastrointestinal device can provide a microbial environment in the form of the plurality of the at least one type of commensal microbe that interacts with ingested components or with the gastrointestinal wall. In an aspect, the adjunct for a gastrointestinal device includes a plurality of at least one type of commensal microbes that replaces the digestive and/or nutritional functions of endogenous microbes that are otherwise covered by a portion of the gastrointestinal device. In an aspect, the plurality of the at least one type of commensal microbe forms a microbiome.

In an aspect, the adjunct for a gastrointestinal device includes a substrate sized to attach to a gastrointestinal device of a type configured for treating a medical condition of a subject. For example, the adjunct for a gastrointestinal device can include a substrate sized to attach to a gastrointestinal sleeve, liner, or stent configured for treating a medical condition of a subject. In an aspect, the medical condition of the subject includes at least one of diabetes, obesity, metabolic syndrome, colitis, cancer, ischemia, inflammatory bowel disease, irritable bowel syndrome, an autoimmune disorder, trauma, stricture, or a microbial infection. In an aspect, the medical condition includes a *Clostridium difficile* infection. In an aspect, the medical condition includes Crohn's disease. In an aspect, the medical condition includes ischemia in a portion of the gastrointestinal tract. In an aspect, the medical condition includes a stricture (e.g., in a patient with Crohn's disease). In an aspect, the medical condition includes an obstruction (e.g., a benign or malignant growth). In an aspect, the medical condition includes an irritation or damage to a portion of the gastrointestinal tract. In an aspect, the medical condition includes trauma to a portion of the gastrointestinal tract, for example trauma from injury or due to surgery (e.g., excision of tissue or resection of a portion of the gastrointestinal tract). In an aspect, the medical condition includes obesity.

For example, the adjunct for a gastrointestinal device can include a substrate configured to attach to a gastrointestinal liner configured for inducing weight loss and/or treating associated metabolic syndrome and type 2 diabetes. In an aspect, the adjunct for a gastrointestinal device can include a substrate configured to attach to a gastrointestinal device of a type configured for treating an obstruction (e.g., a benign or malignant growth). For example, the adjunct for a gastrointestinal device can include a substrate configured to attach to a gastrointestinal stent configured for treating a malignant obstruction associated with colorectal cancer. See, e.g., Lam-Tsai et al. (2011) "A Review of Gastrointestinal Stenting," *Gastroenterology & Endoscopy News*, June 2011: 1-8, which is incorporated herein by reference.

The substrate of the adjunct for a gastrointestinal device further includes a plurality of at least one type of commensal microbe. In an aspect, an adjunct attached to an outer surface of the gastrointestinal device is configured to allow the plurality of the at least one type of commensal microbe associated with at least one of the first surface and the second surface of the substrate to come in contact with the gastrointestinal tract. In an aspect, the adjunct for the gastrointestinal device is configured to allow components (e.g., vitamins) secreted by the at least one type of commensal microbe to interact with and/or be absorbed by the gastrointestinal tract. In an aspect, an adjunct attached to an inner surface of the gastrointestinal device is configured to allow the plurality of at least one type of commensal microbe associated with at least one of the first surface and the second surface of the substrate to come in contact with food or chyme flowing through the gastrointestinal device. In an aspect, the adjunct for the gastrointestinal device is configured to allow components secreted by the at least one type of commensal microbe to interact with an ingested product, e.g., one or more components of the food or chyme.

In an aspect, the substrate of the adjunct includes a flexible structure. For example, the substrate of the adjunct can include a flexible structure that conforms in shape to a surface of a gastrointestinal device. For example, the substrate of the adjunct can include a flexible patch or a flexible sheet configured to conform in shape to a surface of a gastrointestinal device.

Figure 2:
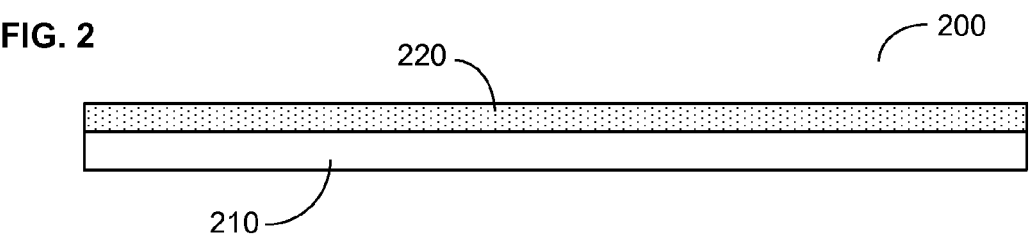
FIG. 2 is a schematic of a longitudinal cross-section through an embodiment of an adjunct for a gastrointestinal device including a plurality of at least one type of commensal microbe.

FIGS. 2-7 illustrate aspects of an adjunct for a gastrointestinal device including a plurality of at least one type of commensal microbe. FIG. 2 shows a longitudinal cross-section through an embodiment of an adjunct for a gastrointestinal device. Adjunct 200 includes a substrate 210 and a plurality of at least one type of commensal microbe 220 (shown as a stippled pattern) on a surface of substrate 210.

In an embodiment, substrate 210 of adjunct 200 includes a patch. For example, the substrate of the adjunct can include a flat structure of an appropriate size to attach to an inner or outer surface of a gastrointestinal device. In an aspect, the patch is square. In an aspect, the patch is rectangular. In an aspect, the patch is circular. The patch can be formed in shapes including, but not limited to, ovoid, triangular, polygonal, trapezoidal, multisided, or any other shape appropriately sized to attach to an inner or outer surface of a gastrointestinal device. In an aspect, the substrate of the adjunct is flexible, e.g., a flexible patch.

In an embodiment, substrate 210 of adjunct 200 includes a sheet. In an aspect, the substrate of the adjunct for a gastrointestinal device includes a flexible sheet. For example, the substrate of the adjunct for a gastrointestinal device can include a flexible sheet configured to wrap around the outside of a gastrointestinal device. For example, the substrate of the adjunct for a gastrointestinal device can include a flexible sheet configured to wrap around the inside of a gastrointestinal device, e.g., the inside of a gastrointestinal sleeve or liner.

In some embodiments of an adjunct for a gastrointestinal device, the plurality of the at least one type of commensal microbe associated with the substrate includes one type of commensal microbe uniformly distributed along at least a portion of at least one of the first surface and the second surface of the substrate. In some embodiments of an adjunct for a gastrointestinal device, the plurality of the at least one type of commensal microbe is associated with one or more portions of the surface of the substrate. In an aspect, the plurality of the at least one type of commensal microbe forms a pattern on the surface of the substrate of the adjunct. In an aspect, the plurality of the at least one type of commensal microbe includes a single genus, species, or strain of commensal microbe. For example, the at least one type of commensal microbe can include a plurality of a single strain of *Bacillus*. In an aspect, the plurality of the at least one type of commensal microbe includes two or more genera, species, or strains of commensal microbe. For example, the at least one type of commensal microbe can include a plurality of a strain of *Bacillus* and a strain of Bactoides. In an aspect, the plurality of the at least one type of commensal microbe includes two or more genera, species, or strains of commensal microbes in a mixture distributed in a uniform pattern.

Figure 3:
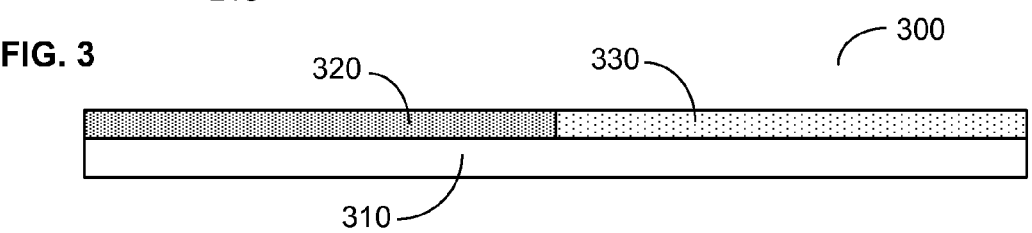
FIG. 3 is a schematic of a longitudinal cross-section through an embodiment of an adjunct for a gastrointestinal device including a plurality of at least one type of commensal microbe.

In an aspect, at least a portion of at least one of the first surface and the second surface of the substrate includes two or more types of commensal microbes. FIG. 3 shows a longitudinal cross-section through an embodiment of an adjunct for a gastrointestinal device. Adjunct 300 includes substrate 310 and a plurality of at least on first type of commensal microbe 320 (shown as a first stippled pattern) associated with at least one first portion of the substrate 310 and a plurality of at least one second type of commensal microbe 330 (shown as a second stippled pattern) associated with at least one second portion of the substrate 310. For example, the adjunct can include a first type of commensal microbe associated with at least one first portion of the substrate and a second type of commensal microbe associated with at least one second portion of the substrate. For example, the adjunct can include a first assortment of commensal microbes including two or more types of commensal microbes on at least one first portion of the substrate and a second assortment of commensal microbe including two or more other types of commensal microbes on at least one second portion of the substrate.

Figure 4:
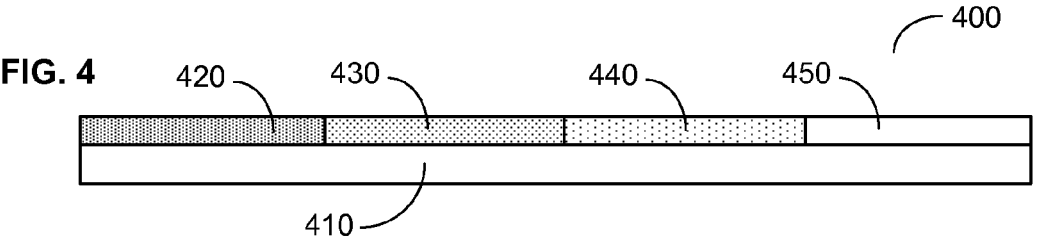
FIG. 4 is a schematic of a longitudinal cross-section through an embodiment of an adjunct for a gastrointestinal device including a plurality of at least one type of commensal microbe.

In an aspect, the plurality of the at least one type of commensal microbe forms a gradient on the at least a portion of the at least one of the first surface and the second surface of the substrate. For example, the plurality of the at least one type of commensal microbe can be distributed in a gradient along the length of at least a portion of the first surface and/or the second surface of the substrate. For example, the concentration of the at least one type of commensal microbe can be greater at the proximal end of the substrate than at the distal end of the substrate, wherein the proximal end and the distal end of the substrate are oriented relative to the proximal end and the distal end of the gastrointestinal device. For example, the concentration of the at least one type of commensal microbe can be greater at the distal end of the substrate than at the proximal end of the substrate. FIG. 4 shows a longitudinal cross-section through an embodiment of an adjunct for a gastrointestinal device. Adjunct 400 includes substrate 410 and a gradient of the plurality of the at least one type of commensal microbe. For example, substrate 410 includes the plurality of at least one type of commensal microbe at a first concentration 420 (shown as a first stippled pattern), at a second concentration 430 (shown as a second stippled pattern), at a third concentration 440 (shown as a third stippled pattern), and a fourth concentration 450. In an aspect, the adjunct can include a gradient of a single type of microbe. In an aspect, the adjunct can include a gradient of two or more types of microbes. In an aspect, the adjunct can include two or more gradients of commensal microbes associated with the substrate. For example, the adjunct can include a first gradient including a plurality of at least one first type of commensal microbe and a second gradient including a plurality of at least one second type of commensal microbe. In an aspect, the plurality of the at least one first type of commensal microbe and the at least one second type of commensal microbe form a gradient on the substrate. For example, the plurality of the at least one first type of commensal microbe forms a gradient from a proximal end to a distal end of the substrate while the plurality of the at least one second type of commensal microbe forms a gradient from the distal end to the proximal end of the substrate.

In an aspect, different combinations and/or concentrations of commensal microbes can be incorporated at different positions along the length of the substrate to allow for temporal and spatial interaction between the commensal microbes and ingested products flowing through the device. In an aspect, different combinations and/or concentrations of commensal microbes can be incorporated at different positions along the length of the substrate to allow for temporal and spatial interaction between the commensal microbes and components of the gastrointestinal wall.

Figure 5:
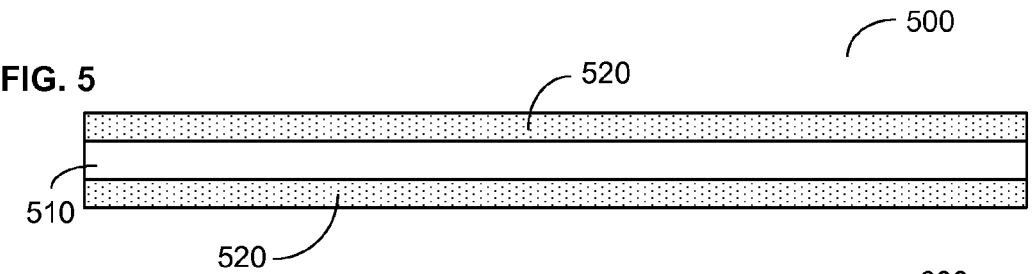
FIG. 5 is a schematic of a longitudinal cross-section through an embodiment of an adjunct for a gastrointestinal device including a plurality of at least one type of commensal microbe.
Figure 6:
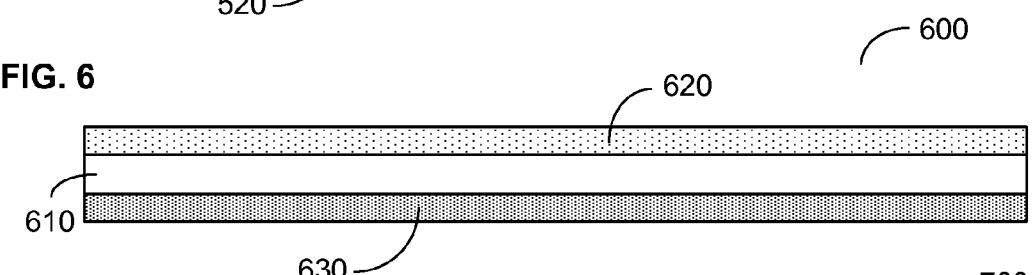
FIG. 6 is a schematic of a longitudinal cross-section through an embodiment of an adjunct for a gastrointestinal device including a plurality of at least one type of commensal microbe.
Figure 7:
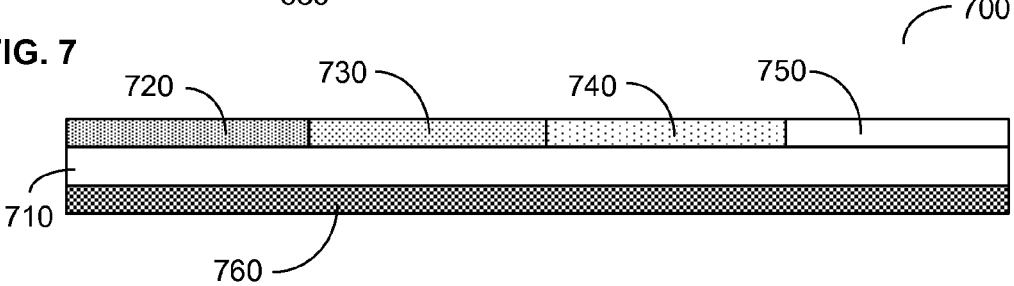
FIG. 7 is a schematic of a longitudinal cross-section through an embodiment of an adjunct for a gastrointestinal device including a plurality of at least one type of commensal microbe.

FIG. 5 shows a longitudinal cross-section through an embodiment of an adjunct for a gastrointestinal device. Adjunct 500 includes substrate 510 and a plurality of at least one type of commensal microbe 520 on both the first and second surface of the substrate 510 (shown as a stippled pattern). In an aspect, the plurality of at least one type of commensal microbe 520 is associated with at least a portion of a first surface and a second surface of substrate 510. FIG. 6 shows a longitudinal cross-section through an embodiment of an adjunct for a gastrointestinal device. Adjunct 600 includes substrate 610 and a plurality of at least one first type of commensal microbe 620 (shown as first stippled pattern) on a first surface of the substrate 610 and a plurality of at least one second type of commensal microbe 630 (shown as a second stippled pattern) on a second surface of the substrate 610. In an aspect, the plurality of the at least one first type of commensal microbe 620 is associated with at least a portion of the first surface of substrate 610 and the plurality of the at least one second type of commensal microbe 630 is associated with at least a portion of the second surface of substrate 610. FIG. 7 shows a longitudinal cross-section through an embodiment of an adjunct for a gastrointestinal device. Adjunct 700 includes substrate 710 and a gradient of at least one first type of commensal microbe on a first surface of substrate 710 and a plurality of at least one second type of commensal microbe on a second surface of substrate 710. For example, substrate 710 includes the plurality of at least one type of commensal microbe at a first concentration 720 (shown as a first stippled pattern), at a second concentration 730 (shown as a second stippled pattern), at a third concentration 740 (shown as a third stippled pattern), and a fourth concentration 750 on a first surface of substrate 710 and a plurality of at least one second type of commensal microbe 760 on a second surface of substrate 710.

In some embodiments, the substrate of the adjunct for a gastrointestinal device includes a tubular structure. In an aspect, the tubular structure defines a lumen. In an aspect, the substrate of the adjunct for a gastrointestinal device forms a sleeve or liner. For example, the substrate of the adjunct for a gastrointestinal device can form a sleeve or liner configured to fit over a commercially available gastrointestinal device, e.g., a commercially available sleeve, liner, or stent. For example, the substrate of the adjunct for a gastrointestinal device can form a sleeve or liner configured to fit inside a commercially available gastrointestinal device, e.g., a commercially available sleeve, liner, or stent. In an aspect, a lumen defined by a substrate that is a tubular structure may form a flow conduit through which ingested products are able to flow. In an aspect, the substrate of the adjunct for a gastrointestinal device is flexible. For example, the substrate is formed from a flexible material, e.g., a flexible polymer, the flexible material conforming to a shape defined by the gastrointestinal device. In an aspect, the substrate of the adjunct of the gastrointestinal device includes a flexible tubular structure.

Figure 8:
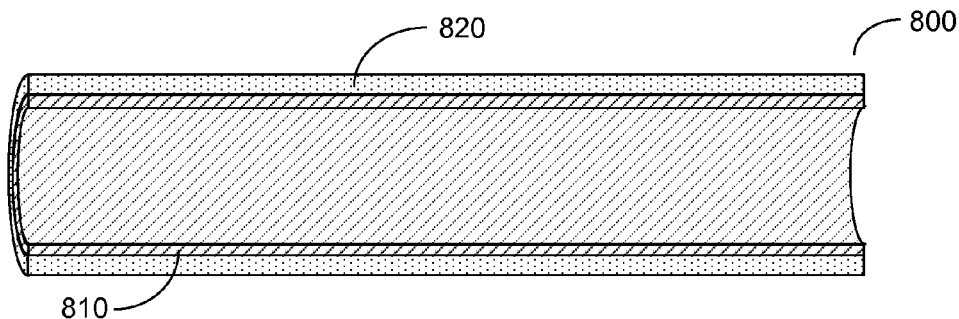
FIG. 8 is a schematic of a longitudinal cross-section through an embodiment of a tubular adjunct for a gastrointestinal device including a plurality of at least one type of commensal microbe.

FIGS. 8-12 illustrate aspects of a substrate of an adjunct for a gastrointestinal device that includes a tubular structure. FIG. 8 shows a longitudinal cross-section through an embodiment of a tubular adjunct for a gastrointestinal device. Tubular adjunct 800 includes tubular substrate 810 (diagonal pattern) and a plurality of at least one type of commensal microbe 820 (stippled pattern) associated with an outer surface of tubular substrate 810. In an aspect, the plurality of at least one type of commensal microbe includes a single type of commensal microbe. In an aspect, the plurality of at least one type of commensal microbe includes a mixture of two or more types of commensal microbe. In an aspect, the plurality of at least one type of commensal microbe 820 is associated with the entirety of the outer surface of tubular substrate 810. In an aspect, the plurality of at least one type of commensal microbe 820 is associated with at least a portion of the outer surface of tubular structure 810.

Figure 9:
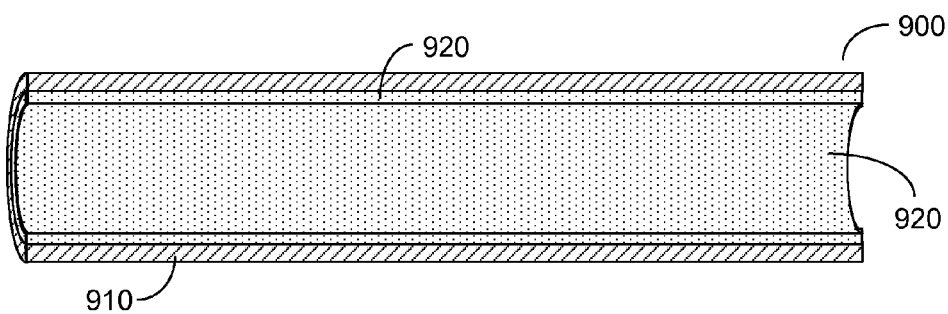
FIG. 9 is a schematic of a longitudinal cross-section through an embodiment of a tubular adjunct for a gastrointestinal device including a plurality of at least one type of commensal microbe.

FIG. 9 shows a longitudinal cross-section through an embodiment of a tubular adjunct for a gastrointestinal device. Tubular adjunct 900 includes tubular substrate 910 (diagonal pattern) and a plurality of at least one type of commensal microbe 920 (stippled pattern) associated with an inner surface of tubular substrate 910. In an aspect, the plurality of at least one type of commensal microbe 920 includes a single type of commensal microbe. In an aspect, the plurality of at least one type of commensal microbe 920 includes a mixture of two or more types of commensal microbe. In an aspect, the plurality of at least one type of commensal microbe 920 is associated with the entirety of the inner surface of tubular substrate 910. In an aspect, the plurality of at least one type of commensal microbe 920 is associated with at least a portion of the inner surface of tubular structure 910.

Figure 10:
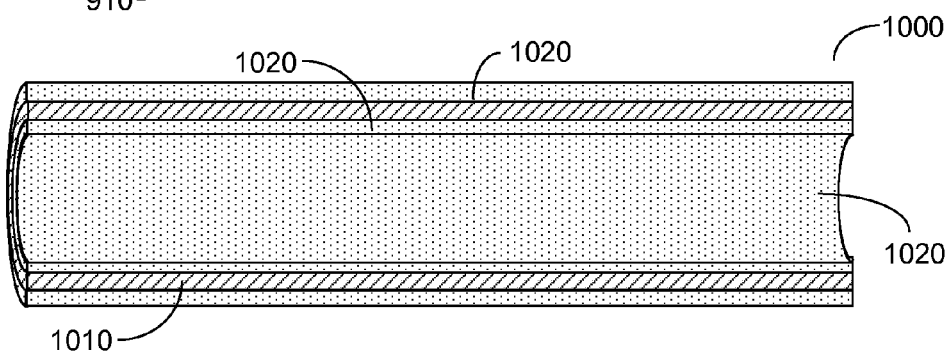
FIG. 10 is a schematic of a longitudinal cross-section through an embodiment of a tubular adjunct for a gastrointestinal device including a plurality of at least one type of commensal microbe.

FIG. 10 shows a longitudinal cross-section through an embodiment of a tubular adjunct for a gastrointestinal device. Tubular adjunct 1000 includes tubular substrate 1010 (diagonal pattern) and a plurality of at least one type of commensal microbe 1020 (stippled pattern) on the inner surface and the outer surface of tubular substrate 1010. In an aspect, the plurality of at least one type of commensal microbe 1020 includes a single type of commensal microbe. In an aspect, the plurality of at least one type of commensal microbe 1020 includes a mixture of two or more types of commensal microbe. In an aspect, the plurality of at least one type of commensal microbe 1020 is associated with the entirety of the inner surface and/or the outer surface of tubular substrate 1010. In an aspect, the plurality of at least one type of commensal microbe 1020 is associated with at least a portion of the inner surface and/or the outer surface of tubular structure 1010. In an aspect, tubular adjunct 1000 includes a plurality of at least one first type of commensal microbe on the inner surface of the tubular substrate 1010 and a plurality of at least one second type of commensal microbe on the outer surface of the tubular structure 1010.

Figure 11:
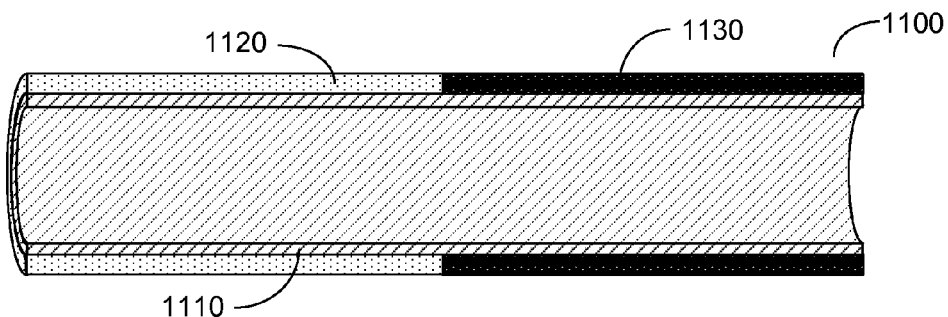
FIG. 11 is a schematic of a longitudinal cross-section through an embodiment of a tubular adjunct for a gastrointestinal device including a plurality of at least one type of commensal microbe.

In an aspect, a tubular adjunct for a gastrointestinal device including a plurality of at least one type of commensal microbe includes two or more types of commensal microbes. In an aspect, the at least one type of commensal microbe includes at least one first type of commensal microbe on a first portion of the inner or outer surface of the tubular substrate and a plurality of at least one second type of commensal microbe on a second portion of the same inner or outer surface of the tubular substrate. FIG. 11 shows a longitudinal cross-section through an embodiment of a tubular adjunct for a gastrointestinal device. Tubular adjunct 1100 includes tubular structure 1110 (diagonal pattern) and a plurality of at least one first type of commensal microbe 1120 (stippled pattern) on a first portion of the outer surface of tubular substrate 1110 and a plurality of at least one second type of commensal microbe 1130 (dark filled pattern) on a second portion of the outer surface of tubular structure 1110.

Figure 12:
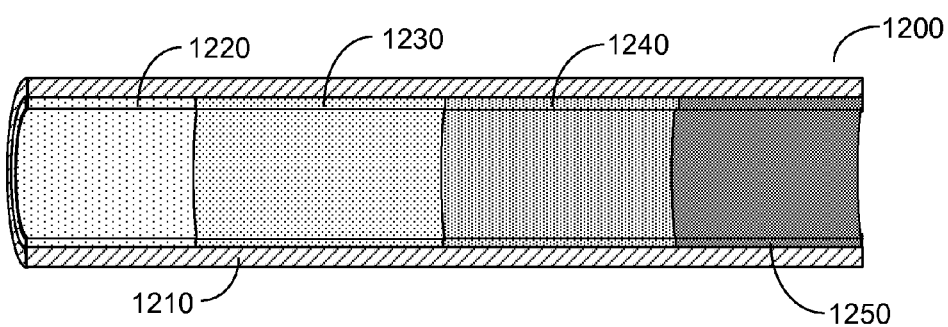
FIG. 12 is a schematic of a longitudinal cross-section through an embodiment of a tubular adjunct for a gastrointestinal device including a plurality of at least one type of commensal microbe.

In an aspect, a tubular adjunct for a gastrointestinal device includes a plurality of at least one type of commensal microbe in a gradient along the inner or outer surface of the tubular substrate. FIG. 12 shows a longitudinal cross-section through an embodiment of a tubular adjunct for a gastrointestinal device. Tubular adjunct 1200 includes tubular substrate 1210 (diagonal pattern) and a plurality of at least one type of commensal microbe forming a gradient on the inner surface of the tubular substrate. In this example, tubular adjunct 1200 includes a plurality of the at least one type of commensal microbe at a first concentration 1220 (first stippled pattern) on a first portion of the inner surface of tubular substrate 1210, a plurality of the at least one type of commensal microbe at a second concentration 1230 (second stippled pattern) on a second portion of the inner surface of tubular substrate 1210, a plurality of the at least one type of commensal microbe at a third concentration 1240 (third stippled pattern) on a third portion of the inner surface of tubular substrate 1210, and a plurality of the at least one type of commensal microbe at a fourth concentration 1250 (fourth stippled pattern) on a fourth portion of the inner surface of tubular substrate 1210.

In an aspect, the substrate is configured to attach to a surface of the gastrointestinal device to form a layered section, the plurality of the at least one type of commensal microbe distributed in the layered section, the layered section configured to allow an interaction between the plurality of the at least one type of commensal microbe and the gastrointestinal tract of the subject. For example, a surface of a substrate including the plurality of the at least one type of commensal microbe is configured to adhere to a surface of a gastrointestinal device, trapping the plurality of the at least one type of commensal microbe between the substrate and the gastrointestinal device. In an aspect, the substrate is formed from a semi-permeable material. For example, the substrate can be formed from a semi-permeable membrane that allows for interaction between the plurality of the at least one type of commensal microbe trapped between the substrate and the gastrointestinal device and components of the gastrointestinal tract. In an aspect, the layered section includes a first layer, a second layer, and an internal space, the first layer associated with the substrate of the adjunct, the second layer associated with the gastrointestinal device, and the internal space disposed between the first layer and the second layer and including the plurality of the at least one type of commensal microbe.

In an aspect, the substrate includes a layered wall, the substrate including the plurality of at least one type of commensal microbe encased in the layered wall. In an aspect, the substrate includes a layered wall configured to allow an interaction between the plurality of the at least one type of commensal microbe and at least one ingested product and/or gastrointestinal component. For example, an adjunct for a gastrointestinal device can include a substrate configured to attach to a gastrointestinal device, the substrate including a layered wall and a plurality of at least one type of commensal microbe encased in the layered wall, the layered wall configured to allow an interaction between the plurality of the at least one type of commensal microbe with at least one of an ingested product and a gastrointestinal component. For example, the substrate can include a layered wall configured to allow components of ingested food or chyme to come in contact with the plurality of the at least one type of commensal microbe encased or entrapped in the layered wall. For example, the substrate can include a layered wall configured to allow components of the gastrointestinal tract to come in contact with the plurality of the at least one type of commensal microbe encased or entrapped in the layered wall. For example, the substrate can include a layered wall configured to allow components secreted by the plurality of the at least one type of commensal microbe to interact with an ingested product and/or the gastrointestinal tract. For example, the substrate can include a layered wall configured to allow components of an ingested product, e.g., after digestion by the at least one type of commensal microbe, to interact with the gastrointestinal tract.

In an aspect, the substrate includes a layered wall including a first layer, a second layer, and an internal space, wherein the internal space is disposed between the first layer and the second layer and includes the plurality of the at least one type of commensal microbe. For example, the substrate can include a patch including a first layer, a second layer, and an internal space, the internal space of the patch including the plurality of the at least one type of commensal microbe disposed between the first layer and the second layer of the patch. In an aspect, the first layer and/or the second layer of the layered wall is formed from a semi-permeable material. For example, the substrate can include a sheet or a tubular structure, the sheet or the tubular structure including a layered wall, the layered wall including a first layer and/or a second layer formed from a semi-permeable material.

In an aspect, the layered wall of the substrate includes an attachment mechanism for holding the first layer and the second layer together. In an aspect, the attachment mechanism includes a material, e.g., an adhesive, adherent, gel, or matrix, in the internal space that holds the first layer and the second layer together. For example, the internal space including the plurality of the at least one type of commensal microbe can include a material, e.g., an adhesive, adherent, gel, or matrix, to which the first layer and the second layer adhere. In an aspect, the attachment mechanism includes one or more staples, stitches, pins, or like mechanism for holding the first layer and the second layer together. For example, the layered wall can include staples to hold the first layer and the second layer together. For example, the first layer and the second layer can be stitched together with a form of biocompatible thread, e.g., suture thread. In an aspect, the first layer and the second layer are fused together at specific points along the length of the substrate in response to a stimulus, e.g., pressure, heat, or chemical stimulus. In an aspect, the attachment mechanism is degradable. For example, an adhesive may lose adhesive strength overtime. For example, the layered wall may include degradable staples or sutures.

In an aspect, the substrate including the plurality of the at least one type of commensal microbe in an internal space of a layered wall includes a permeable material in the internal space. In an aspect, the permeable material includes at least one of a mucus material, a gel material, a porous material, or a fibrous material. For example, the internal space of the layered wall of the substrate can include a material that allows for free flow of fluid and materials through the internal space within the confines of the first layer and second layer of the layered wall. In an aspect, the plurality of the at least one type of commensal microbe is associated with at least one of a porous material, a fibrous material, a mucus material, or a gel material in the layered wall. In an aspect, the plurality of the at least one type of commensal microbe is immobilized in the layered wall. For example, the plurality of at least one type of commensal microbe can adhere to materials (e.g., fibers) or pores associated with an internal space of the layered wall. For example, the at least one type of commensal microbe can line an exposed surface of a pore, allowing for interaction between the at least one type of commensal microbe and an ingested product. In an aspect, the plurality of the at least one type of commensal microbe is diffusible from the layered wall. For example, at least one of the first layer and/or the second layer can be formed from a material sufficiently porous enough to allow passage of the at least one type of commensal microbe.

Figure 13A:
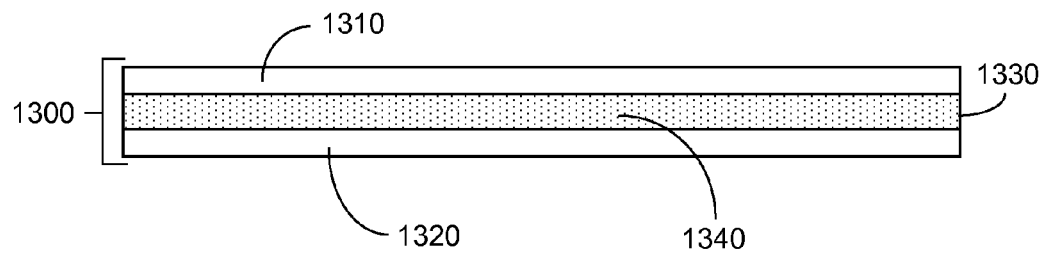
FIG. 13A is a schematic of a longitudinal cross-section through an embodiment of an adjunct for a gastrointestinal device including a substrate having a layered wall.
Figure 13B:
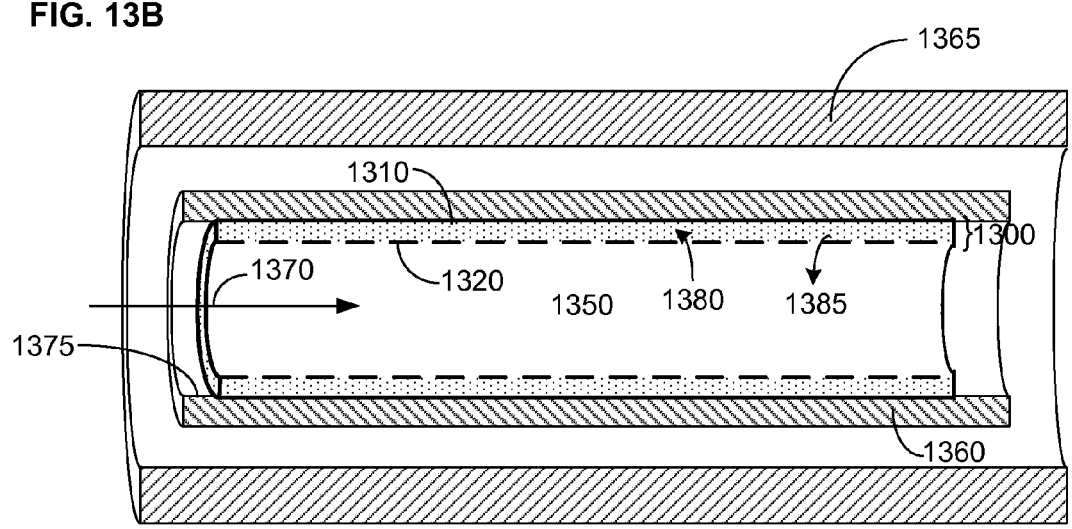
FIG. 13B is a schematic of a longitudinal cross-section through an embodiment of an adjunct attached to a gastrointestinal device positioned in the gastrointestinal tract.
Figure 13C:
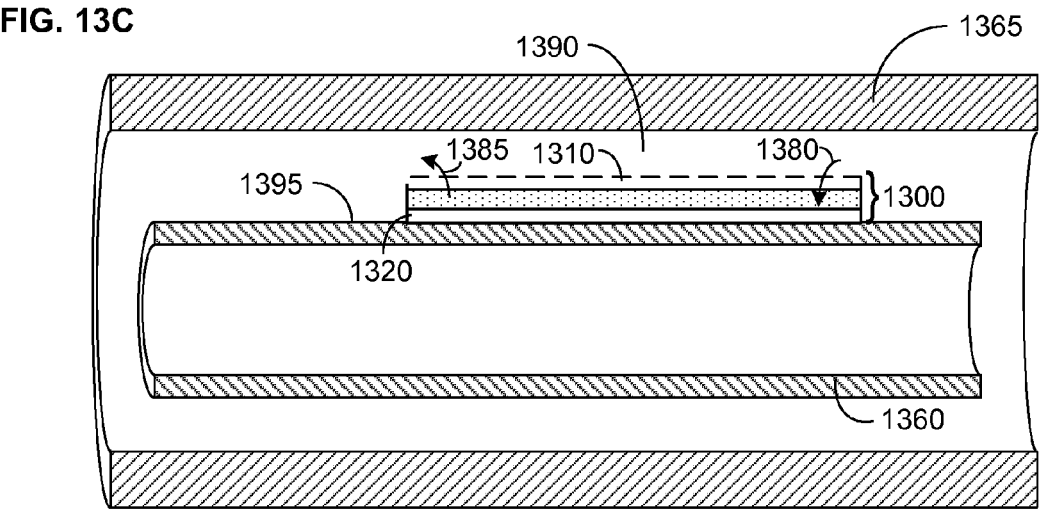
FIG. 13C is a schematic of a longitudinal cross-section through an embodiment of an adjunct attached to a gastrointestinal device positioned in the gastrointestinal tract.

FIGS. 13A-13C illustrate aspects of an embodiment of an adjunct for a gastrointestinal device including a substrate with a layered wall. FIG. 13A shows a longitudinal cross-section through a substrate of an adjunct for a gastrointestinal device. Substrate 1300 includes a layered wall including a first layer 1310, a second layer 1320, and an internal space 1330 disposed between first layer 1310 and second layer 1320. Internal space 1330 further includes a plurality of at least one type of commensal microbe 1340 (stippled pattern).

In an aspect, the adjunct for a gastrointestinal device including a substrate with a layered wall includes a tubular substrate with a layered wall. In an aspect, the tubular substrate including the layered wall is associated with an inner or outer surface of a gastrointestinal device, e.g., a gastrointestinal sleeve, liner, or stent. FIG. 13B illustrates aspects of an adjunct for a gastrointestinal device including a tubular substrate disposed in the gastrointestinal tract. FIG. 13B shows a longitudinal cross-section through gastrointestinal device 1360 disposed in a portion of gastrointestinal tract 1365. Arrow 1370 designates the flow of ingested components through gastrointestinal device 1360. Adjunct 1350 is shown attached to an inner surface 1375 of gastrointestinal device 1360. In an aspect, adjunct 1350 includes an adhesive on an outer surface of the first layer 1310 of the substrate 1300 conforming to a surface of gastrointestinal device 1360. In an aspect, adjunct 1350 includes at least one anchor structure configured to attach adjunct 1350 to gastrointestinal device 1360. Second layer 1320 of substrate 1300 includes a semi-permeable material allowing for interaction between the ingested components and the plurality of at least one type of commensal microbe encased in the internal space of substrate 1300, as indicated by the in arrows 1380 and the out arrows 1385.

In an aspect, the adjunct for a gastrointestinal device including a substrate with a layered wall includes a substrate that is a patch or a sheet. In an aspect, the patch or sheet substrate including the layered wall is associated with an inner or outer surface of a gastrointestinal device. FIG. 13C illustrates aspects of an adjunct for a gastrointestinal device including a patch substrate disposed in the gastrointestinal tract. FIG. 13C shows a longitudinal cross-section through gastrointestinal device 1360 disposed in gastrointestinal tract 1365. Adjunct 1390 is shown attached to an outer surface 1395 of gastrointestinal device 1360. In an aspect, adjunct 1390 includes an adhesive on an outer surface of the second layer 1320 of the substrate 1300 conforming to a surface of gastrointestinal device 1360. In an aspect, adjunct 1390 includes at least one anchor structure configured to attach adjunct 1390 to gastrointestinal device 1360. First layer 1310 of substrate 1300 includes a semi-permeable material allowing for interaction between components of the gastrointestinal tract and the plurality of the at least one type of commensal microbe encased in the internal space of substrate 1300, as indicated by the in arrows 1380 and the out arrows 1385.

Substrate

An adjunct for a gastrointestinal device such as described herein includes a substrate. In some embodiments, the size and/or shape of the substrate is smaller than that of the gastrointestinal device. For example, the substrate can be a patch sized for attachment to a larger gastrointestinal device, e.g., a gastrointestinal sleeve. In some embodiments, the size and/or shape of the substrate is comparable to that of the gastrointestinal device. For example, the substrate can be flexible tubular structure, e.g., a liner, configured to line the entirety of a gastrointestinal device, e.g., a gastrointestinal sleeve or a gastrointestinal stent. In some embodiments, the size and/or shape of the substrate exceeds that of the gastrointestinal device. For example, the substrate can include a patch, sheet, or tubular structure that extends beyond proximal end and/or distal end of the gastrointestinal device.

In an aspect, the substrate includes a patch, a sheet, or a tubular structure. In an aspect, the substrate includes a patch configured to attach to a gastrointestinal device. In an aspect, the substrate includes a sheet configured to attach to a gastrointestinal device. In an aspect, the substrate includes a flexible structure configured to attach to a gastrointestinal device. For example, the substrate can include a pliable plastic, a woven fabric material, soft mesh, or other flexible material. In an aspect, the substrate includes a rigid or semi-rigid structure, e.g., at least one rigid or semi-rigid plastic material. In an aspect, the substrate includes a tubular structure configured to attach to a gastrointestinal device. In an aspect, the substrate includes a flexible tubular structure configured to attach to a gastrointestinal device. In an aspect, the substrate includes at least one biocompatible material. For example, the substrate can include one or more biocompatible plastic materials, one or more bio-compatible fabric materials, or one or more biocompatible metals. In an aspect, the substrate includes at least one biodegradable material. For example, the substrate can include at least one biodegradable material configured to degrade in response to time, moisture, pH, energy, and/or chemical environment.

In an aspect, the substrate of the adjunct for a gastrointestinal device has a shape and dimensions dependent upon the size, dimensions, and use of the gastrointestinal device to which it is intended to be attached. For example, the substrate of the adjunct for a gastrointestinal device can include a flat structure of an appropriate size to attach to an inner or outer surface of a gastrointestinal device. For example, the substrate of the adjunct for a gastrointestinal device can include a patch. In an aspect, the patch is square. In an aspect, the patch is rectangular. In an aspect, the patch is circular. The patch can be formed in shapes including, but not limited to, ovoid, triangular, polygonal, trapezoidal, multisided, or any other shape appropriately sized to attach to an inner or outer surface of a gastrointestinal device. In an aspect, the substrate of the adjunct for a gastrointestinal device is flexible, e.g., a flexible patch. For example, the substrate of the adjunct for a gastrointestinal device can include a flexible patch configured to conform in shape to a surface of the gastrointestinal device.

In an embodiment, the substrate of the adjunct for a gastrointestinal device includes a sheet. In an aspect, the substrate of the adjunct for a gastrointestinal device includes a flexible sheet. For example, the substrate of the adjunct for a gastrointestinal device can include a flexible sheet configured to wrap around the outside of a gastrointestinal device. For example, the substrate of the adjunct for a gastrointestinal device can include a flexible sheet configured to wrap around the inside of a gastrointestinal device, e.g., the inside of a gastrointestinal sleeve or liner.

In an aspect, the substrate of the adjunct for a gastrointestinal device has a thickness, e.g., the distance between the first surface and the second surface of the substrate, which is dependent upon the size and dimensions of the gastrointestinal device to which it is intended to be attached and to the material used to form the substrate. In an aspect, the substrate has a thickness of between about 0.002 mm and about 3 mm. For example, the thickness of the substrate can be about 0.002 mm, 0.005 mm, 0.0075 mm, 0.01 mm, 0.02 mm, 0.03 mm, 0.04 mm, 0.05 mm, 0.06 mm, 0.07 mm, 0.08 mm, 0.1 mm, 0.2 mm, 0.3 mm, 0.4 mm, 0.5 mm, 0.6 mm, 0.7 mm, 0.8 mm, 0.9 mm, 1 mm, 1.1 mm, 1.2 mm, 1.3 mm, 1.4 mm, 1.5 mm, 1.6 mm, 1.7 mm, 1.8 mm, 1.9 mm, 2 mm, 2.1 mm, 2.2 mm, 2.3 mm, 2.4 mm, 2.5 mm, 2.6 mm, 2.7 mm, 2.8 mm, 2.9 mm, or 3 mm in thickness.

In an aspect, the substrate is flexible. In an aspect, the substrate of the adjunct for a gastrointestinal device includes a flexible material, e.g., a material that provides flexibility. In an aspect, the substrate includes a flexible form or structure, e.g., that provides flexibility. In an aspect, the substrate of the adjunct for a gastrointestinal device includes at least one rigid material. For example, the flexibility of a substrate that is a stent may owe its flexibility to a flexible helix design of multiple rigid struts.

In an aspect, the substrate of the adjunct for a gastrointestinal device includes a tubular structure. In an aspect, the substrate of the adjunct for a gastrointestinal device includes a flexible tubular structure. In an aspect, the substrate has a tubular structure including a diameter sized to fit over a gastrointestinal device. In an aspect, the substrate has a tubular structure including a diameter sized to fit inside a gastrointestinal device. In an aspect, the substrate has tubular structure including a diameter consistent with the inner diameter of a given portion of the gastrointestinal tract. In an aspect, the substrate is a flexible circular tube structure with a circular cross-sectional shape. However, the substrate can include tubular structures having cross-sectional shapes with two or more sides. In an aspect, the cross-sectional shape of a substrate with a tubular structure is a multi-sided polygon. For example, the cross-sectional shape of the tubular structure can include 2 sides, 3 sides, 4 sides, 5 sides, 6 sides, 7 sides, 8 sides, 9 sides, 10 sides, or more. For example, the cross-sectional shape of the tubular structure can include a triangle, a square, a pentagon, a hexagon, a heptagon, an octagon, a nonagon, a decagon, or other appropriately sized, multi-sided polygon.

In an aspect, the substrate of the adjunct for a gastrointestinal device includes a tubular structure with a diameter of between about 5 mm and about 40 mm. For example, the substrate can include a tubular structure including a diameter of about 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, 30 mm, 31 mm, 32 mm, 33 mm, 34 mm, 35 mm, 36 mm, 37 mm, 38 mm, 39 mm, or 40 mm.

In an aspect, the substrate of the adjunct for a gastrointestinal device has a length sufficient to cover at least a portion of the gastrointestinal device to which it attaches. In an aspect, the substrate of the adjunct for a gastrointestinal device covers the entire length of the gastrointestinal device. For example, the substrate of the adjunct for a gastrointestinal device can have a length (e.g., about 0.6 meters) comparable to the length of a gastrointestinal device, e.g., a gastrointestinal liner, that extends from the pyloric junction to the jejunum at the ligament of Treitz. For example, the substrate of the adjunct for a gastrointestinal device can have a length (e.g., about 0.1 meters) comparable to a gastrointestinal stent. For example, the substrate of the adjunct for a gastrointestinal device can extend the entire length of the small intestine or about 7 meters. In an aspect, the substrate of the adjunct for a gastrointestinal device has a length of between about 0.001 meters to about 9 meters. For example, the flexible tubular structure can have a length of about 0.001 meters, 0.002 meters, 0.003 meters, 0.005 meters, 0.005 meters, 0.006 meters, 0.007 meters, 0.008 meters, 0.009 meters, 0.01 meters, 0.015 meters, 0.02 meters, 0.05 meters, 0.1 meters, 0.15 meters, 0.2 meters, 0.25 meters, 0.30 meters, 0.35 meters, 0.4 meters, 0.45 meters, 0.5 meters, 0.55 meters, 0.6 meters, 0.65 meters, 0.7 meters, 0.75 meters, 0.8 meters, 0.85 meters, 0.90 meters, 0.95 meters, 1.0 meters, 1.1 meters, 1.15 meters, 1.2 meters, 1.25 meters, 1.30 meters, 1.35 meters, 1.4 meters, 1.45 meters, 1.5 meters, 1.55 meters, 1.6 meters, 1.65 meters, 1.7 meters, 1.75 meters, 1.8 meters, 1.85 meters, 1.90 meters, 1.95 meters, 2 meters, 2.5 meters, 3 meters, 3.5 meters, 4 meters, 4.5 meters, 5 meters, 5.5 meters, 6 meters, 6.5 meters, 7 meters, 7.5 meters, 8 meters, 8.5 meters, or 9 meters.

In an aspect, the substrate of the adjunct for a gastrointestinal device includes a tubular sleeve or liner. For example, the substrate can include a tubular sleeve or liner formed from a thin-walled polymer material such as silicone, polyurethane, nylon, polytetrafluoroethylene, fluorinated ethylene propylene, polyethylene, or other suitable material. See, e.g., U.S. Patent Application No. 2012/0184893 to Thompson et al. titled "Anchors and methods for intestinal bypass sleeves," which is incorporated herein by reference. In an aspect, the sleeve is reinforced with rings or a spiral made of wire and/or plastic to hold the sleeve open. See, e.g., U.S. Pat. No. 7,037,344 to Kagan et al. titled "Apparatus and Methods for Treatment of Morbid Obesity," which is incorporated herein by reference.

In an aspect, the substrate of the adjunct for a gastrointestinal device includes a stent-like structure. In an aspect, the substrate of the adjunct for a gastrointestinal device includes a metal stent-like structure. For example, the substrate of the adjunct for a gastrointestinal device can include a self-expandable metallic stent. See, e.g., U.S. Pat. No. 8,753,407 to Nguyen titled "Temporary protective gastrointestinal device," which is incorporated herein by reference.

In an aspect, the substrate of the adjunct for a gastrointestinal device includes a plastic stent-like structure. For example, the substrate of the adjunct for a gastrointestinal device can include a self-expandable plastic stent. See, e.g., van Boeckel et al. (2012) *BMC Gastroenterology* 12:19, which is incorporated herein by reference. In an aspect, the substrate of the adjunct for a gastrointestinal device includes a stent-like structure configured to expand once placed inside a gastrointestinal device. See, e.g., U.S. Pat. No. 5,662,713 to Andersen & Strecker titled "Medical stents for body lumens exhibiting peristaltic motion," which is incorporated herein by reference. In an aspect, the substrate of the adjunct for a gastrointestinal device is between about 1 cm and about 50 cm. For example, the substrate of the adjunct for a gastrointestinal device can include a stent-like structure that is about 1 cm, 2 cm, 3 cm, 4 cm, 5 cm, 6 cm, 7 cm, 8 cm, 9 cm, 10 cm, 11 cm, 12 cm, 13 cm, 14 cm, 15 cm, 16 cm, 17 cm, 18 cm, 19 cm, 20 cm, 25 cm, 30 cm, 35 cm, 40 cm, 45 cm, or 50 cm in length. In an aspect, at least a portion of the stent-like structure is not flexible.

In an aspect, the substrate of the adjunct for a gastrointestinal device is formed from a material that helps to minimize or prevent tissue in-growth. In an aspect, the substrate of the adjunct for a gastrointestinal device is formed from a material that helps to promote tissue in-growth. In an aspect, the substrate of the adjunct for a gastrointestinal device is formed from a material that is non-irritating to the gastrointestinal tract, so as to aid in removal once removal is desired. In an aspect, the substrate of the adjunct for a gastrointestinal device is formed from a material that allows the gastrointestinal tract to function without complications such as allergic reactions or other adverse side effects. For example, the substrate of the adjunct for a gastrointestinal device is preferably formed from a material that does not cause extended chronic inflammation, does not cause cell disruption or thrombosis, and is not cytotoxic. In an aspect, the substrate of the adjunct for a gastrointestinal device is formed from a material that is suitable for exposure to the gastrointestinal tract and gastrointestinal tract fluids. For example, the substrate of the adjunct for a gastrointestinal device is formed from a material that is compatible with the pH conditions of the gastrointestinal tract. In an aspect, the substrate of the adjunct for a gastrointestinal device is formed from a material that is biodegradable.

In an aspect, the substrate of the adjunct for a gastrointestinal device is formed from a biocompatible material. For example, the substrate of the adjunct for a gastrointestinal device can be formed from a biocompatible material that includes at least one of a metallic compound, a polymer, a plastic, a ceramic, or a composite. For example, the substrate of the adjunct for a gastrointestinal device can be formed from at least one of a natural polymer, a modified natural polymer, and/or a synthetic polymer. For example, the substrate of the adjunct for a gastrointestinal device can be formed from a synthetic biocompatible polymer, e.g., poly (vinyl alcohol), poly(ethylene glycol), or poly(N-2-hydroxypropyl methacrylamide). Non-limiting examples of biocompatible materials include ultra-high-molar-mass polyethylene (UHMWPE), poly(caprolactone), poly(lactic acid) (PLLA), polytetrafluoroethylene (PTFE), polyvinylchloride, polyethersulfone, polyetheretherketone (PEEK), polysulfone, polypropylene, poly(methyl methacrylate) (PMMA), and other acrylics and methacrylics, silicones, and polyurethanes. See, e.g., Vert et al. (2012) *Pure Appl. Chem.* 84:377-410, which is incorporated herein by reference.

In an aspect, the substrate of the adjunct for a gastrointestinal device is formed from a responsive biocompatible material. For example, the substrate of the adjunct for a gastrointestinal device can be formed from a material that changes properties in response to a stimulus, e.g., changes in pH, temperature, or presence of a substance. For example, the substrate of the adjunct for a gastrointestinal device can be formed from poly(N-isopropylacrylamide) (PIPAAm) which changes form in response to changes in temperature.

In an aspect, at least a portion of the substrate of the adjunct for a gastrointestinal device includes a degradable material. For example, all or part of the substrate of the adjunct for a gastrointestinal device can be formed from a material that degrades over time and is passed through the gastrointestinal tract. In an aspect, at least a portion of the substrate of the adjunct for a gastrointestinal device includes a stimulus-responsive degradable material. In an aspect, the stimulus-responsive degradable material includes at least one of a time-responsive degradable material, a moisture-responsive degradable material, a temperature-responsive degradable material, a pH-responsive degradable material, or a chemical-responsive degradable material. In an aspect, all or part of the substrate of the adjunct for a gastrointestinal device is formed from a polymer that includes hydrolytically unstable linkages in the backbone of the polymer. For example, all or part of the substrate of the adjunct for a gastrointestinal device can be formed from a polymer that includes one or more hydrolytically unstable linkages that include a chemical functional group such as, for example, an ester, anhydride, orthoester, or amide. In an aspect, all or part of the substrate of the adjunct for a gastrointestinal device is formed from a polymer that is degraded by microorganisms. In an aspect, only a portion of the substrate of the adjunct for a gastrointestinal device is formed from a degradable material. For example, the substrate of the adjunct for a gastrointestinal device may have easily passable segments that are connected through degradable portions such that degradation of the degradable portions results in breaking the substrate down into easily passable segments. Non-limiting examples of degradable materials include polyhydroxylalkanoates (e.g., poly-3-hydroxybutyrate, polyhydroxyvalerate, and polyhydroxyhexanoate), polylactic acid, polyglycolid, polybutylene succinate, polycaprolactone, polyanhydrides, polyvinyl alcohol, or cellulose esters. For example, at least part of the substrate of the adjunct for a gastrointestinal device can be formed from a degradable material that is responsive to a low pH, e.g., the approximate pH of chyme or about pH 2.0. For example, the substrate of the adjunct for a gastrointestinal device can include a biodegradable stent-like structure. See, e.g., U.S. Pat. No. 8,753,387 to Headley & Geltz titled "Bioabsorbable stents with reinforced filaments," which is incorporated herein by reference.

In some embodiments, the substrate of the adjunct for a gastrointestinal device is formed from a semi-permeable material. In an aspect, the semi-permeable material is selectively permeable. In an aspect, the semi-permeable material allows certain molecules to pass laterally through the at least a portion of the substrate while preventing other molecules from passing laterally through the substrate. For example, the semi-permeable material can be configured to allow certain ingested molecules to pass laterally through the substrate while preventing other ingested molecules from passing laterally through the substrate. For example, the semi-permeable material may allow water and small solutes, e.g., vitamins or nutrients, to pass laterally through the substrate to the underlying wall of the gastrointestinal tract for absorption while preventing the passage of larger components. For example, the semi-permeable material may allow digestive enzymes, e.g., bile or pancreatic enzymes, to pass through the substrate from the gastrointestinal tract. For example, the semi-permeable material may allow vitamins and micronutrients to pass laterally through the substrate to the underlying wall of the gastrointestinal tract for absorption.

In an aspect, the semi-permeable material includes any of a number of polymers, non-limiting examples of which include polymers, copolymers, and/or block polymers of poly(methyl methacrylate), poly(alkyl acrylate), poly(alkyl methacrylate), poly(acrylamide), poly(N-alkyl acrylamide), poly(N-isopropyl acrylamide), poly(N,N-dialkyl acrylamide), poly(methacrylamide), poly(N-alkyl methacrylamide), poly(N-isopropyl methacrylamide), poly(N,N-dialkyl methacrylamide), poly(ethylene oxide), poly(vinyl chloride), poly(vinyl fluoride), poly(aryl ether), poly(vinyl ether), poly(vinyl acetate), poly(vinyl butyral), poly(vinyl formal), poly(acrylonitrile), poly(methacrylonitrile), poly(siloxane), poly(styrene), poly(butylene), poly(isobutylene), poly(isoprene), poly(propylene), poly(methylpentene), poly(vinyl alcohol), or poly(ethylene glycol). See, e.g., U.S. Patent Application No. 2008/0060995 to Zhang et al. titled "Semi-Permeable Membrane," which is incorporated herein by reference.

In an aspect, the semi-permeable material is selectively permeable based on size. For example, the semi-permeable material can be selectively permeable to molecules based on size. For example, the semi-permeable material can include a form of dialysis membrane. For example, the semi-permeable material can include regenerated cellulose, cellulose esters, or cellulose acetate cross-linked in various ways to form films with differing properties and pores sizes. For example, the semi-permeable material can include polyethersulfone, etched polycarbonate, or collagen manufactured to form films with differing properties and pore sizes.

In an aspect, the semi-permeable material is selectively permeable based on hydrophobicity. For example, the semi-permeable material can be selectively permeable to molecules based on hydrophobicity. In an aspect, the semi-permeable material includes a hydrophilic membrane. In an aspect, the semi-permeable material includes a hydrophobic membrane. For example, a hydrophobic semi-permeable membrane can be formed from poly(methyl methacrylate) in ethyl acetate as describe in U.S. Patent Application No. 2008/0060995 to Zhang et al. titled "Semi-Permeable Membrane," which is incorporated herein by reference. In an aspect, the hydrophobicity of a semi-permeable material is altered using an oxygen plasma etching process. For example, the walls of pores near the surface of the semi-permeable material may be converted from substantially hydrophobic to substantially hydrophilic surfaces through the action of oxygen plasma to generate polar groups on the surface of the semi-permeable material. See, e.g., U.S. Pat. No. 5,275,766 to Gadkaree & Hersh titled "Method of Making Semi-Permeable Polymer Membranes," which is incorporated herein by reference.

In an aspect, the semi-permeable material is selectively permeable based on charge. For example, the semi-permeable material can be selectively permeable to molecules based on charge, e.g., positive, negative, or neutral charge. In an aspect, the semi-permeable material includes an ion-exchange membrane. For example, the semi-permeable material can include a semi-permeable membrane with discrete particles of ion exclusion material associated with a porous supporting material, the latter of which is freely permeable. See, e.g., U.S. Pat. No. 3,331,772 to Brownscombe & Kern titled "Desalting water by reverse osmosis through novel semipermeable membranes," which is incorporated herein by reference.

In an aspect, the semi-permeable material includes an active, selectively permeable material. For example, the semi-permeable material may incorporate pumps, e.g., ion pumps or other active transport pumps, to move solutes from low concentration to high concentration.

In an aspect, the semi-permeable material includes a plurality of pores. In an aspect, each of the plurality of pores has a diameter as small as 200 nm and as large as 3000 nm. In an aspect, one or more of the plurality of pores is less than 200 nm in diameter and can be even smaller than 20 nm. In an aspect, the plurality of pores includes at least two pores. In an aspect, the plurality of pores includes 2 pores to about 100 pores. For example, the plurality of pores can include 2 pores, 3 pores, 4 pores, 5 pores, 6 pores, 7 pores, 8 pores, 9 pores, 10 pores, 15 pores, 20 pores, 25 pores, 30 pores, 35 pores, 40 pores, 45 pores, 50 pores, 55 pores, 60 pores, 65 pores, 70 pores, 75 pores, 80 pores, 85 pores, 90 pores, 95 pores, or 100 pores. In an aspect, the plurality of pores includes about 100 pores to about 100,000 pores. In an aspect, the plurality of pores includes over 100,000 pores. In an aspect, the number of pores is dependent upon the manufacturing process. For example, a semi-permeable material formed from a porous material may include substantially more pores than a semi-permeable material into which one or more pores are machined.

In an aspect, the plurality of pores is formed during the course of manufacturing the semi-permeable material. For example, a porous semi-permeable material formed from cross-linking of cellulose and/or cellulose esters will by definition include a plurality of pores. For example, a stent-like substrate includes pores defined by the matrix forming the stent, e.g., a helix design of multiple rigid struts. In an aspect, the semi-permeable material includes a fibrous material. For example, the fibrous material can include cellulose.

In an aspect, the plurality of pores is machined into a material to form the semi-permeable material. For example, the plurality of pores can be machined into a thin sheet of polymer, e.g., poly(propylene), to form the semi-permeable material. In an aspect, each of the plurality of pores is machined into the material with a drill to form the semi-permeable material. In an aspect, each of the plurality of pores is machined into the material using pins and/or needles. For example, the plurality of pores can be machined into the material using a rotary pinned perforation roller with either cold or hot pins. In an aspect, each of the plurality of pores is machined into the material with a laser to form the semi-permeable material. Non-limiting examples of lasers for laser cutting and/or boring include $CO_2$ lasers, neodymium (Nd) lasers, or neodymium yttrium-aluminum-garnet (Nd—YAG) lasers. In an aspect, each of the plurality of pores is machined into the material using a waterjet cutter. For example, each of the plurality of pores can be machined into the material using a waterjet cutter with or without an added abrasive, e.g., garnet or aluminum oxide. In an aspect, the plurality of pores is machined into the material to form the semi-permeable material before the semi-permeable material is used to form the substrate. In an aspect, the plurality of pores is machined into a material already forming the substrate of the adjunct for a gastrointestinal device.

In an aspect, the substrate of the adjunct for a gastrointestinal device is formed from a substantially impermeable material. In an aspect, the substrate of the adjunct for a gastrointestinal device is formed from a material that is substantially impermeable to water and components of the ingested food or chyme. In an aspect, the substrate of the adjunct for a gastrointestinal device is formed from a material that is substantially impermeable to water and components of the gastrointestinal tract.

In an aspect, the substrate of the adjunct for a gastrointestinal device is formed from and/or includes radiopaque and/or sonoreflective materials and/or includes one or more radiopaque and/or sonoreflective markers for enhanced imaging by X-ray, fluoroscopy, and/or ultrasonic imaging so that the position and functional state of the adjunct for a gastrointestinal device can be verified noninvasively. In an aspect, the radiopaque material includes a radiopacifier or a material with a higher electron density compared to the surrounding tissue so that it absorbs X-rays. In an aspect, the radiopaque material or radiopacifier includes at least one of gold, tungsten, zirconium oxide, barium sulphate, or bismuth. For example, the adjunct for a gastrointestinal device can include a polymer and a radiopaque filler, e.g., barium sulfate, bismuth compounds, or tungsten. In an aspect, the sonoreflective marker includes reflective "beads." For example, the sonoreflective marker can include reflective beads formed from stainless steel, nickel/titanium alloy, titanium, and the like. See, e.g., U.S. Patent Application No. 2011/0021888 to Sing titled "Apparatus, Systems, and Methods for Localizing Markers or Tissue Structures within a Body," which is incorporated herein by reference. In an aspect, the sonoreflective marker includes a piezoelectric marker that generates electrical signals when scanned by ultrasound. See, e.g., U.S. Pat. No. 8,282,561 to Towe titled "Piezo Micro-markers for Ultrasound Medical Diagnostics," which is incorporated herein by reference.

Microbes

The adjunct for a gastrointestinal device includes a substrate including a plurality of at least one type of commensal microbe associated with at least one of the first surface and the second surface of the substrate. In an aspect, the plurality of the at least one type of commensal microbe associated with at least one of the first surface and the second surface of the substrate includes one type of commensal microbe uniformly distributed along at least a portion of at least one of the first surface and the second surface of the substrate. In an aspect, the plurality of at least one type of commensal microbe associated with at least one of the first surface and the second surface of the substrate includes two or more types of commensal microbes uniformly distributed along at least a portion of at least one of the first surface and the second surface of the substrate. For example, the substrate can include a coating that includes a mixture of two or more types of commensal microbes. Alternatively, different portions of the substrate can include different types or different proportions of commensal microbes. In an aspect, the substrate includes a plurality of at least one first type of commensal microbe on at least one first portion of the substrate and a plurality of at least one second type of commensal microbe on at least one second portion of the substrate. In an aspect, the plurality of the at least one type of commensal microbe includes at least one first type of commensal microbe on at least one first portion of the substrate and at least one second type of commensal microbe on at least one second portion of the substrate.

In an aspect, the at least one type of commensal microbe includes a type of microbe commonly found in the gastrointestinal tract of a given mammalian subject. For example, the at least one type of commensal microbe can include bacterial strains from Firmicutes and/or Bacteroidetes. In an aspect, the choice of the at least one type of commensal microbe depends upon characteristics of the subject, e.g., age, gender, ethnicity, geographical location, medical history, comorbidities, or subject preferences. In an aspect, the choice of the at least one type of commensal microbe depends upon the intended location of the gastrointestinal device within the gastrointestinal tract to which the adjunct is attached. For example, the population of microbes may change along the gastrointestinal tract. For example, the distribution of microbes in the esophagus may differ from the distribution of microbes in the stomach. For example, the distribution of microbes in the small intestine may differ from the distribution of microbes in the large intestine. For example, the distribution of microbes may vary in various parts of the small intestine, e.g., the duodenum, jejunum, or ileum, or of the large intestine, e.g., colon and rectum. See, e.g., Andersson, et al. (2008) *PLoS ONE* 3:e2836; and Wang and Yang (2013) *World J Gastroenterol* 19:1541-1550, which are incorporated herein by reference.

In an aspect, the at least one type of commensal microbe includes a plurality of at least one type of gut microbe. In an aspect, the at least one type of gut microbe includes at least one type of the most common gut microbes residing in the intestine. In an aspect, the at least one type of gut microbe can include at least one type of Firmicutes. For example, the at least one type of Firmicutes can include one or more representatives of *Lactobacillus*. In an aspect, the at least one type of gut microbe can include at least one type of Bacteroidetes. For example, the at least one type of gut microbe can include at least one type of Actinobacteria, and/or Proteobacteria. For example, the at least one type of Actinobacteria can include one or more representatives of *Bifidobacterium*.

In an aspect, the at least one type of commensal microbe includes a plurality of at least one type of microbe found in the esophagus. In an aspect, the at least one type of commensal microbe includes a plurality of at least one type of microbe found in the stomach. In an aspect, the at least one type of commensal microbe includes at least one type of *Actinomyces, Gemella, Veillonella*, or *Prevotella*.

In an aspect, the plurality of the at least one type of commensal microbe includes a plurality of at least one type of genetically modified microbe. For example, the least one type of genetically modified microbe can include at least one type of microbe genetically modified to produce a beneficial digestive enzyme (e.g., pepsin, trypsinogen, chymotrypsinogen, carboxypeptidase, pancreatic lipase, sterol esterase, phospholipase, nucleases, sucrose, lactase, or maltase). For example, the at least one type of genetically modified microbe can include at least one type of microbe genetically modified to produce a beneficial hormone (e.g., gastrin, somatostatin, secretin, or cholecystokinin) For example, the at least one type of genetically modified microbe can include at least one type of microbe genetically modified to produce mucin. For example, the at least one type of genetically modified microbe can include at least one type of microbe genetically modified to produce a desired nutrient. For example, the at least one type of genetically modified microbe can include at least one type of microbe genetically modified to interact with endogenous microbes, e.g., to inhibit and/or stimulate the growth of specific endogenous microbes. For example, the at least one type of genetically modified microbe can include at least one type of microbe genetically modified to generate a therapeutic agent (e.g., an antimicrobial agent, anti-inflammatory agent, or a chemotherapeutic agent). One or more types of genetically modified microbes (e.g., genetically modified *Escherichia coli* bacteria) can be generated using standard methods.

In an aspect, the plurality of the at least one type of commensal microbe includes a plurality of at least one type of commensal microbe from at least one fecal sample. In an aspect, the at least one type of commensal microbe includes at least one type of microbe harvested or isolated from fecal matter. See, e.g., Borody et al. (2013) *Curr. Gastroenterol. Rep.* 15:337, which is incorporated herein by reference. A non-limiting example of harvesting, screening, and preparing fecal matter from donors is described in Bakken et al. (2011) *Clin. Gastroenterol. Hepatol.* 9:1044-1049, which is incorporated herein by reference.

In an aspect, the at least one type of commensal microbe from the fecal sample includes at least one type of commensal microbe from a fecal sample of the subject. For example, the plurality of at least one type of commensal microbe can include at least one type of commensal microbe harvested or isolated from a fecal sample of the subject at a prior point in time, e.g., at an earlier age. For example, the plurality of the at least one type of commensal microbe can include at least one type of commensal microbe harvested or isolated from a fecal sample of the subject prior to onset of a condition, e.g., obesity, metabolic syndrome, bacterial infection, cancer, ulcerative colitis, or inflammatory bowel disease. For example, the plurality of the at least one type of commensal microbe can include at least one type of commensal microbe harvested or isolated from a fecal sample of the subject prior to a procedure (e.g., surgery) or administration of a drug or treatment (e.g., an antibiotic or chemotherapy) known to disrupt intestinal flora. For example, the plurality of the at least one type of commensal microbe can include at least one type of commensal microbe harvested or isolated from a fecal sample of the subject prior to travel to another country and/or exposure to a new diet.

In an aspect, the at least one type of commensal microbe from the fecal sample includes at least one type of commensal microbe from a fecal sample of one or more other individuals. For example, the at least one type of commensal microbe can include at least one type of commensal microbe from a fecal sample of a biological relative of the subject, e.g., a parent, sibling, or child of the subject, or member of a household e.g., a spouse. For example, the at least one type of commensal microbe can include at least one type of commensal microbe from a fecal sample of one or more individuals having a preferred intestinal microbiota. For example, the at least one type of commensal microbe can be isolated from fecal matter harvested from a thin, slim, or normal weight individual for use in a subject who is overweight/obese and/or suffering from metabolic dysfunction. See, e.g., Tilg & Kaser (2011) *J. Clin. Invest.* 121:2126-2132, which is incorporated herein by reference. For example, the at least one type of commensal microbe can include at least one type of microbe from a fecal sample of one or more individuals with a healthy intestinal microbiota. For example, the at least one type of commensal microbe can be isolated from fecal matter harvested from one or more healthy individuals for use in a subject suffering from *Clostridium difficile* infection. See, e.g., Di Bella et al. (2013) *Infect. Dis. Rep.* 5(2):e13, which is incorporated herein by reference.

In an aspect, the plurality of the at least one type of commensal microbe includes at least part of a gut microbiota. In an aspect, the gut microbiota includes one or more microbes associated with the gut flora. In an aspect, the at least part of the gut microbiota includes at least part of a gut microbiota of the subject. In an aspect, the at least part of a gut microbiota of the subject includes at least part of a gut microbiota of the subject determined at a prior point in time. For example, the at least part of a gut microbiota of the subject can include at least part of a gut microbiota of the subject determined at an earlier age so as to replicate at least part of a youthful microbiota. For example, the at least a part of a gut microbiota of the subject can include at least part of a gut microbiota of the subject determined before the onset of a current condition or therapeutic treatment so as to replicate at least part of a healthy or undisturbed microbiota.

In an aspect, the at least part of the gut microbiota includes at least part of a gut microbiota of one or more other individuals. In an aspect, the at least part of the gut microbiota includes at least part of a healthy gut microbiota. In an aspect, the at least part of the healthy gut microbiota is normalized to the subject based on age, gender, ethnicity, geographical location, diet, medical history, or co-morbidities. For example, the healthy gut microbiota may include a gut microbiota from one or more healthy individuals, e.g., individuals not experiencing an intestinal condition such as ulcerative colitis or *Clostridium difficile* infection. In an aspect, the at least part of the gut microbiota includes at least part of a preferred gut microbiota. For example, the preferred gut microbiota may include a gut microbiota from one or more non-obese and/or healthy weight individuals. In an aspect, the at least part of the gut microbiota includes at least part of a theoretical gut microbiota. For example, the at least part of a theoretical gut microbiota can be determined based on computational analysis of the gut microbiota of individuals with a healthy and/or preferred phenotype. In an aspect, the at least part of the gut microbiota is derived from a fecal sample.

In an aspect, the at least part of the gut microbiota is derived from in vitro culture of one or more types of commensal microbes. In an aspect, at least part of the gut microbiota of an individual is generated in vitro from cultured microbes known to be associated with a specific microbiota. For example, at least part of a gut microbiota can be generated by culturing in vitro representative members of the common classes of bacteria found in a healthy, preferred, or theoretical gut microbiota. For example, the at least part of the gut microbiota can include a small number of representatives of Firmicutes, Bacteriodetes, Actinobacteria, and/or Proteobacteria cultured in vitro and combined for association with the first and/or second surface of the substrate. A variety of bacterial strains, including representative strains of Firmicutes, Bacteriodetes, Actinobacteria, and Proteobacteria are available through the American Type Culture Collection, Manassas, Va.

In an aspect, the plurality of at least one type of commensal microbe includes at least one type of microbe able to affect its gastrointestinal environment. In an aspect, the plurality of at least one type of commensal microbe includes at least one type of microbe able to affect the pH of its environment, thereby promoting the growth of favorable microbes and protecting against infection with deleterious microbes. In an aspect, the plurality of at least one type of commensal microbe includes at least one type of a mucus-stimulating microbe. For example, the at least one type of commensal microbe can include a type of microbe that stimulates cells of the gastrointestinal tract to generate more protective mucus. For example, the at least one type of commensal microbe can include *A. muciniphila*. Other types of microbes capable of acutely increasing intestinal mucus production include *Bifidobacterium bifidum, Campylobacter jejuni, Cyrptosporidium parvum, Entamoeba histolytica, E. coli, Salmonella*, and *Yersinia*.

In an aspect, the plurality of at least one type of commensal microbe includes at least one type of a microbe that aids in the digestion of food. For example, the plurality of at least one type of commensal microbe can include a type of microbe that breaks down complex sugars, proteins, and fats. For example, the plurality of at least one type of commensal microbe can include Lactobacilli. For example, the device may include a microbe that aids in the digestion of food into a product usable by downsteam microbes or subject tissues. For example, the device may include a microbe that aids in the digestion of food so that certain substances (e.g., nutrients, micronutrients, or vitamins) or a portion thereof can cross the semi-permeable material of the device and be absorbed or further processed by the gut. In an aspect, the plurality of at least one type of commensal microbe can include at least one type of microbe that generates vitamins or other nutrients. For example, the plurality of at least one type of commensal microbe can include a type of microbe that generates vitamin K, e.g., *Lactobacillus acidophilus*. For example, the plurality of at least one type of commensal microbe can include a type of microbe that generates B-complex vitamins, e.g., lactic acid bacteria and/or enteric bacteria.

In an aspect, the plurality of the at least one type of commensal microbe includes a phylogenetically diverse mini-microbiota. In an aspect, the plurality of the at least one type of commensal microbe includes a simplified microbiota. For example, the simplified microbiota can include a small number of representatives of Firmicutes, Bacteriodetes, Actinobacteria, and/or Proteobacteria. For example, the simplified microbiota can include a defined mixture of phylogenetically diverse intestinal bacteria capable of stimulating re-establishment of a healthy microbiota. See, e.g., Lawley et al. (2012) *PLoS Pathogen* 8(10): e1002995, which is incorporated herein by reference.

In an aspect, the plurality of the at least one type of commensal microbe includes at least one type of probiotic. In an aspect, the at least one type of probiotic includes at least one type of bacteria that benefits mammalian (particularly human) health, particularly gastrointestinal health. In an aspect, the at least one type of probiotic infers a benefit on the host, e.g., the subject. For example, representatives types of *Lactobacillus* and *Bifidobacterium* significantly influence human health through a range of effects including, but not limited to, detoxification of xenobiotics, biosynthesis of vitamin K, metabolic effects of fermentation of indigestible dietary fiber, positive influence on transit of gastrointestinal contents by peristalsis, competition with pathogenic microbes for nutrients and binding sites on mucosal epithelial cells, and modulation of the host immune response. See, e.g., Hardy et al. (2013) *Nutrients* 5:1869-1912, which is incorporated herein by reference.

In an aspect, the plurality of the at least one type of commensal microbe includes at least one type of *Bifidobacterium*. In an aspect, the at least one type of *Bifidobacterium* includes at least one type of *B. adolescentis*. In an aspect, the at least one type of *Bifidobacterium* includes at least one of *B. laterosporus, B. breve, B. subtilus, B. infantis, B. longum, B. thermophilum, B. animalis*, or *B. bifidum*. In an aspect, the plurality of the at least one type of commensal microbe includes at least one type of *Bacteroides*. In an aspect, the plurality of the at least one type of commensal microbe includes at least one type of *Lactobacillus*. In an aspect, the at least one type of *Lactobacillus* includes at least one of *L. acidophilus, L. casei, L. fermentum, L. salivaroes, L. brevis, L. leichmannii, L. plantarum*, or *L. cellobiosius*. Other non-limiting examples of *Lactobacillus* include *L. reuteri, L.*

*curvatus, L. bulgaricus, L. gasseri, L. caveasicus, L. helveticus, L. lactis, L. salivarius, L. rhamnosus*, or *L. buchneri*.

Other non-limiting examples of probiotics include *Streptococcus thermphilius, Lactococcus lactis cremoris, S. diacetylactis* and *S. intermedius, L. sporogenes* (also known as *Bacillus coagulans*), *Pediococcus acidilactici* and *Pediococcus pentosaceus*, and *Enterococcus faecium*.

In an aspect, the at least one type of probiotic is available from a commercial source. For example, commercially available strains of *L. acidophilus* include NCRM and *Lactobacillus acidophilus* DDS-1, manufactured by Nebraska Cultures, Inc. and *Lactobacillus rhamnosus* GG, manufactured by LGG-Research and Development, which is deposited in the American Type Culture Collection, coded ATCC 53103. Another commercially available strain of *Lactobacillus* is KE-99 LACTO by Probiohealth, Inc. of Los Angeles, Calif.

In an aspect, commensal microbes localized to specific portions of the intestine may be coated on select portions of the inner surface of the substrate in corresponding locations. For example, preferred microbes found in the small intestine of healthy subjects may be coated on the first and/or second surface of the substrate in regions that will line the small intestine or subsections of the small intestine, e.g., jejunum, ileum, duodenum. For example, dominant phylogenetic groups present in the small intestine include *Clostridium* sp., *Streptococcus* sp. and *Escherichia* sp., which are adapted to the acidity and bile components present in the small intestine (see e.g., Zoetendal et al., *ISME Journal* 6: 1415-1426, 2012, which is incorporated herein by reference).

In an aspect, the at least one type of commensal microbe is beneficial to a subject. In an aspect, the at least one type of commensal microbe is beneficial to the immune system of a subject. For example, the at least type of commensal microbe can include *Bacteroides thetaiotaomicron* which has been demonstrated to attenuate *Salmonella enterica*-induced inflammation. See, e.g., Wu & Wu (2012) *Gut Microbes* 3:1, 4-14, which is incorporated herein by reference. In an aspect, the at least one type of commensal microbe is beneficial to a dietary condition of the subject. In an aspect, the dietary condition of the subject includes a dietary need of the subject (e.g., a nutritional need), weight control of the subject (e.g., obesity), or a food sensitivity of the subject (e.g., a gluten sensitivity or inability to digest lactose). For example, the at least one type of commensal microbe can be a source of digestive enzyme needed to break down complex carbohydrates. For example, several bacterial genera, e.g., *Bacteroides, Bifidobacterium*, and *Enterococcus*, are known to synthesize vitamins, e.g., thiamine, folate, biotin, riboflavin, and pathothenic acid. See, e.g., Morowitz et al. (2011) *Surg. Clin. North Am.* 91:771-785, which is incorporated herein by reference. For example, the at least one type of commensal microbe can include *Lactobacillus gasseri* SBT2005, which has been shown to regulate abdominal adiposity in adults with obese tendencies. See, e.g., Kadooka et al. (2010) *Eur. J. Clin. Nutr.* 64:636-643, which is incorporated herein by reference. For example, the at least one type of commensal microbe can include *Bifidobacterium lactis* HN019 and/or *Lactobacillus acidophilus* NCFM, which have been shown to alleviate lactose intolerance. See, e.g., Grover et al. (2012) *Gut Pathogens* 4:15, which is incorporated herein by reference.

In an aspect, the at least one type of commensal microbe is beneficial to a medical condition of a subject. In an aspect, the medical condition includes diabetes, metabolic syndrome, obesity, cancer, colitis, inflammatory bowel disease, irritable bowel syndrome, autoimmune disorder, ischemia, microbial infection, or microbial deficit. In an aspect, the at least one type of commensal microbe is beneficial to the subject with a *Clostridium difficile* infection. In an aspect, the at least one type of commensal microbe is beneficial to the subject with Crohn's disease. See, e.g., Baxter et al. (2014) *Microbiome* 2:20; Moreno-Indias et al. (2014) *Front. Microbiol.* 5:190; Allegretti & Hamilton (2014) *World J. Gastroenterol.* 20:3468-3474, which are incorporated herein by reference.

In an aspect, the plurality of the at least one type of commensal microbe forms a coating on the at least a portion of the at least one of the first surface and the second surface of the substrate. In an aspect, the plurality of the at least one type of commensal microbe forms a biofilm on the at least a portion of the at least one of the first surface and the second surface of the substrate.

In an aspect, the plurality of the at least one type of commensal microbe is associated with a coating material on the at least a portion of the at least one of the first surface and the second surface of the substrate. In an aspect, the plurality of the at least one type of commensal microbe is combined with a coating material prior to application to the substrate. For example, the coating material including the plurality of the at least one type of commensal microbe can be sprayed, dipped, or spread onto at least a portion of at least one of the first surface and the second surface of the substrate. In an aspect, the plurality of the at least one type of commensal microbe is applied to the substrate before or after application of a coating material. For example, the plurality of the at least one type of commensal microbe can be sprayed, dipped, or spread onto at least a portion of at least one of the first surface and the second surface of the substrate followed by application of the coating material. For example, a coating material can be sprayed, dipped, or spread on least a portion of the at least one of the first surface and the second surface of the substrate followed by application of the plurality of the at least one type of commensal microbe. In an aspect, the coating material includes at least one of a degradable coating material, a matrix coating material, a fibrous coating material, a hydrogel coating material, or a mucus coating material.

In an aspect, the plurality of the at least one type of commensal microbe is incorporated into a degradable coating on the at least a portion of the at least one of the first surface and the second surface of the substrate.

In an aspect, coating material includes a matrix coating material. In an aspect, the matrix coating material includes proteins associated with extracellular matrix and/or connective tissue. For example, the matrix coating material can include collagen, fibronectin, fibrin, and/or elastin fibers derived from natural sources or from genetic engineering. See, e.g., Gomes et al. (2012) *Prog. Polym Sci.* 37:1-17, which is incorporated herein by reference.

In an aspect, the coating material includes a fibrous coating material. For example, the coating material can include a fibrous material configured to allow the plurality of the at least one type of commensal microbe to diffuse into and out of the coating material. In an aspect, the fibrous coating material includes cellulose. In an aspect, the fibrous coating material includes a polymer. See, e.g., U.S. Patent Application No. 2013/0131756 to Arnholt et al. titled "Fibrous Matrix Coating Material," which is incorporated herein by reference.

In an aspect, the coating material includes a hydrogel coating material. In an aspect, the hydrogel coating material includes one or more natural polymers, one or more synthetic monomers, or a combination thereof. Non-limiting examples of natural polymers for use in forming hydrogels include chitosan, alginate, fibrin, collagen, gelatin, hyaluronic acid, and dextran. Non-limiting examples of synthetic monomers for use in forming hydrogels include hydroxyethyl methacrylate (HEMA), N-(2-hydroxypropyl) methacrylate (HPMA), N-vinyl-2-pyrrolidone (NVP), N-isopropyl acrylamide (NIPAAm), vinyl acetate (VAc), acrylic acid (AA), methacrylic acid (MAA), polyethylene glycol acrylate/methacrylate (PEGA/PEGMA), polyethylene glycol diacrylate/dimethacrylate (PEGDA/PEGDMA). See, e.g., Lin & Metters (2006) *Adv. Drug Deliv. Res.* 58:1379-1408, which is incorporated herein by reference.

In an aspect, the coating includes a mucus coating material. In an aspect, the mucus coating material includes a natural mucus coating material. For example, the plurality of the at least one type of commensal microbe can be associated with a natural mucus coating on the first surface and/or second surface of the substrate. For example, natural mucus can be isolated from a mammalian tissue, e.g., intestinal tissue, by gently scraping the mucosal layer off of a resected piece of tissue and rinsing in buffer. Natural mucus can also be isolated from feces and/or ileostomy effluent. See, e.g., Ouwehand et al. (2001) *Methods Enzymol.* 337:200-212, which is incorporated herein by reference.

In an aspect, the mucus coating material includes a synthetic mucus coating material. For example, the synthetic mucus coating material can be formed in vitro from one or more common components of mucus, e.g., mucin glycoproteins. For example, the synthetic mucus coating material can include mucin MUC2. For example, the synthetic mucus coating material can include at least one secreted mucin including at least one of MUC2, MUC5AC, MUC5B, MUC6, MUC7, MUC 8, or MUC19. For example, the synthetic mucus coating material can include at least one membrane-bound mucin including least one of MUC1, MUC3A, MUC3B, MUC4, MUC12, MUC13, MUC15, MUC16, MUC17, or MUC20. In an aspect, the synthetic mucus coating material is formed from mucins proteins or any of a group of protein-containing glycoconjugates with high sialic acid or sulfated polysaccharide content that compose the chief constituent of mucus. In an aspect, the synthetic mucus coating material includes a wide variety of glycoconjugates, including mucoproteins, glycoproteins, glycosaminoglycans, and glycolipids.

In an aspect, the mucus coating material is derived from cultured epithelial cells. For example, the cultured epithelial cells can include cultured intestinal epithelial cells. For example, the epithelial cells can include stem cells, e.g., embryonic or mesenchymal stem cells. For example, various lineages of intestinal epithelial cells can be derived from crypt base columnar cells isolated from the bottom of intestinal crypts. See, e.g., Fujii & Sato (2014) *Frontiers in Genetics*, volume 5, article 169, published June 2014, which is incorporated herein by reference. In an aspect, the mucus coating material is produced by a monolayer of cells, e.g., intestinal submucosal cells or cultured intestinal epithelial cells, grown on the first surface and/or second surface of the substrate.

In an aspect, the plurality of the at least one type of commensal microbe is bound to the at least a portion of the at least one of the first surface and the second surface of the substrate. In an aspect, at least one of the plurality of the at least one type of commensal microbe is bound through a selective binding agent to the at least a portion of the at least one of the first surface and the second surface of the substrate. For example, the at least one type of commensal microbe may be bound to the first surface and/or second surface of the substrate through an antibody, aptamer, or other selective binding agent that selectively recognizes and binds components expressed on the exterior of the at least on type of commensal microbe. In an aspect, at least one of the plurality of the at least one type of commensal microbe is bound through a non-selective binding agent to the at least a portion of the at least one of the first surface and the second surface of the substrate. For example, the at least one type of commensal microbe may be bound to the first surface and/or second surface of the substrate through an absorbent, an adsorbent, an adhesive, a gel, or a matrix.

In an aspect, the plurality of the at least one type of commensal microbe is non-covalently attached to the at least a portion of the at least one of the first surface and the second surface of the substrate. Non-limiting examples of non-covalent interactions include hydrogen bonds, ionic bonds, van der Waals forces, and hydrophobic interactions. In an aspect, the plurality of the at least one type of commensal microbe is non-covalently attached to the substrate through protein-protein interactions, e.g., an avidin/biotin protein interaction. For example, the at least one type of commensal microbe can be modified with biotin and non-covalently attached to a surface of the substrate that includes streptavidin or avidin. Other non-limiting examples non-covalent interactions include interactions between ligands and receptors. In an aspect, the plurality of the at least one type of commensal microbe recognizes and binds to an antibody or other binding ligand/receptor associated with at least a portion of the first surface and/or the second surface of the substrate.

In an aspect, the plurality of the at least one type of commensal microbe is irreversibly associated with at least a portion of at least one of the first surface and the second surface of the substrate. For example, the plurality of the at least one type of commensal microbe can be trapped on the first surface and/or second surface of the substrate. For example, the plurality of the at least one type of commensal microbe can be trapped in an enclosure, e.g., a layered wall, associated with the first surface and/or second surface of the substrate. For example, the plurality of at least one type of commensal microbe can be trapped in an alginate enclosure. For example, the plurality of at least one type of commensal microbe can be trapped in a mesh enclosure.

In an aspect, the plurality of at least one type of commensal microbe is reversibly associated with the first surface and/or second surface of the substrate. In an aspect, at least one of the plurality of the at least one type of commensal microbe migrates or diffuses from the first surface and/or second surface of the substrate with the flow of the ingested contents of the gastrointestinal tract, for example, with the natural turn-over that occurs with the growth of a microbial population. In an aspect, the plurality of at least one type of commensal microbe is associated with a fibrous, porous, or gel matrix. In an aspect, the plurality of at least one type of commensal microbe is associated with a fibrous, porous, or gel matrix from which a portion of the at least one type of commensal microbe is able to diffuse over time. In an aspect, the plurality of at least one type of commensal microbe is encased in a degradable material, e.g., a pH degradable material, that breaks down over time, slowly exposing a portion of the at least one type of commensal microbe from the first surface and/or second surface of the substrate.

In an aspect, the plurality of the at least one type of commensal microbe is incorporated into a coating. In an aspect, the plurality of the at least one type of commensal microbe is incorporated into a degradable coating on the at least a portion of the at least one of the first surface and the second surface of the substrate. For example, the plurality of the at least one type of commensal microbe can be incorporated into a coating material that degrades over time to expose the at least one type of commensal microbe. For example, the degradable coating can further include prebiotics, therapeutic agents, or bioactive agents that are released as the coating degrades. In an aspect, the plurality of the at least one type of commensal microbe is incorporated into a stimulus-responsive degradable coating on the at least a portion of the at least one of the first surface and the second surface of the substrate. For example, the plurality of the at least one type of commensal microbe can be incorporated into a coating material that degrades in response to a stimulus, e.g., time, moisture, temperature, pH, or chemicals.

In an aspect, the stimulus-responsive degradable coating includes at least one of a time-responsive degradable coating, a moisture-responsive degradable coating, a temperature-responsive degradable coating, a pH-responsive degradable coating, or a chemical-responsive degradable coating. In an aspect, the stimulus-responsive degradable coating includes a time-responsive degradable coating. For example, the plurality of the at least one type of commensal microbe can be incorporated into a time-responsive degradable coating that degrades over time to expose the at least one type of commensal microbe. In an aspect, the stimulus-responsive degradable coating includes a moisture-responsive degradable coating. For example, the plurality of the at least one type of commensal microbe can be incorporated into a moisture-responsive degradable coating that degrades over time in responsive to moisture associated with the gastrointestinal tract to expose the at least one type of commensal microbe.

In an aspect, the stimulus-responsive degradable coating includes a temperature-responsive degradable coating. For example, the plurality of the at least one type of commensal microbe can be incorporated into a temperature-responsive degradable coating that degrades over time in response to body heat, e.g., 37 degrees centigrade, associated with the gastrointestinal tract to expose the at least one type of commensal microbe. For example, the plurality of the at least one type commensal microbe can be incorporated into a pH-responsive degradable coating that degrades over time in response to pH changes in the gastrointestinal tract as ingested material moves from the stomach (pH 1.0-3.0) into the upper (pH 4.8-8.2) and the lower (pH 7.0-7.5) intestinal tract to expose the at least one type of commensal microbe. Non-limiting examples of temperature-responsive and pH-responsive polymers are described in Schmaljohann (2006) *Adv. Drug Deliv. Rev.* 58:1655-1670, which is incorporated herein by reference.

In an aspect, the stimulus-responsive degradable coating includes a chemical-responsive degradable coating. For example, the plurality of the at least one type of commensal microbe can be incorporated into a chemical-responsive degradable coating that degrades in response to either an endogenous chemical or an administered/ingested chemical to expose the at least one type of commensal microbe. For example, the chemical-responsive degradable coating can include a hydrogel that is responsive to a chemical, e.g., glucose, a protein, an antibody, or an aptamer. See, e.g., Yang et al. (2008) *J. Am. Chem. Soc.* 130:6320-6321; Miyata et al. (2006) *Proc. Natl. Acad. Sci.* 103:1190-1193, which are incorporated herein by reference.

In an aspect, the adjunct for a gastrointestinal device further includes a plurality of at least one first type of commensal microbe in a first degradable coating and a plurality of at least one second type of commensal microbe in a second degradable coating. In an aspect, the first degradable coating and the second degradable coating degrade at different rates. For example, the plurality of the at least one first type of commensal microbe can be in a first time-responsive degradable coating configured to degrade at a first rate and the plurality of the at least one second type of commensal microbe can be in a second time-responsive degradable coating configured to degrade at a second rate. For example, the plurality of the at least one first type of commensal microbe can be in a first stimulus-responsive degradable coating and the plurality of the at least one second type of commensal microbe in a second stimulus-responsive degradable coating, the first stimulus-responsive degradable coating degrading at a different pH or temperature than the second stimulus-responsive degradable coating. For example, the plurality of the at least one first type of commensal microbe can be in a first chemical-responsive degradable coating and the plurality of the at least one second type of commensal microbe in a second chemical-responsive degradable coating, the first chemical-responsive degradable coating degrading in response to a first chemical and the second chemical-responsive degradable coating degrading in response to a second chemical.

Adhesive

In some embodiments, the substrate of the adjunct for the gastrointestinal device is configured to chemically attach to the gastrointestinal device. In an aspect, the substrate includes an adhesive on at least a portion of at least one of the first surface and the second surface. In an aspect, the substrate includes an adhesive on at least one of the first surface and the second surface conforming to a surface of the gastrointestinal device. For example, the substrate can include an adhesive on at least a portion of the inner or outer surface of a tubular substrate configured to adhere to a surface of the gastrointestinal device. For example, the substrate can include an adhesive on one surface of a flexible patch configured to adhere to a surface of the gastrointestinal device. In an aspect, the substrate includes an adhesive of a type expected to irreversibly adhere to the surface of a gastrointestinal device. In an aspect, the substrate includes an adhesive of a type expected to adhere to the gastrointestinal device for a period of time and be removeable and/or degradable. For example, the substrate can include glue, epoxy, sealant, mucilage, paste, or other adhesive or binder material. For example, the substrate can include a pressure sensitive adhesive, e.g., a styrene copolymer pressure-sensitive adhesive. For example, the substrate can include a surgical adhesive. For example, the adhesive can include at least one of cyanoacrylate, octyl-2-cyanoacrylate, or n-butyl-cyanoacrylate. For example, the adhesive can include fibrin glue. For example, the adhesive can include collagen-based compounds. For example, the adhesive can include glutaraldehyde glues. For example, the adhesive can include synthetic polyethylene glycols.

Figure 14A:
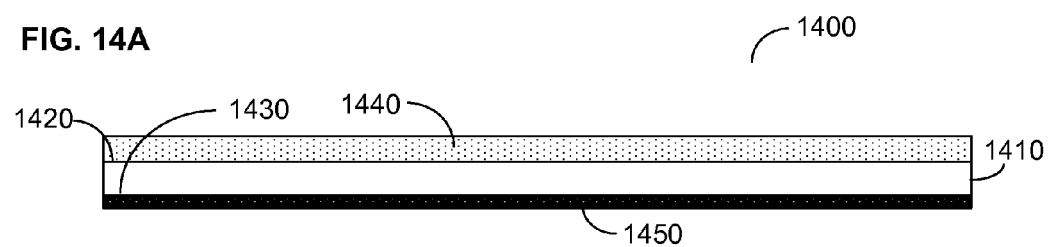
FIG. 14A is a schematic of a longitudinal cross-section through an embodiment of an adjunct for a gastrointestinal device including an adhesive.
Figure 14B:
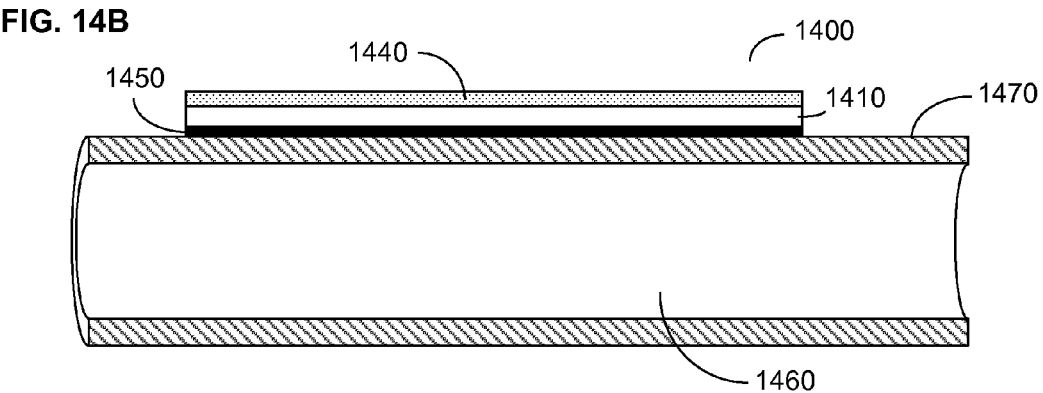
FIG. 14B is a schematic of a longitudinal cross-section through an embodiment of an adjunct for a gastrointestinal device including an adhesive attached to a gastrointestinal device.

FIGS. 14A and 14B illustrate aspects of a substrate (e.g., a patch or a sheet) of an adjunct for a gastrointestinal device including an adhesive. FIG. 14A shows a longitudinal cross-section through adjunct 1400. Adjunct 1400 includes substrate 1410 configured to attach to a gastrointestinal device. Substrate 1410 includes a first surface 1420 and a second surface 1430. Substrate 1410 further includes a plurality of at least one type of commensal microbe 1440 (stippled pattern) associated with at least a portion of first surface 1420 of substrate 1410. Substrate 1410 further includes an adhesive layer 1450 on at least a portion of the second surface 1430 of substrate 1410. FIG. 14B shows a longitudinal cross-section through adjunct 1400 attached to gastrointestinal device 1460. Adjunct 1400 is shown with the second surface of substrate 1410 including adhesive layer 1450 juxtaposed and adhered to the outer surface 1470 of gastrointestinal device 1460. In this non-limiting example, the plurality of at least one type of commensal microbe 1440 is exposed to the gastrointestinal wall. In some embodiments, an adjunct such as adjunct 1400 can be adhered to the inner surface of the gastrointestinal device, exposing the plurality of the at least one type of commensal microbe to ingested components flowing through the gastrointestinal device.

Figure 15:
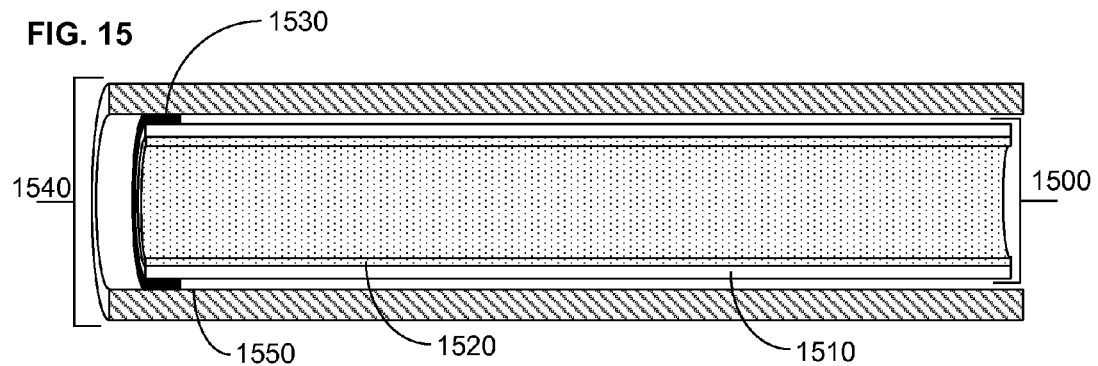
FIG. 15 is a schematic of a longitudinal cross-section through an embodiment of a tubular adjunct for a gastrointestinal device including an adhesive on an outer surface.
Figure 16:
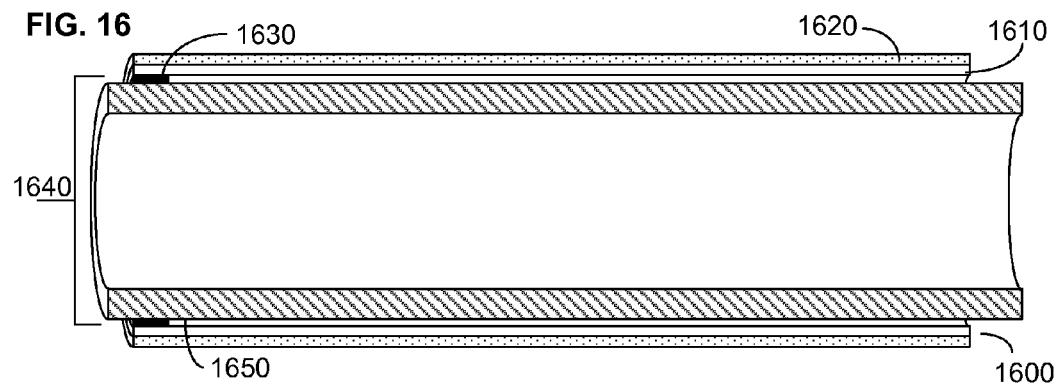
FIG. 16 is a schematic of a longitudinal cross-section through an embodiment of a tubular adjunct for a gastrointestinal device including an adhesive on an inner surface.

FIGS. 15 and 16 illustrate aspects of an adjunct for a gastrointestinal device including a tubular substrate attached to a gastrointestinal device. FIG. 15 shows a longitudinal cross-section through an embodiment of an adjunct for a gastrointestinal device attached with an adhesive to the inner surface of a gastrointestinal device. Adjunct 1500 includes tubular substrate 1510 including a plurality of at least one type of commensal microbe 1520 on a first surface (inner surface) of tubular substrate 1510 and an adhesive layer 1530, e.g., a biocompatible epoxy, on at least a portion of the second surface (outer surface) of tubular substrate 1510. Adhesive layer 1530 is shown adhering adjunct 1500 to at least a portion of the inner surface 1550 of gastrointestinal device 1540. In some embodiments, adhesive layer 1530 can extend along the entire length of tubular substrate 1510 in a contiguous configuration or a noncontiguous configuration (e.g., stripes or rings).

FIG. 16 shows a longitudinal cross-section through an embodiment of an adjunct for a gastrointestinal device attached with an adhesive to the outer surface of a gastrointestinal device. Adjunct 1600 includes tubular substrate 1610 including a plurality of at least one type of commensal microbe 1620 (stippled pattern) on a first surface (outer surface) of tubular substrate 1610 and an adhesive layer 1630 on at least a portion of the second surface (inner surface) of tubular substrate 1610. Adhesive layer 1630 is shown adhering adjunct 1600 to at least a portion of the outer surface 1650 of gastrointestinal device 1640. In some embodiments, adhesive layer 1630 can extend along the entire length of tubular substrate 1610 in a contiguous configuration or a noncontiguous configuration (e.g., stripes or rings).

In an aspect, the adjunct (e.g., a patch, a sheet, or a tubular adjunct) is adhered to the gastrointestinal device prior to insertion of the gastrointestinal device into the gastrointestinal tract. For example, an adjunct configured for attachment to the outer surface of a gastrointestinal device may be adhered to the outer surface of the gastrointestinal device prior to deploying the device in the gastrointestinal tract. In an aspect, the adjunct is adhered to a gastrointestinal device already resident in the gastrointestinal tract. For example, an endoscope or similar type device may be used to deliver the adjunct to the inner surface of a gastrointestinal device.

In an aspect, the substrate includes a plurality of at least one type of commensal microbe on a first surface and an adhesive on the first surface. In an aspect, the substrate includes a plurality of at least one type of commensal microbe on a first portion of the surface of the substrate and an adhesive on a second portion of the surface of the substrate. For example, the substrate can include the plurality of the at least one type of commensal microbe in a central portion of the substrate and an adhesive on a peripheral portion (e.g., along the edges) of the substrate. In an aspect, the first surface is adhered to a surface of a gastrointestinal device such that the plurality of the at least one type of commensal microbe is positioned between the first surface of the substrate and the surface of the gastrointestinal device. In an aspect, the substrate is formed from a semi-permeable material, allowing for interaction between the plurality of the at least one type of commensal microbe and components ingested material and/or components of the gastrointestinal tract.

In an aspect, the first surface and/or the second surface including the adhesive can be covered by a removable protective sheet configured for detachment and exposure of the adhesive when the adjunct is attached to the gastrointestinal device.

Anchoring Structure

In some embodiments, the substrate of the adjunct for the gastrointestinal device is configured to mechanically attach to the gastrointestinal device. In an aspect, the substrate includes at least one anchor structure configured to attach the substrate to the gastrointestinal device. For example, the substrate of the adjunct for a gastrointestinal device can include at least one anchor structure, e.g., at least one barb, configured to attach the substrate to the gastrointestinal device. In an aspect, the at least one anchor structure is associated with at least one of a proximal end and a distal end. In an aspect, the at least one anchor structure is associated with and/or attached to a proximal end of the substrate. In an aspect, the at least one anchor structure is associated with and/or attached to the distal end of the substrate. In an aspect, the at least one anchor structure is incorporated into the substrate. For example, the substrate may be formed to include a surface that includes barbs or hooks configured to attach the substrate to a gastrointestinal device. In an aspect the at least one anchor structure includes barbs, hooks, pins, prongs, or other extensions configured to adhere or fix into a surface of the gastrointestinal device. In an aspect, the at least one anchor structure is inflatable. In an aspect, the at least one anchor structure is expandable. In an aspect, the at least one anchor structure includes a space occupying ring, an inflatable balloon, a self-expanding anchor, or frame, barbs, hooks, springs, coils, disks, or any combination thereof. In an aspect, the at least one anchor structure includes an outer surface of a space occupying ring, inflatable balloon, springs, coils, and/or disks that engages a surface of the gastrointestinal device, exerting an outward or radial force on the surface. In an aspect, the at least one anchor structure includes at least one hook, barb, snap, pin, clip, staple, prong, or other structure that engages a surface of a gastrointestinal device by grabbing, e.g., hooking onto, the surface. In an aspect, the at least one anchor structure is configured to fit a corresponding structure on a surface of the gastrointestinal device, e.g., a lock-and-key configuration or a hook-and-loop configuration.

In an aspect, the anchor structure includes one or more hooks or barbs for engaging a surface of the gastrointestinal device. In an aspect, the one or more hooks or barbs extend out from a surface of the substrate. For example, the one or more hooks or barbs can extend about 2 mm or greater from the surface substrate to engage a surface (e.g., an inner or outer surface) of a gastrointestinal device. In an aspect, the one or more hooks or barbs are positioned so as to point in the direction of forward peristaltic motion. In an aspect, the one or more hooks or barbs are bi-directional to prevent movement of the adjunct in either direction relative to the gastrointestinal device. For example, one or more of the hooks or barbs can be pointed in the direction of forward peristalsis, i.e., the normal flow of ingested food through the gastrointestinal tract, while one or more of the hooks or barbs are pointed in the opposite direction to secure the adjunct in the gastrointestinal device against reverse motion in the gastrointestinal tract. In an aspect, the one or more hooks or barbs are retractable. In an aspect, the one or more hooks or barbs are formed from a degradable material, degrading over a period of time and allowing the adjunct to dislodge from gastrointestinal device and to pass through the remainder of the gastrointestinal tract.

In an aspect, the at least one anchor structure includes a flow conduit continuous with the flow conduit formed by the proximal and distal ends of the adjunct and/or the gastrointestinal device. For example, the at least one anchor structure can include a ring structure defining a central aperture contiguous with the flow conduit of the adjunct and/or the gastrointestinal device. For example, the at least one anchor structure can be toroid in shape, e.g., donut-shaped, with the outer portion of the toroid pressed radially against the surface of a portion of the gastrointestinal device. See, e.g., U.S. Patent Application No. 2014/0012178 to Chin titled "Systems and Methods for Bariatric Therapy," which is incorporated herein by reference. For example, a donut shaped anchor structure can define a central hole through which food or partially digested food can pass into the adjunct and/or the gastrointestinal device.

Figure 17A:
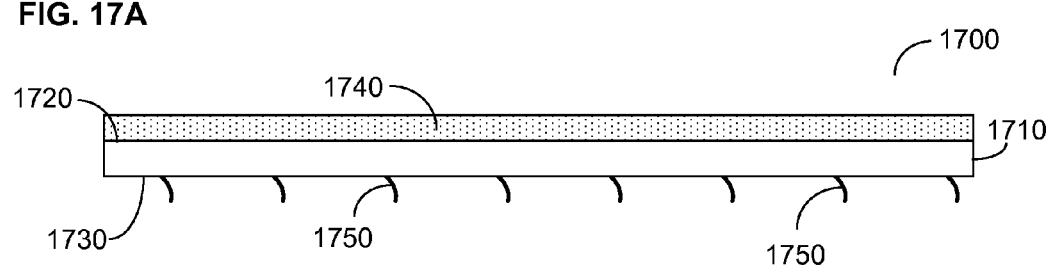
FIG. 17A is a schematic of a longitudinal cross-section through an embodiment of an adjunct for a gastrointestinal device including at least one anchor structure.
Figure 17B:
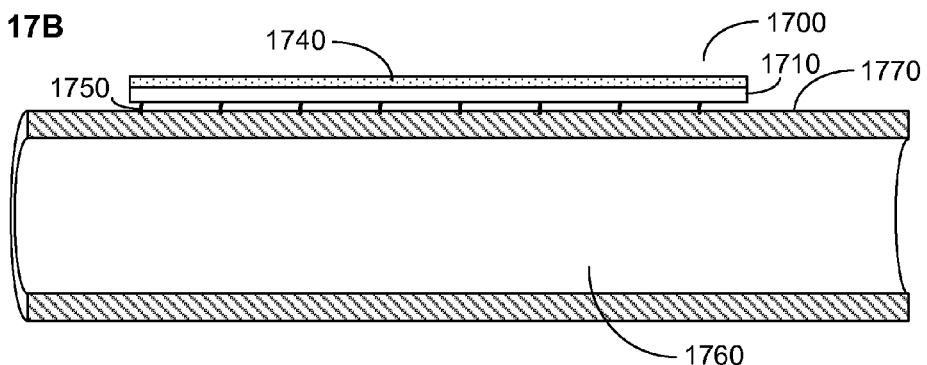
FIG. 17B is a schematic of a longitudinal cross-section through an embodiment of an adjunct for a gastrointestinal device including at least one anchor structure attached to a gastrointestinal device.

FIGS. 17A and 17B illustrate aspects of a substrate (e.g., a patch or a sheet) of an adjunct for a gastrointestinal device including at least one anchor structure. FIG. 17A shows a longitudinal cross-section through adjunct 1700. Adjunct 1700 includes substrate 1710, e.g., a flexible patch or sheet, configured to attach to a gastrointestinal device. Substrate 1710 includes a first surface 1720 and a second surface 1730. Substrate 1710 further includes a plurality of at least one type of commensal microbe 1740 (stippled pattern) associated with at least a portion of first surface 1720 of substrate 1710. Substrate 1710 further includes at least one anchor structure 1750, e.g., at least one hook structure, on at least a portion of the second surface 1730 of substrate 1710. FIG. 17B shows a longitudinal cross-section through adjunct 1700 attached to gastrointestinal device 1760. Adjunct 1700 is shown with the second surface of substrate 1710 including at least one anchor structure 1750 juxtaposed and engaging the outer surface 1770 of gastrointestinal device 1760. In this non-limiting example, the plurality of at least one type of commensal microbe 1740 is exposed to the gastrointestinal wall. In some embodiments, an adjunct such as adjunct 1700 can be attached to the inner surface of a gastrointestinal device, exposing the plurality of the at least one type of commensal microbe to ingested components flowing through the gastrointestinal device.

Figure 18:
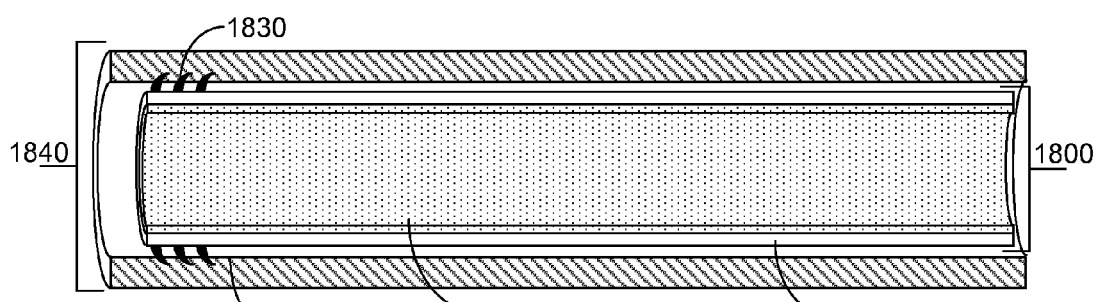
FIG. 18 is a schematic of a longitudinal cross-section through an embodiment of a tubular adjunct for a gastrointestinal device including at least one anchor structure associated with an outer surface.
Figure 19:
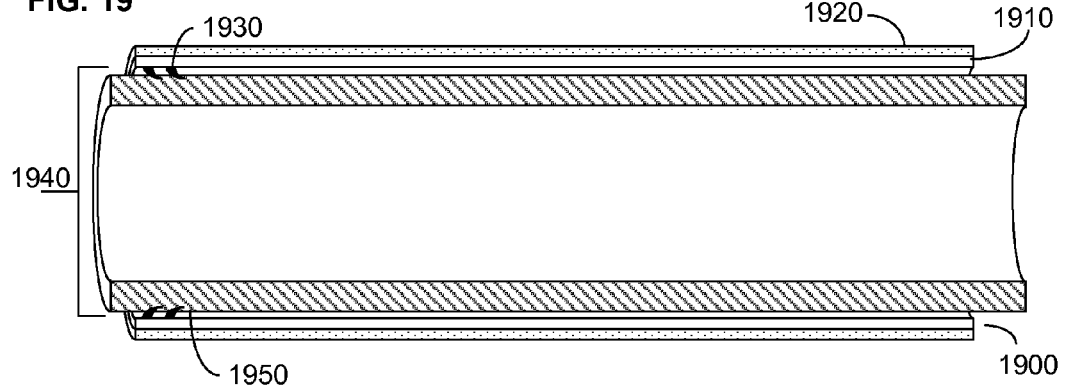
FIG. 19 is a schematic of a longitudinal cross-section through an embodiment of a tubular adjunct for a gastrointestinal device including at least one anchor structure associated with an inner surface.

FIGS. 18 and 19 illustrate aspects of an adjunct for a gastrointestinal device including a tubular substrate attached to a gastrointestinal device with at least one anchor structure. FIG. 18 shows a longitudinal cross-section through an embodiment of an adjunct for a gastrointestinal device including a tubular substrate attached to the inner surface of a gastrointestinal device with at least one anchor structure. Adjunct 1800 includes tubular substrate 1810 including a plurality of at least one type of commensal microbe 1820 on a first surface (inner surface) of tubular substrate 1810 and at least one anchor structure 1830, e.g., at least one barb, associated with the second surface (outer surface) of tubular substrate 1810. At least one anchor structure 1830 of adjunct 1800 is shown engaging the inner surface 1850 of gastrointestinal device 1840.

FIG. 19 shows a longitudinal cross-section through an embodiment of an adjunct for a gastrointestinal device attached to the outer surface of a gastrointestinal device with at least one anchor structure. Adjunct 1900 includes tubular structure 1910 including a plurality of at least one type of commensal microbe 1920 on a first surface (outer surface) of tubular substrate 1910 and at least one anchor structure 1930 associated with the second surface (inner surface) of tubular substrate 1910. At least one anchor structure 1930 of adjunct 1900 is shown engaging the outer surface 1950 of gastrointestinal device 1940.

Figure 20A:
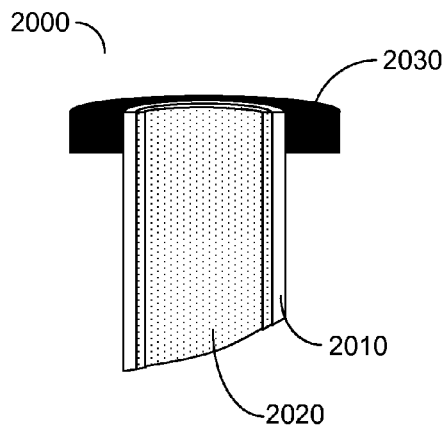
FIG. 20A is a schematic of an embodiment of an anchor structure of an adjunct for a gastrointestinal device.
Figure 20B:
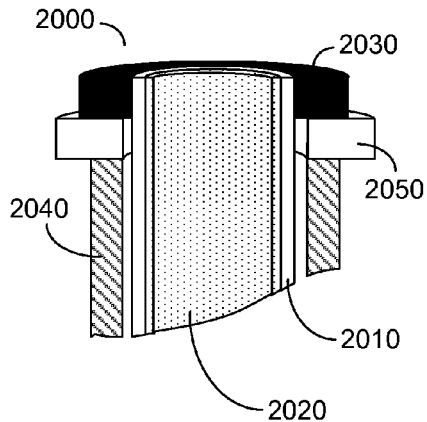
FIG. 20B is a schematic of an embodiment of an adjunct for a gastrointestinal device with an anchor structure positioned relative to the gastrointestinal device.

In an aspect, the at least one anchor structure of an adjunct for a gastrointestinal device includes a structure attached to or integral to a tubular substrate of the adjunct, the structure sized to prevent the tubular substrate from slipping through a lumen of a gastrointestinal device. FIGS. 20A and 20B illustrate aspects of an adjunct for a gastrointestinal device including an anchor structure associated with a tubular substrate. FIG. 20A shows a cross-section through an upper portion of adjunct 2000 including tubular substrate 2010 and a plurality of at least one type of commensal microbe 2020 on the inner surface of substrate 2010. Adjunct 2000 further includes anchor structure 2030. FIG. 20B shows a cross-section through an upper portion of adjunct 2000 engaged with an upper portion of gastrointestinal device 2040. Anchor structure 2030 is sized such that it is not able to pass end structure 2050 (e.g., an anchor structure) of gastrointestinal device 2040.

In an aspect, the at least one anchor structure of the adjunct is configured to interact with an anchor structure of the gastrointestinal device. For example, the anchor structure of the adjunct can rest on or be positioned adjacent to an anchor structure of the gastrointestinal device. In an aspect, the at least one anchor structure of the adjunct is configured to attach to an anchor structure of the gastrointestinal device. For example, the adjunct can include at least one hook, barb, snap, pin, clip, staple, prong, or other structure configured to attach to an anchor structure of the gastrointestinal device.

Figure 21A:
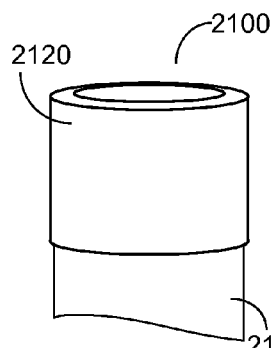
FIG. 21A is a schematic of an embodiment of an inflatable anchor structure of an adjunct for a gastrointestinal device in a first state.
Figure 21B:
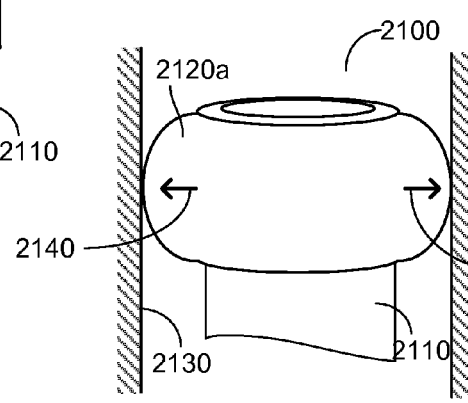
FIG. 21B is a schematic of an embodiment of an inflatable anchor structure of an adjunct for a gastrointestinal device in a second state.
Figure 21C:
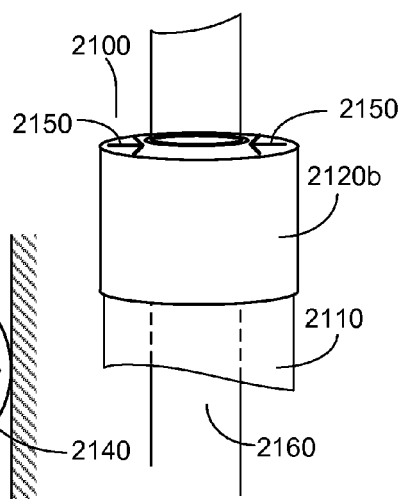
FIG. 21C is a schematic of an embodiment of an inflatable anchor structure of an adjunct for a gastrointestinal device in a third state.

In some embodiments, the at least one anchor structure is inflatable. For example, the adjunct for a gastrointestinal device can include an inflatable anchor structure. FIGS. 21A-21C illustrate non-limiting aspects of an inflatable anchor structure. FIG. 21A shows a portion of adjunct 2100 including substrate 2110 and an inflatable anchor structure 2120. For example, inflatable anchor structure 2120 can include an inflatable balloon or donut-shaped structure which when inflated expands radially to engage a surface of a gastrointestinal device. See, e.g., U.S. Patent Application No. 2014/0012178 to Chin titled "Systems and Methods for Bariatric Therapy," which is incorporated herein by reference. FIG. 21B shows a portion of adjunct 2100 including substrate 2110 and the inflatable anchor structure 2120 of FIG. 21A in an outwardly inflated state 2120a. The inflatable anchor structure has inflated outwardly as designated by arrows 2140. Adjunct 2100 is shown inside the lumen of a gastrointestinal device with the outer edge of the inflatable anchor structure in the outwardly inflated state 2120a touching the inner surface 2130 of the gastrointestinal device. FIG. 21C shows a portion of adjunct 2100 including substrate 2110 and the inflatable anchor structure 2120 of FIG. 21A in an inwardly inflated state 2120b. The inflatable anchor structure has inflated inwardly as designated by arrows 2150. Adjunct 2100 is shown disposed over at least a portion of gastrointestinal device 2160 with the inner edge of the inflatable anchor structure in the inwardly inflated state 2120b touching the outer surface of the gastrointestinal device.

In an aspect, the at least one anchor structure is formed from a thin-walled material. For example, the anchor structure can be formed from an expandable thin sheet of nylon or latex. In an aspect, the at least one anchor structure is formed from a biocompatible material. In an aspect, the at least one anchor structure is formed from a degradable material (e.g., a degradable polymer).

Figure 22A:
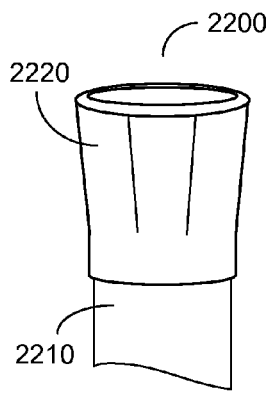
FIG. 22A is a schematic of an embodiment of an expandable anchor structure of an adjunct for a gastrointestinal device in a first state.
Figure 22C:
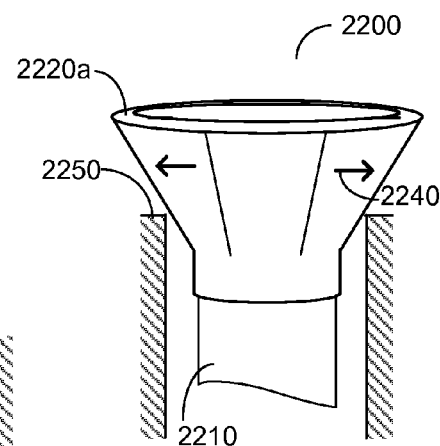
FIG. 22C is a schematic of an embodiment of an expandable anchor structure of an adjunct for a gastrointestinal device in a second state.
Figure 22B:
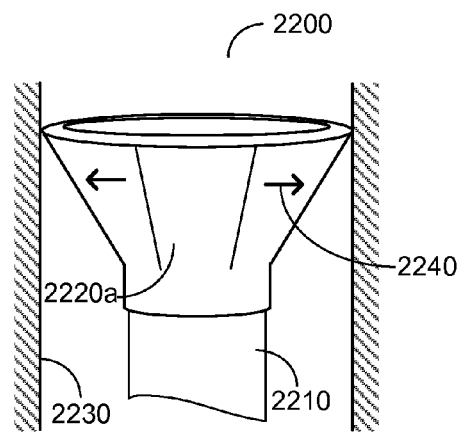
FIG. 22B is a schematic of an embodiment of an expandable anchor structure of an adjunct for a gastrointestinal device in a second state.

In some embodiments, the at least one anchor structure is expandable. For example, the adjunct for a gastrointestinal device can includes an expandable anchor structure. FIGS. 22A-22C illustrate non-limiting aspects of an expandable anchor structure. FIG. 22A shows a portion of adjunct 2200 including substrate 2210 and expandable anchor structure 2220. For example, anchor structure 2220 can include an expandable anchor structure that expands upon placement into a lumen of a gastrointestinal device. FIG. 22B shows a portion of adjunct 2200 including substrate 2210 engaged with an inner surface 2230 of a gastrointestinal device. Adjunct 2200 further includes the expandable anchor structure 2220 of FIG. 22A in an expanded form 2220a, having been expanded radially outward as designated by arrows 2240. The expandable anchor structure in an expanded form 2220a is engaged, e.g., pressing against, the inner surface 2230 of the gastrointestinal device, anchoring adjunct 2200 in place.

In an aspect, an adjunct includes an expandable anchor structure that abuts an end of a gastrointestinal device, e.g., a gastrointestinal sleeve, liner, or stent. FIG. 22C shows a portion of adjunct 2200 including substrate 2210 engaged with an end portion 2250 of a gastrointestinal device. The expandable anchor structure is shown in expanded form 2220a, expanding radially outward as designated by arrows 2240, and proximal to the end portion 2250 of a gastrointestinal device. The expansion of anchor structure 2220a is configured to prevent the adjunct from passing completely through the lumen of the gastrointestinal device.

In an aspect, the at least one anchor structure is a self-expanding. In an aspect, the self-expanding anchor structure includes a self-expanding cone-shaped anchor structure. In an aspect, the self-expanding anchor structure includes two or more arms or wings that spring out radially to engage a surface or end of a gastrointestinal device. See, e.g., U.S. Patent Application No. 2014/0012178 to Chin titled "Systems and Methods for Bariatric Therapy," which is incorporated herein by reference. In an aspect, the self-expanding anchor structure is formed from an elastic polymer or shape-memory alloy. In an aspect, the at least one anchor structure includes a compressible or collapsible anchor which expands upon placement into a lumen of a gastrointestinal device. For example, the at least one anchor structure can include a structure having coils or springs that expand to engage an inner surface of a gastrointestinal device. For example, the at least one anchor structure can include expandable disks or rings that expand to engage an inner surface of a gastrointestinal device. See, e.g., U.S. Patent Application No. 2012/0184893 to Thompson et al. titled "Anchors and Methods for Intestinal Bypass Sleeves," which is incorporated herein by reference. In an aspect, the at least one anchor structure expands to exert a force against the inner surface of the gastrointestinal device, anchoring the adjunct in the gastrointestinal device. See, e.g., U.S. Pat. No. 7,976,488 to Levine & Melanson titled "Gastrointestinal Anchor Compliance," which is incorporated herein by reference.

Figure 23A:
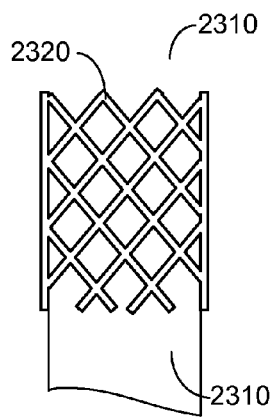
FIG. 23A is a schematic of an embodiment of an expandable anchor structure of an adjunct for a gastrointestinal device in a first state.
Figure 23B:
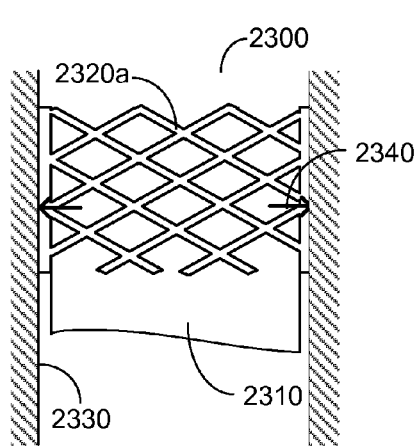
FIG. 23B is a schematic of an embodiment of an expandable anchor structure of an adjunct for a gastrointestinal device in a second state.

In an aspect, the self-expanding anchor structure includes a stent-like anchor structure to which the substrate is attached. See, e.g., U.S. Pat. No. 7,025,791 to Levine et al. titled "Bariatric Sleeve," which is incorporated herein by reference. FIGS. 23A and 23B illustrate aspects of an embodiment of a stent-like anchor structure. FIG. 23A shows a portion of adjunct 2300 including substrate 2310 and stent-like anchor structure 2320. FIG. 23B shows a portion of adjunct 2300 engaged with the inner surface of a gastrointestinal device. Adjunct 2300 includes substrate 2310 and stent-like anchor structure 2320 of FIG. 23A in an expanded state 2320a having expanded radially outward as designated by arrows 2340. Stent-like anchor structure in an expanded state 2320a is shown engaged, e.g., pressed up against, the inner surface 2330 of a gastrointestinal device.

In an aspect, the at least one anchor structure is integral with at least one surface of the substrate, being formed from the same material. In an aspect, the at least one anchor structure is formed independently from the substrate and subsequently coupled to the substrate. In an aspect, the at least one anchor structure is formed independently from the substrate and subsequently coupled to the substrate during or after insertion. For example, the at least one anchor structure can include at least one clip, e.g., an endoscopic clip.

In an aspect, at least a portion of the at least one anchor structure is formed from a shape memory alloy, e.g., nickel titanium alloys (Nitinol). In an aspect, at least a portion of the at least one anchor structure is formed from any of a number of other suitable alloys or metals, non-limiting examples of which include stainless steel alloys (e.g., 304, 316L, BioDur® 108 Alloy, Pyromet® Alloy CTX-909, Pyromet® Alloy CTX-3, Pyromet® Alloy 31, Pyromet® Alloy CTX-1, 21Cr-6Ni-9Mn Stainless, 21Cr-6Ni-9Mn stainless, Pyromet® Alloy 350, 18Cr-2Ni-12Mn Stainless, Custom 630 (17Cr-4Ni) Stainless, Custom 465® Stainless, Custom 455® Stainless, Custom 450® Stainless, Carpenter 13-8 Stainless, Type 440C Stainless, cobalt chromium alloys—MP35N, Elgiloy, L605, Biodur® Carpenter CCM alloy, Titanium and titanium alloys, Ti-6Al-4V/ELI and Ti-6Al-7Nb, Ti-15Mo, Tantalum, Tungsten and tungsten alloys, pure platinum, platinum-iridium alloys, platinum-nickel alloys, niobium, iridium, conichrome, gold and gold alloys.

In an aspect, at least a portion of the at least one anchor structure is formed from an absorbable metal, nonlimiting examples of which include pure iron and magnesium alloys.

In an aspect, at least a portion of the at least one anchor structure is formed from one or more plastics, nonlimiting examples of which include polyetheretherketone (PEEK), polycarbonate, polyolefins, polyethylenes, polyether block amides (PEBAX), nylon 6, 6-6, 12, polypropylene, polyesters, polyurethanes, polytetrafluoroethylene (PTFE), poly(phenylene sulfide) (PPS), poly(butylene terephthalate) PBT, polysulfone, polyamide, polyimide, poly(p-phenylene oxide) PPO, acrylonitrile butadiene styrene (ABS), polystyrene, poly(methyl methacrylate) (PMMA), polyoxymethylene (POM), ethylene vinyl acetate, styrene acrylonitrile resin, or polybutylene.

In an aspect, at least a portion of the at least one anchor structure is formed from an absorbable polymer, non-limiting examples of which include polyglycolic acid (PGA), polylactide (PLA), poly(.epsilon.-caprolactone), poly(dioxanone), or poly(lactide-co-glycolide).

In an aspect, the at least one anchor structure is formed from and/or includes radiopaque and/or sonoreflective materials and/or includes one or more radiopaque and/or sonoreflective markers for enhanced imaging by X-ray, fluoroscopy, and/or ultrasonic imaging so that the position and functional state of the anchor structure can be verified noninvasively. In an aspect, the radiopaque material includes a radiopacifier or a material with a higher electron density compared to the surrounding tissue so that it absorbs X-rays.

In an aspect, the radiopaque material or radiopacifier includes at least one of gold, tungsten, zirconium oxide, barium sulphate, or bismuth. For example, the anchor structure can be formed from a polymer mixed with a radiopaque filler, e.g., barium sulfate, bismuth compounds, or tungsten. In an aspect, the sonoreflective marker includes reflective "beads." For example, the sonoreflective marker can include reflective beads formed from stainless steel, Nitinol, titanium, and the like. See, e.g., U.S. Patent Application No. 2011/0021888 to Sing titled "Apparatus, Systems, and Methods for Localizing Markers or Tissue Structures within a Body," which is incorporated herein by reference. In an aspect, the sonoreflective marker includes a piezoelectric marker that generates electrical signals when scanned by ultrasound. See, e.g., U.S. Pat. No. 8,282,561 to Towe titled "Piezo Micro-markers for Ultrasound Medical Diagnostics," which is incorporated herein by reference.

In an aspect, the adjunct (e.g., a patch, a sheet, or a tubular adjunct) including at least one anchoring structure is attached to the gastrointestinal device prior to insertion of the gastrointestinal device into the gastrointestinal tract. For example, an adjunct configured for attachment to the outer surface of a gastrointestinal device may be attached with one or more hooks or barbs to the outer surface of the gastrointestinal device prior to deploying the device in the gastrointestinal tract. In an aspect, the adjunct is attached to a gastrointestinal device already resident in the gastrointestinal tract. For example, an endoscope or similar type device may be used to deliver a tubular adjunct including an inflatable or expandable anchoring structure to the lumen of a gastrointestinal device and the anchoring structure subsequently inflation or expansion to anchor the tubular adjunct in the gastrointestinal device.

In some embodiments, an adjunct for a gastrointestinal device includes a flexible tubular substrate configured to attach to a gastrointestinal device, the flexible tubular substrate including an inner surface and an outer surface; and a plurality of at least one type commensal microbe associated with at least a portion of at least one the inner surface and the outer surface of the flexible tubular substrate. For example, the flexible tubular substrate can include a sleeve, liner, or stent including the plurality of the at least one type of commensal microbe on at least one surface and configured to attach to a gastrointestinal device. In an aspect, the flexible tubular substrate includes an adhesive on at least one of the inner surface and the outer surface. In an aspect, the flexible tubular substrate includes an adhesive on a surface conforming to a surface of the gastrointestinal device. In an aspect, the flexible tubular substrate includes at least one anchor structure configured to attach the flexible tubular substrate to the gastrointestinal device. For example, the flexible tubular substrate can include at least one hook, barb, snap, pin, clip, staple, or prong. For example, the flexible tubular substrate can include at least one inflatable or expandable anchor structure.

Prebiotic Agents

In an aspect, the adjunct for a gastrointestinal device includes at least one prebiotic agent. In an aspect, the at least one prebiotic agent promotes growth and/or maintenance of the at least one type of commensal microbe associated with the substrate of the adjunct. In an aspect, the at least one prebiotic agents promotes growth and/or maintenance of microbes, e.g., bacteria, resident in the gastrointestinal tract. For example, the at least one type of prebiotic agent can include at least one dietary fiber (e.g., polysaccharide or oligosaccharide) that promotes the growth of at least one type of commensal microbe, e.g., a probiotic, enhancing the beneficial effect of the at least one type of commensal microbe. For example, the at least one prebiotic agent can induce endogenous or administered microbes to generate short chain fatty acids (SCFAs). For example, the at least one prebiotic agent can induce endogenous or administered microbes to excrete an end product inhibitory to pathogenic bacteria. For example, the at least one prebiotic agent can promote a host-mediated attack against tumor sites and/or promote certain strains of *Lactobacillus* that have immune-modulating activity. For example, the at least one prebiotic agent may also affect the production of certain bacterial enzymes, such as decreasing glucosidase that is associated with the absorption of intestinal cholesterol. See, e.g., U.S. Pat. No. 7,101,565 to Monte titled "Probiotic/Prebiotic Composition and Delivery Method," which is incorporated herein by reference.

In an aspect, the at least one prebiotic agent is complimentary to the at least one type of commensal microbe associated with the substrate. In an aspect, the at least one prebiotic agent is incorporated into the substrate, e.g., formulated with the plurality of the at least one type of commensal microbe. In an aspect, the at least one prebiotic agent is administered separately, e.g., as an oral supplement.

In an aspect, the at least one prebiotic agent includes at least one of a mucopolysaccharide, a chitin, a carrageenan, arabinogalactin, a starch polysaccharide, an oligosaccharide, a fructo-oligosaccharide, or inulin. In an aspect, the at least one prebiotic agent includes one or more of an oligosaccharide, a fructo-oligosaccharide (e.g., soy fructo-oligosaccharide, inulin or banana fiber), a pectin or pectic polysaccharide, a mannan (e.g., guar gum, locust bean gum, konjac, or xanthan gum), a pentosan, beta-glucan, arabinan and galactan, such as larch arabinogalactan, and/or mixtures thereof. For example, the at least one prebiotic agent can include a long-chain polysaccharide comprised primarily of fructose monosaccharides (e.g., soy fructo-oligosaccharide, inulin or banana fiber), non-limiting sources of which include honey, beer, onion, asparagus, maple sugar, oats, and Jerusalem artichoke. For example, the at least one prebiotic agent can include pectin and/or pectic polysaccharides including galacturonans or rhamnogalacturonans having various side chains (e.g., D-galactose, L-arabinose, D-xylose, and, less frequently, L-frucose and D-glucuronic acid). For example, the at least one prebiotic agent can include a polysaccharides including neutral pectic polymers such as galactans and arabinans, xyloglucans, and galactomannans. In an aspect, the at least one prebiotic agent includes a non-starch polysaccharide, e.g., an arabinogalactan. Additional non-limiting examples of prebiotic agents are described in U.S. Pat. No. 7,101,565 to Monte titled "Probiotic/Prebiotic Composition and Delivery Method," which is incorporated herein by reference.

In an aspect, the at least one prebiotic agent includes at least one of a protein, a peptide, a lipid, a nutrient, a vitamin, a mineral, or a salt. For example, the at least one prebiotic agent can include a buffering agent to alter a pH of the gastrointestinal tract. For example, the adjunct may include a buffer to neutralize the low pH of the chyme coming from the stomach, e.g., to replace or supplement a neutralizing function that is normally carried out by the bile. For example, the adjunct may include a buffer to alter a pH condition of the gastrointestinal tract to promote growth of commensal bacteria and/or to inhibit growth of pathogenic bacteria.

Other Agents

In an aspect, the adjunct for a gastrointestinal device includes at least one therapeutic agent. In an aspect, the at least one therapeutic agent includes at least one agent of benefit to a gastrointestinal condition. For example, the at least one therapeutic agent can include at least one agent to treat an infection (e.g., bacterial infection), inflammation (e.g., inflammatory bowel disorder), ulcerative colitis, cancer, food sensitivity, muscle contraction, pain, or other condition of the gastrointestinal tract. In an aspect, the at least one therapeutic agent includes at least one antimicrobial agent (e.g., antibiotic, antifungal, antiparasitic, or antiviral agent), anti-inflammatory agent, or chemotherapy agent. In an aspect, the at least one therapeutic agent includes at least one muscle relaxant or anti-spasmodic. In an aspect, the at least one therapeutic agent includes at least one analgesic.

In an aspect, the adjunct for a gastrointestinal device further includes at least one bioactive agent. For example, the at least one bioactive agent can include at least one digestive enzyme or hormone for breaking down ingested products. Non-limiting examples of digestive enzymes and hormones include pepsin, trypsinogen, chymotrypsinogen, carboxypeptidase, pancreatic lipase, sterol esterase, phospholipase, nucleases, sucrose, lactase, maltase, gastrin, somatostatin, secretin, or cholecystokinin.

In an aspect, the adjunct for a gastrointestinal device includes at least one of a prebiotic agent, a therapeutic agent, or a bioactive agent in a coating. For example, the adjunct can include at least one of a prebiotic agent, therapeutic agent, and/or bioactive agent in a coating on the first and/or second surface of the substrate of the adjunct. In an aspect, the adjunct for a gastrointestinal device includes at least one of a prebiotic agent, a therapeutic agent, or a bioactive agent in a degradable coating. In an aspect, the at least one prebiotic agent, therapeutic agent, or bioactive agent is in a degradable matrix. In an aspect, the degradable coating or matrix includes a stimulus-responsive degradable coating or matrix, non-limiting examples of which have been described above herein.

In an aspect, at least one first prebiotic agent, therapeutic agent, and/or bioactive agent is in a first degradable coating and at least one second prebiotic agent, therapeutic agent, and/or bioactive agent is in a second degradable coating. In an aspect, the first degradable coating and the second degradable coating degrade at different rates. For example, an adjunct for a gastrointestinal device may include a first degradable coating including at least one first prebiotic agent, therapeutic agent, and/or bioactive agent that degrades more rapidly than a second degradable coating including at least one second prebiotic agent, therapeutic agent, and/or bioactive agent, releasing the at least one first prebiotic agent, therapeutic agent, and/or bioactive agent more rapidly into the system than the at least one second prebiotic agent, therapeutic agent, and/or bioactive agent.

In an aspect, the plurality of the at least one type of commensal microbe is in a first degradable coating or matrix and at least one of a prebiotic agent, a therapeutic agent, or a bioactive agents is in a second degradable coating or matrix. In an aspect, the first degradable coating or matrix and the second degradable coating or matrix degrade at different rates. Non-limiting examples of degradable coatings and/or matrices have been described above herein.

Gastrointestinal System Including a Gastrointestinal Device and an Adjunct Including a Plurality of at Least One Type of Commensal Microbe A gastrointestinal system including a gastrointestinal device and an adjunct for the gastrointestinal device is described herein. In an aspect, a gastrointestinal system includes a gastrointestinal device; and an adjunct configured to attach to the gastrointestinal device, the adjunct including a substrate, the substrate including a first surface and a second surface and a plurality of at least one type of commensal microbe associated with at least a portion of at least one of the first surface and the second surface of the substrate.

FIGS. 24A and 24B illustrate aspects of a gastrointestinal system. FIG. 24A shows gastrointestinal system 2400 including gastrointestinal device 2410 and adjunct 2420 configured to attach to gastrointestinal device 2410. Adjunct 2420 includes a tubular substrate 2430. Tubular substrate includes an inner and an outer surface, the inner surface including a plurality of at least one type of commensal microbe. In some embodiments, the system can include an adjunct including a tubular substrate with a plurality of at least one type of commensal microbe on an outer surface of the tubular substrate. In an aspect, adjunct 2420 is configured to insert into gastrointestinal device 2410. Adjunct 2420 further includes an anchor structure 2440 configured to attach adjunct 2420 to gastrointestinal device 2410. In some embodiments, the adjunct is configured to attach to gastrointestinal device through an adhesive associated with at least one surface of the substrate. In some embodiments, the adjunct is configured to attach to gastrointestinal device through at least one anchor structure, e.g., at least one hook, barb, prong, or other anchoring structure. Gastrointestinal device 2410 can include a gastrointestinal sleeve, liner, or stent. In the non-limiting example shown in FIG. 24A, gastrointestinal device 2410 includes a sleeve 2450 and an anchoring mechanism 2460.

FIG. 24B illustrates placement of gastrointestinal system 2400 in a gastrointestinal tract 2460. In this non-limiting example, gastrointestinal system 2400 including gastrointestinal device 2410 and adjunct 2420 is positioned in the upper portion of the small intestine. In some embodiments, adjunct 2420 is attached to the inner surface of gastrointestinal device 2410 such that the plurality of the at least one type of commensal microbe can interact with the contents of ingested food or chyme passing through the gastrointestinal device. In some embodiments, the adjunct is attached to the outer surface of gastrointestinal device such that the plurality of the at least one type of commensal microbe can interact with components of the gastrointestinal tract.

Figure 25A:
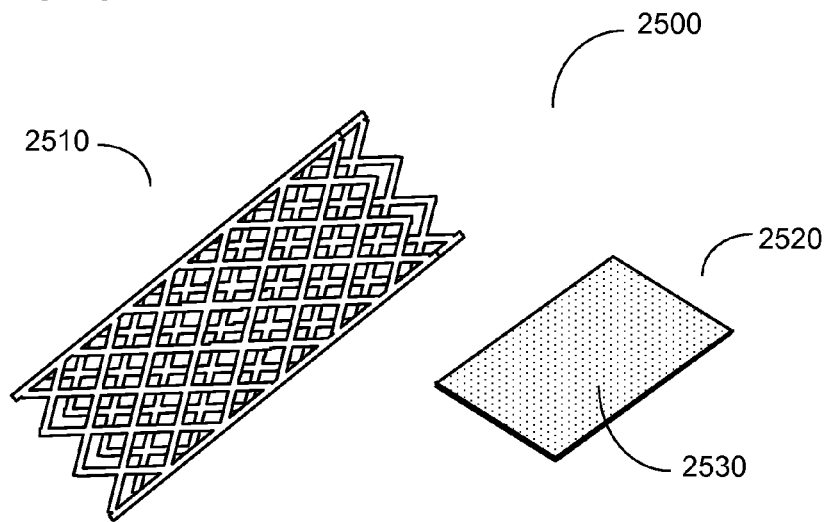
FIG. 25A is a schematic of an embodiment of a gastrointestinal system including a gastrointestinal device and an adjunct for a gastrointestinal device including a plurality of at least one type of commensal microbe.
Figure 25B:
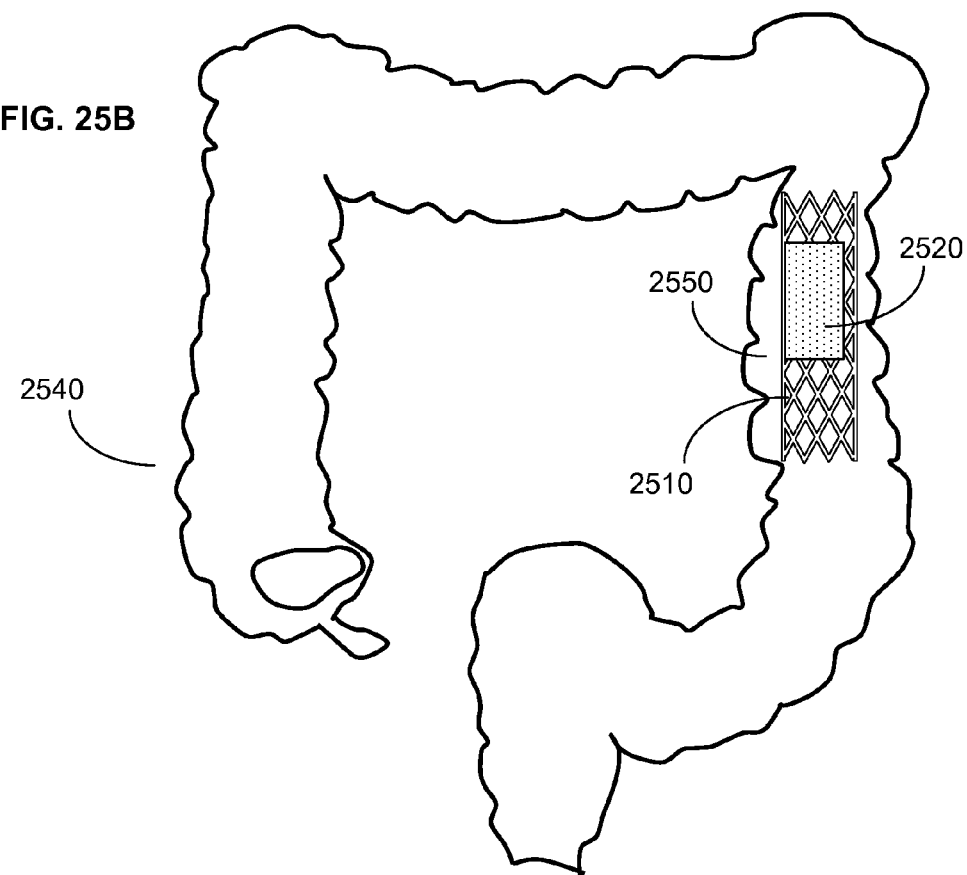
FIG. 25B is a schematic of an embodiment of a gastrointestinal system positioned in a gastrointestinal tract.

FIGS. 25A and 25B illustrate aspects a gastrointestinal system. FIG. 25A shows gastrointestinal system 2500 including gastrointestinal device 2510 and adjunct 2520 configured to attach to gastrointestinal device 2510. Adjunct 2520 includes a substrate (e.g., a patch or a sheet) and a plurality of at least one type of commensal microbe 2530 on at least one surface of the substrate. In some embodiments, adjunct 2520 is configured to attach to gastrointestinal device 2510 through an adhesive associated with at least one surface of the substrate. In some embodiments, adjunct 2520 is configured to attach to gastrointestinal device 2510 through at least one anchor structure, e.g., at least one hook, barb, prong, or other anchoring structure. Gastrointestinal device 2510 can include a gastrointestinal stent.

FIG. 25B illustrates placement of gastrointestinal system 2500 in a gastrointestinal tract 2540. In this non-limiting example, gastrointestinal system 2500 including gastrointestinal device 2510 and adjunct 2520 is positioned in the lower portion of the large intestine. In some embodiments, adjunct 2520 is attached to the inner surface of gastrointestinal device 2510 such that the plurality of the at least one type of commensal microbe can interact with the contents of ingested food or chyme passing through the gastrointestinal device. In some embodiments, adjunct 2520 is attached to the outer surface of gastrointestinal device 2510 such that the plurality of the at least one type of commensal microbe can interact with components of the gastrointestinal tract. In some embodiments, gastrointestinal device 2510 is non-contiguous, e.g., has a mesh-like framework common in stents, such that a surface of the substrate including the plurality of the at least one type of commensal microbe can face a surface of the gastrointestinal device and still allow interaction of the plurality of the at least one type of commensal microbe to interact with either the contents of ingested food or chyme, or components of the gastrointestinal tract.

A gastrointestinal system such as described herein includes a gastrointestinal device. The gastrointestinal device is sized for placement in a portion of the gastrointestinal tract of a subject. It is anticipated that the entirety of the gastrointestinal device will reside within the gastrointestinal tract. In an aspect, the gastrointestinal device is sized for placement in a mouth, an esophagus, a stomach, a pylorus, a duodenum, a jejunum, an ileum, a caecum, an ascending colon, a transverse colon, a descending colon, a sigmoid colon, a rectum, an anus, a gland, a duct, a sphincter, or a combination thereof of the subject. In an aspect, the gastrointestinal system including the gastrointestinal device and the adjunct to the gastrointestinal device replaces or supports a defective or at risk portion of the gastrointestinal tract. In an aspect, the gastrointestinal system including the gastrointestinal device and the adjunct to the gastrointestinal device acts as an artificial gut. For example, the adjunct for a gastrointestinal device can provide a microbial environment in the form of the plurality of the at least one type of commensal microbe that interacts with ingested food or chyme or with the gastrointestinal wall. In an aspect, the adjunct of the gastrointestinal system includes a plurality of at least one type of commensal microbes that replaces the digestive and/or nutritional functions of endogenous microbes that are otherwise covered by a portion of the gastrointestinal device. In an aspect, the plurality of the at least one type of commensal microbe forms a microbiome.

In an aspect, the gastrointestinal device includes a sleeve, a liner, or a stent. For example, the gastrointestinal device can include a sleeve with an anchoring mechanism, the sleeve configured to extend into the gastrointestinal tract. Non-limiting examples of gastrointestinal devices including a sleeve are described in U.S. Pat. No. 7,037,344 to Kagan et al. titled "Apparatus and Methods for Treatment of Morbid Obesity;" U.S. Patent Application No. 2013/0331759 from Neisz et al. titled "Device and Methods for Gastrointestinal Bypass;" and U.S. Patent Application No. 2014/0012178 from Chin titled "System and Methods for Bariatric Therapy," which are incorporated herein by reference. In an aspect, the gastrointestinal device includes a gastrointestinal liner. For example, the gastrointestinal device can include an implantable gastrointestinal liner, for example, a duodenal-jejunal bypass liner. A non-limiting example of a duodenal-jejunal bypass liner is described in Escalona et al. (2012) "Weight Loss and Metabolic Improvement in Morbidly Obese Subjects Implanted for 1 Year with an Endoscopic Duodenal-Jejunal Bypass Liner," *Ann. Surg.* 255:1080-1085, which is incorporated herein by reference. For example, the method can include using a commercially available intestinal sleeve, e.g., the EndoBarrier® gastrointestinal liner from GI Dynamics, Inc., Lexington, Mass. See, e.g., Rohde et al. (2013) *BMJ Open* 3:e003417, which is incorporated herein by reference. In an aspect, the gastrointestinal device includes a gastrointestinal stent. For example, the gastrointestinal device can include an esophageal stent, a biliary stent, a gastric stent, a enteral stent, and/or a colorectal stent. Non-limiting examples of gastrointestinal stents are described in Loch & Kahaleh (2007) "Stents for Gastrointestinal Tract and Nutritional Implications," *Practical Gastroenterology* January 2007: 48-57; and Lam-Tsai et al. (2011) "A Review of Gastrointestinal Stenting," *Gastroenterology & Endoscopy News*, June 2011: 1-8, which are incorporated herein by reference. Also see, e.g., U.S. Pat. No. 7,025,791 to Levine et al. titled "Bariatric Sleeve;" U.S. Pat. No. 7,976,488 to Levine & Melanson titled "Gastrointestinal Anchor Compliance;" U.S. Patent Application No. 2012/0158026 to Behan titled "Gastrointestinal Implant Device;" U.S. Patent Application No. 2021/0184893 to Thompson et al. titled "Anchors and Methods for Intestinal Bypass Sleeves;" U.S. Patent Application No. 2013/0281911 to Babkes et al. titled "Anchored Non-Piercing Duodenal Sleeve and Delivery Systems;" which are incorporated herein by reference.

In an aspect, the gastrointestinal device is of a type configured for treating a medical condition of a subject. For example, the gastrointestinal device can be of a type configured for treating diabetes, obesity, metabolic syndrome, colitis, cancer, ischemia, inflammatory bowel disease, irritable bowel syndrome, an autoimmune disorder, trauma, stricture, or a microbial infection.

A gastrointestinal system such as described herein includes an adjunct. In an aspect, the adjunct includes a patch. In an aspect, the adjunct includes a sheet. In an aspect, the adjunct includes a tubular structure. In an aspect, the adjunct is flexible. In an aspect, the adjunct includes a flexible tubular structure. In an aspect, the adjunct includes a substrate that includes a patch, sheet, or tubular structure. In an aspect, the adjunct includes a substrate that includes a flexible patch, sheet, or tubular structure.

The adjunct of the gastrointestinal system is configured to attach to the gastrointestinal device. In an aspect, the adjunct includes an adhesive on a surface of the substrate. In an aspect, the adhesive is on a surface of the substrate conforming to a surface of the gastrointestinal device. For example, the substrate of the adjunct can include glue, epoxy, sealant, mucilage, paste, or other adhesive or binder material. For example, the substrate of the adjunct can include a pressure sensitive adhesive, e.g., a styrene copolymer pressure-sensitive adhesive. Non-limiting examples adhesives have been described above herein.

In an aspect, the adjunct includes at least one anchor structure configured to attach to the gastrointestinal device. In an aspect, the at least one anchor structure is associated with at least one of a proximal end and a distal end of the adjunct. In an aspect, the at least one anchor structure is incorporated into the adjunct. In an aspect, the at least one anchor structure includes at least one hook, barb, snap, pin, clip, staple, or prong. In an aspect, the at least one anchor structure is inflatable. In an aspect, the at least one anchor structure is expandable. Non-limiting examples of anchor structures associated with adjunct for a gastrointestinal device have been described above herein.

In an aspect, the adjunct is configured to attach to an inner surface of the gastrointestinal device. For example, the adjunct can be configured to attach to an inner surface of a gastrointestinal sleeve, liner, or stent, allowing the plurality of the at least one type of commensal microbe associated with the adjunct to come in contact with the contents of ingested food or chyme transiting through the gastrointestinal sleeve, liner, or stent. In an aspect, the adjunct is configured to attach to an outer surface of the gastrointestinal device. For example, the adjunct can be configured to attach to an outer surface of a gastrointestinal sleeve, liner, or stent, allowing the plurality of the at least one type of commensal microbe associated with the adjunct to come in contact with components of the gastrointestinal tract.

In an embodiment, a gastrointestinal system includes a gastrointestinal device and an adjunct for the gastrointestinal device including a layered wall, the plurality of the at least one type of commensal microbe encased in the layered wall. For example, the gastrointestinal system can include a gastrointestinal device (e.g., a sleeve, liner, or stent) and an adjunct for the gastrointestinal device including a substrate (e.g., a patch, sheet, or tubular structure) having a layered wall encasing a plurality of at one type of commensal microbe. In an aspect, the substrate of the adjunct includes a layered wall, the substrate including the plurality of the at least one type of commensal microbe encased in the layered wall. In an aspect, the layered wall of the substrate of the adjunct includes a first layer, a second layer, and an internal space, the internal space disposed between the first layer and the second layer and including the plurality of the at least one type of commensal microbe. Non-limiting aspects of an adjunct for a gastrointestinal device including a layered wall have been described above herein.

Figure 26A:
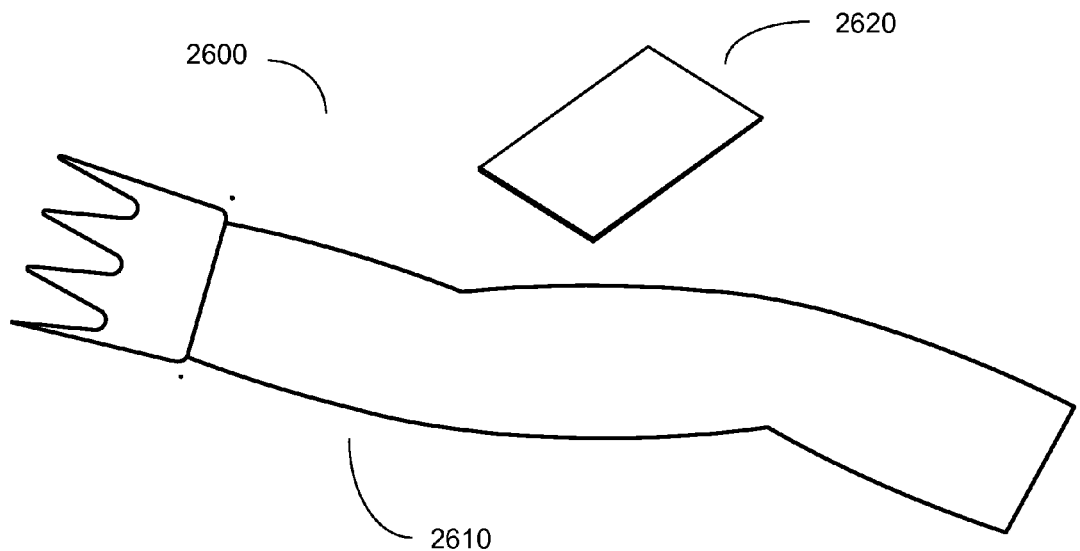
FIG. 26A is a schematic of an embodiment of a gastrointestinal system including a gastrointestinal device and an adjunct for a gastrointestinal device including a plurality of at least one type of commensal microbe in a layered wall.
Figure 26B:
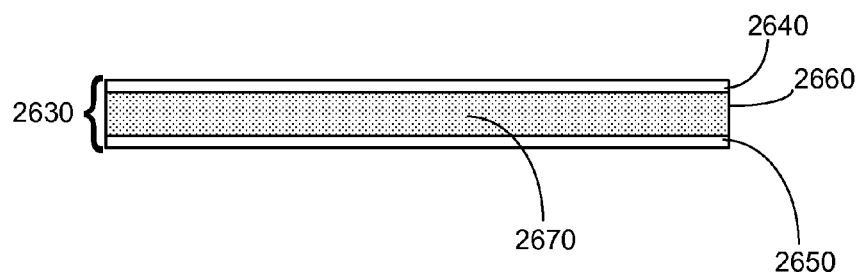
FIG. 26B is a schematic of an adjunct for a gastrointestinal device including a plurality of at least one type of commensal microbe associated with layered wall.
Figure 26C:
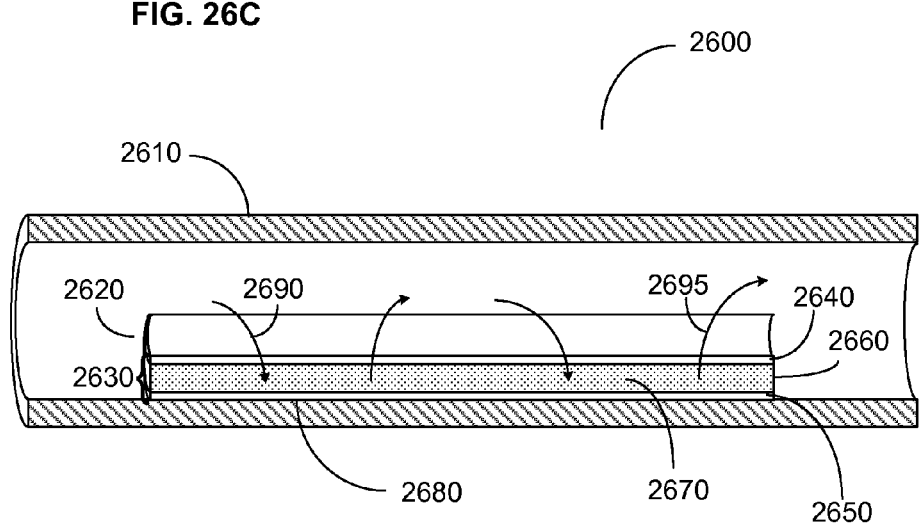
FIG. 26C is a schematic of a system including a gastrointestinal device and an adjunct for a gastrointestinal device including a plurality of at least one type of commensal microbe associated with layered wall.

FIGS. 26A-26C illustrate aspects of an embodiment of a gastrointestinal system including a gastrointestinal device and an adjunct for the gastrointestinal device including a layered wall. FIG. 26A shows gastrointestinal system 2600 including gastrointestinal device 2610 (e.g., a gastrointestinal sleeve or liner) and adjunct 2620. In this non-limiting example, adjunct 2620 includes a substrate (e.g., a patch or sheet), substrate including a layered wall, the plurality of the at least one type of commensal microbe encased in the layered wall. At least one surface of adjunct 2620 includes an adhesive and/or at least one anchor structure configured to attach the at least one surface to a surface of gastrointestinal device 2610. In some embodiments, the gastrointestinal system includes an adjunct having a tubular substrate including a layered wall that attaches to and at least partially covers an inner or an outer surface of the gastrointestinal device. A non-limiting example is shown in FIG. 13B. FIG. 26B shows a longitudinal cross-section through substrate 2630 of adjunct 2620. Substrate 2630 can include a patch, a sheet, or a tubular substrate. Substrate 2630 includes a first layer 2640, a second layer 2650, and internal space 2660. Internal space 2660 is disposed between first layer 2640 and second layer 2650 and includes a plurality of at least one type of commensal microbe 2670 (stippled pattern). In an aspect, at least one of the first layer and the second layer of the layered wall is formed from a semi-permeable material. FIG. 26C shows a longitudinal cross-section through a portion of gastrointestinal system 2600 including adjunct 2620 attached to an inner surface 2680 of gastrointestinal device 2610. In some embodiments, adjunct 2620 includes an adhesive for attaching to gastrointestinal device 2610. In some embodiments, adjunct 2620 includes at least one anchoring structure for attaching to gastrointestinal device 2610. Adjunct 2620 includes substrate 2630 including a layered wall with a first layer 2640, a second layer 2650, internal space 2660, and a plurality of at least one type of commensal microbe 2670. First layer 2640 of adjunct 2620 is further formed from a semi-permeable material, allowing for material to transit in (arrows 2690) and transit out (arrows 2695) the portion of the layered section including the plurality of the at least one type of commensal microbe 2670. For example, ingested components can transit in to interact with the plurality of the at least one type of commensal microbe and/or components secreted by the plurality of the at least one type of commensal microbe can transit out to interact with the ingested components. In some embodiments, at least a portion of the at least one type of commensal microbe are able to transit through the semi-permeable material of the substrate.

In an embodiment, a gastrointestinal system includes a gastrointestinal device and an adjunct for a gastrointestinal device configured to attach to at least a portion of the gastrointestinal device to form a layered section, the adjunct including a substrate, the substrate including a plurality of at least one type of commensal microbe associated with a surface of the substrate, the surface of the substrate including the plurality of the at least one type of commensal microbe configured to face a surface of the gastrointestinal device to form the layered section. In an aspect, the first surface or the second surface of the substrate includes the plurality of the at least one type of commensal microbe configured to face a surface of the gastrointestinal device to form the layered section, wherein the layered section is configured to allow an interaction between the plurality of the at least one type of commensal microbe and the gastrointestinal tract of a subject. For example, the adjunct can include a substrate formed from a semi-permeable material, the plurality of the at least one type of commensal microbe coating a first surface of the substrate, the first surface affixed to a surface of the gastrointestinal device to form a layered section.

Figure 27A:
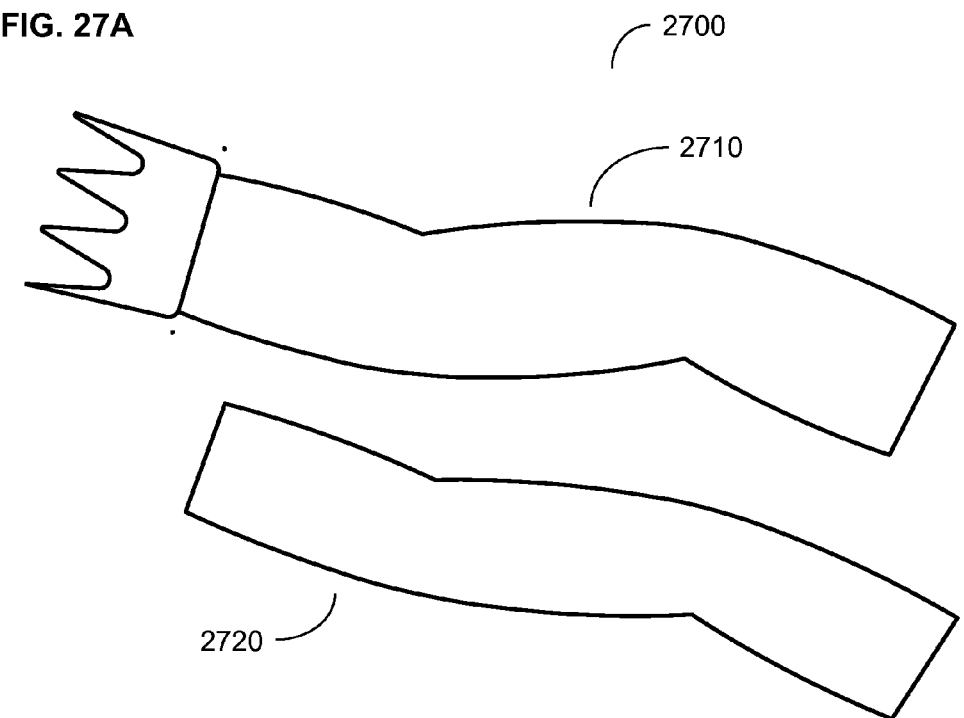
FIG. 27A is a schematic of an embodiment of a gastrointestinal system including a gastrointestinal device and a tubular adjunct for a gastrointestinal device including a plurality of at least one type of commensal microbe.
Figure 27B:
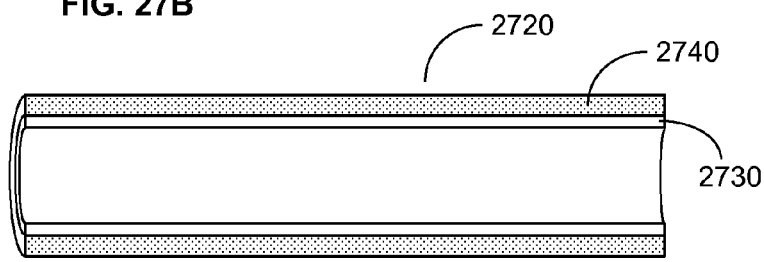
FIG. 27B is a longitudinal cross-section through an embodiment of a tubular adjunct for a gastrointestinal device including a plurality of at least one type of commensal microbe.
Figure 27C:
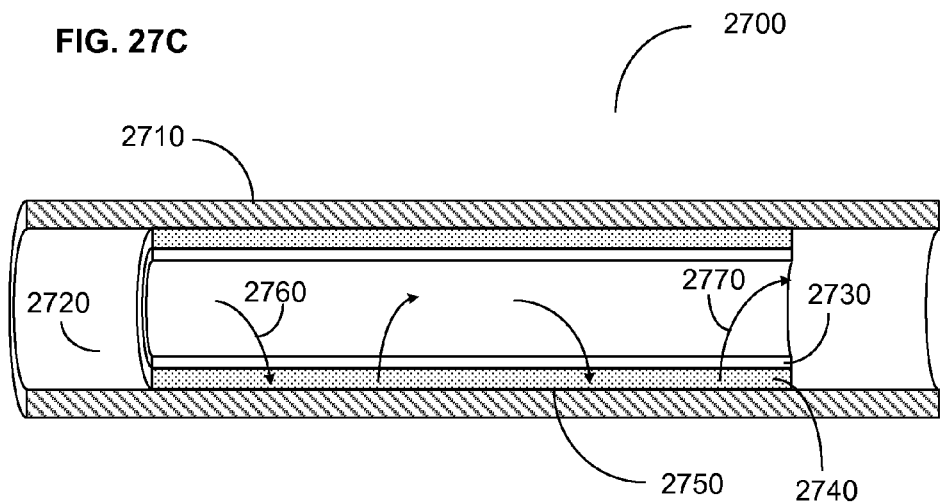
FIG. 27C is a longitudinal cross-section through an embodiment of a gastrointestinal system including a gastrointestinal device and a tubular adjunct for a gastrointestinal device including a plurality of at least one type of commensal microbe associated with a layered section.

FIGS. 27A-27C illustrate aspects of an embodiment of a gastrointestinal system including a gastrointestinal device and an adjunct for the gastrointestinal device configured to form a layered section. FIG. 27A shows gastrointestinal system 2700 including gastrointestinal device 2710 (e.g., a gastrointestinal sleeve or liner) and adjunct 2720 (e.g., a tubular adjunct). Adjunct 2720 includes a tubular substrate and a plurality of at least one type of commensal microbe associated with at least one surface of the substrate. At least one surface of adjunct 2720 including the plurality of the at least one type of commensal microbe further includes an adhesive and/or at least one anchor structure configured to attach the at least one surface to a surface of gastrointestinal device 2710. FIG. 27B shows a longitudinal cross-section through a portion of adjunct 2720. Adjunct 2720 includes substrate 2730 (e.g., a tubular substrate) and a plurality of at least one type of commensal microbe 2740 (stippled pattern) associated with the outer surface of substrate 2730. FIG. 27C shows a longitudinal cross-section through a portion of gastrointestinal system 2700 including adjunct 2720 attached to an inner surface 2750 of a portion of gastrointestinal device 2710. In an aspect, adjunct 2720 is attached to gastrointestinal device 2710 with an adhesive. In an aspect, adjunct 2720 is attached to gastrointestinal device 2710 with at least one anchoring structure. Adjunct 2720 includes substrate 2730 and a plurality of at least one type of commensal microbe 2740 associated with a surface (in this example, an outer surface) of substrate 2730. Adjunct 2720 is attached to gastrointestinal device 2710 such that the inner surface of the gastrointestinal device 2710 and substrate 2730 form a layered section, the layered section including the plurality of the at least one type of commensal microbe 2740 disposed between the inner surface 2750 of gastrointestinal device 2710 and substrate 2730. Substrate 2730 is further formed from a semi-permeable material, allowing for material to transit in (arrows 2760) and transit out (arrows 2770) the portion of the layered section including the plurality of the at least one type of commensal microbe 2740. For example, ingested components can transit in to interact with the plurality of the at least one type of commensal microbe and/or components secreted by the plurality of the at least one type of commensal microbe can transit out to interact with the ingested components. In some embodiments, at least a portion of the at least one type of commensal microbe are able to transit through the semi-permeable material of the substrate.

The adjunct of the gastrointestinal system includes a substrate. In an aspect, the substrate includes a patch, sheet, or tubular structure. In an aspect, the substrate includes a flexible patch sheet, or tubular structure. In an aspect, at least a portion of the substrate of the adjunct is formed from a semi-permeable material. In an aspect, at least a portion of the substrate of the adjunct is formed from a substantially impermeable material.

In an aspect, at least a portion of the adjunct includes a degradable material. In an aspect, at least a portion of the adjunct includes a stimulus-responsive degradable material. In an aspect, the stimulus-responsive degradable material includes at least one of a time-responsive degradable material, a moisture-responsive degradable material, a temperature-sensitive degradable material, a pH-responsive degradable material, or a chemical-responsive degradable material. Non-limiting examples of stimulus-responsive materials have been described above herein. In an aspect, the adjunct is non-contiguous. For example, the adjunct can include segments, e.g., segments connected by degradable portions.

The adjunct of the gastrointestinal system further includes a plurality of at least one type of commensal microbe. In an aspect, the plurality of the at least one type of commensal microbe includes a plurality of at least one type of gut microbe. In an aspect, the plurality of the at least one type of commensal microbe includes a plurality of at least one type of genetically modified microbe. In an aspect, the at least one type of commensal microbe includes at least one type of commensal microbe from a fecal sample. In an aspect, the at least one type of commensal microbe includes at least part of a gut microbiota. For example, the at least part of the gut microbiota can include at least part of a healthy gut microbiota, a preferred gut microbiota, or a theoretical gut microbiota. For example, the at least part of the gut microbiota can be derived from a fecal sample. For example, the at least part of the gut microbiota can be derived from in vitro culture of one or more types of commensal microbes. In an aspect, the plurality of the at least one type of commensal microbe forms a microbiome. Non-limiting examples of commensal microbes have been described above herein.

In an aspect, the plurality of the at least one type of commensal microbe forms a coating on the at least a portion of the at least one of the first surface and the second surface of the substrate of the adjunct. In an aspect, the plurality of the at least one type of commensal microbe includes a plurality of at least one first type of commensal microbe one at least one first portion of the substrate of the adjunct and a plurality of at least one second type of commensal microbe on at least one second portion of the substrate of the adjunct. In an aspect, the plurality of the at least one first type of commensal microbe and the plurality of the at least one second type of commensal microbe form a gradient on the substrate of the adjunct. In an aspect, the plurality of the at least one type of commensal microbe forms a gradient on the at least a portion of the at least one of the first surface and the second surface of the substrate of the adjunct. Non-limiting examples of the plurality of the at least one type of commensal microbe associated with the substrate of an adjunct for a gastrointestinal device have been described above herein.

In an aspect, the at least one type of commensal microbe is beneficial to a subject. In an aspect, the at least one type of commensal microbe is beneficial to the immune system of a subject. In an aspect, the at least one type of commensal microbe is beneficial to a dietary condition of a subject. For example, a dietary condition can include at least one of dietary need, weight control, or food sensitivity. In an aspect, the at least one type of commensal microbe is beneficial to a medical condition of a subject. For example, the medical condition can include diabetes, metabolic syndrome, obesity, cancer, colitis, inflammatory bowel disease, irritable bowel syndrome, ischemia, autoimmune disorder, microbial infection, or microbial deficit.

In an aspect, the plurality of the at least one type of commensal microbe includes at least one probiotic. In an aspect, the plurality of the at least one type of commensal microbe includes at least one type of *Bifodobacterium*. In an aspect, the plurality of the at least one type of commensal microbe includes at least one type of *Bacteroides*. In an aspect, the plurality of the at least one type of commensal microbe includes at least one type of *Lactobacillus*. Non-limiting examples of commensal microbe have been described above herein.

In an aspect, the plurality of the at least one type of commensal microbe is bound to the at least a portion of the at least one of the first surface and the second surface of the substrate of the adjunct. In an aspect, at least one of the plurality of the at least one type of commensal microbe is bound through a selective binding agent (e.g., antibody, oligonucleotide, aptamer, ligand, or receptor) to the at least a portion of the at least one of the first surface and the second surface of the substrate of the adjunct. In an aspect, at least one of the plurality of the at least one type of commensal microbe is bound through a non-selective binding agent to the at least a portion of the at least one of the first surface and the second surface of the substrate of the adjunct.

In an aspect, the plurality of the at least one type of commensal microbe is incorporated into a coating on the at least a portion of the at least one of the first surface and the second surface of the substrate of the adjunct. In an aspect, the plurality of the at least one type of commensal microbe is incorporated into a degradable coating on at least a portion of the at least one of the first surface and the second surface of the substrate of the adjunct. In an aspect, the plurality of the at least one type of commensal microbe is incorporated into a stimulus-responsive degradable coating on the at least a portion of the at least one of the first surface and the second surface of the substrate of the adjunct. For example, the stimulus-responsive degradable coating can include at least one of a time-responsive degradable coating, a moisture-responsive degradable coating, a temperature-responsive degradable coating, a pH-responsive degradable coating, or a chemical-responsive degradable coating. In an aspect, the adjunct of the gastrointestinal system further includes a plurality of at least one first type of commensal microbe in a first degradable coating and a plurality of at least one second type of commensal microbe in a second degradable coating. In an aspect, the first degradable coating and the second degradable coating degrade at different rates.

In some embodiments, the gastrointestinal system further includes at least one prebiotic agent. In an aspect, the at least one prebiotic agent is associated with the gastrointestinal device and/or the adjunct for the gastrointestinal device. Non-limiting examples of prebiotic agents have been described above herein.

In some embodiments, the gastrointestinal system further includes at least one therapeutic agent. In an aspect, the at least one therapeutic agent is associated with the gastrointestinal device and/or the adjunct for the gastrointestinal device. Non-limiting examples of therapeutic agents have been described above herein.

In some embodiments, the gastrointestinal system further includes at least one bioactive agent. In an aspect, the at least one bioactive agent is associated with the gastrointestinal device and/or the adjunct for the gastrointestinal device. Non-limiting examples of bioactive agents have been described above herein.

In an aspect, the gastrointestinal system includes at least one of a prebiotic agent, a therapeutic agent, or a bioactive agent associated with the adjunct. In an aspect, the gastrointestinal system includes at least one of a prebiotic agent, a therapeutic agent, or a bioactive agent incorporated into a degradable coating associated with the adjunct.

In an aspect, the adjunct of the gastrointestinal system includes the plurality of the at least one type of commensal microbe in a first degradable coating and at least one of a prebiotic agent, a therapeutic agent, or a bioactive agent in a second degradable coating. In an aspect, the first degradable coating and the second degradable coating degrade at different rates.

In an aspect, the gastrointestinal device of the gastrointestinal system is sufficiently flexible to be moved through the bends of the gastrointestinal tract without damaging, e.g., perforating, the gastrointestinal wall. For example, the gastrointestinal device is flexible enough to be placed deep within the gastrointestinal tract using a catheter, endoscope, or enteroscope-like device. For example, the gastrointestinal device is flexible enough to be moved through the gastrointestinal tract attached to a device designed to travel through the lumen of the gastrointestinal tract. See, e.g., U.S. Pat. No. 7,998,060 to Ferren et al. titled "Lumen-traveling delivery device," which is incorporated herein by reference. For example, the gastrointestinal device is flexible enough to be moved through the gastrointestinal tract using an endoscope.

In an aspect, the adjunct is attached to the gastrointestinal device prior to placing the gastrointestinal device in the gastrointestinal tract of a subject. For example, an adjunct including an adhesive on at least one surface can be adhered to a surface, e.g., an inner or outer surface, of a gastrointestinal device prior to placement. For example, an adjunct including at least one of an anchor structure (e.g., at least one hook, barb, prong, or the like) can be attached to the gastrointestinal device using the at least one anchor structure. For example, an adjunct can be hooked, clipped, sewn, stapled, or adhered to the gastrointestinal device prior to placement.

In an aspect, the adjunct is attached to a gastrointestinal device that is already resident in the gastrointestinal tract of a subject. For example, the adjunct can be placed using a catheter, endoscope or enteroscope-like device. For example, the adjunct can be placed using a lumen-traveling device. For example, the adjunct including an inflatable or expandable anchor structure can be positioned relative to the gastrointestinal device and the anchor structure inflated or expanded to fix the adjunct in place. For example, the adjunct can be hooked, clipped, sewn, stapled, or adhered to a gastrointestinal device resident in the gastrointestinal tract of a subject.

Gastrointestinal Device Including at Least One Microbe-Promoting Agent

An embodiment of an adjunct for a gastrointestinal device is described herein. In an aspect, an adjunct for a gastrointestinal device includes a substrate configured to attach to a gastrointestinal device, the substrate including a first surface and a second surface, and at least one microbe-promoting agent associated with at least one of the first surface and the second surface of the substrate, the at least one microbe-promoting agent configured to promote at least one of attraction, colonization, and growth of at least one type of commensal microbe.

In an aspect, the adjunct of a gastrointestinal device includes a substrate including at least one microbe-promoting agent. In an aspect, the substrate includes a patch. In an aspect, the substrate includes a sheet. In an aspect, the substrate includes a tubular structure. In an aspect, the substrate is flexible. In an aspect, the substrate of the adjunct includes a flexible structure. For example, the substrate of the adjunct can include a flexible structure that conforms in shape to a surface of a gastrointestinal device. For example, the substrate of the adjunct can include a flexible patch or a flexible sheet configured to conform in shape to a surface of a gastrointestinal device. In an aspect, the substrate includes a flexible tubular structure. In an aspect, the substrate is sized to attach to a gastrointestinal sleeve, a gastrointestinal liner, or a gastrointestinal stent. For example, a substrate of an adjunct for a gastrointestinal device including at least one microbe-promoting agent can be sized to attach to an inner or outer surface of a commercially available gastrointestinal device, e.g., a gastrointestinal sleeve or stent. In an aspect, the substrate is sized to attach to a gastrointestinal sleeve, liner, or stent along the full length of the gastrointestinal device or any portion thereof. In an aspect, the substrate is sized to fully match the width of a gastrointestinal device. In an aspect, the substrate is noncontiguous along at least a portion of the length and/or width of the gastrointestinal device.

In an aspect, the substrate of an adjunct for a gastrointestinal device including at least one microbe-promoting agent is sized to attach to a gastrointestinal device of a type configured for treating a medical condition of a subject. For example, the substrate of an adjunct for a gastrointestinal device including at least one microbe-promoting agent can be sized to attach to a gastrointestinal device of a type configured to treat diabetes, obesity, metabolic syndrome, colitis, cancer, ischemia, inflammatory bowel disease, irritable bowel syndrome, an autoimmune disorder, trauma, stricture, or a microbial infection.

Figure 28:
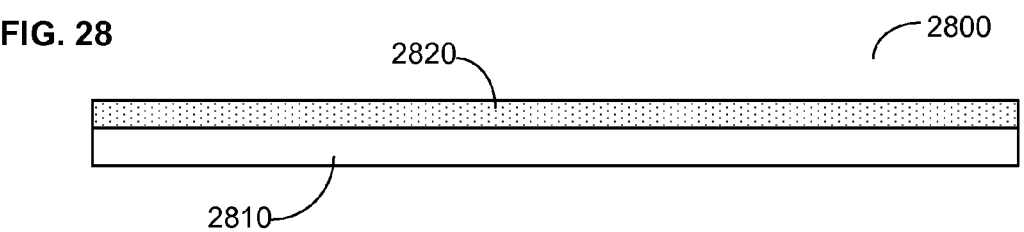
FIG. 28 is a schematic of a longitudinal cross-section through an embodiment of an adjunct for a gastrointestinal device including at least one microbe-promoting agent.

FIGS. 28-33 illustrate aspects of a substrate of an adjunct for a gastrointestinal device including at least one microbe-promoting agent associated with at least one of the first surface and the second surface of the substrate. FIG. 28 shows a longitudinal cross-section through an embodiment of an adjunct for a gastrointestinal device. Adjunct 2800 includes a substrate 2810 and at least one type of microbe-promoting agent 2820 (shown as a stippled pattern) associated with a surface of substrate 2810.

In an embodiment, substrate 2810 includes a patch. For example, the substrate of the adjunct can include a flat structure of an appropriate size to attach to an inner or outer surface of a gastrointestinal device. In an aspect, the patch is square. In an aspect, the patch is rectangular. In an aspect, the patch is circular. The patch can be formed in shapes including, but not limited to, ovoid, triangular, polygonal, trapezoidal, multisided, or any other shape appropriately sized to attach to an inner or outer surface of a gastrointestinal device. In an aspect, the substrate of the adjunct is flexible, e.g., a flexible patch. In an aspect, the at least one microbe-promoting agent is associated with the first surface and/or the second surface of a patch.

In an embodiment, substrate 2810 includes a sheet. In an aspect, the substrate of the adjunct for a gastrointestinal device includes a flexible sheet. For example, the substrate of the adjunct for a gastrointestinal device can include a sheet configured to wrap around the outside of a gastrointestinal device. For example, the substrate of the adjunct for a gastrointestinal device can include a sheet configured to wrap around the inside of a gastrointestinal device, e.g., the inside of a gastrointestinal sleeve or liner. In an aspect, the at least one microbe-promoting agent is associated with the first surface and/or the second surface of a sheet.

In some embodiments of an adjunct for a gastrointestinal device, the at least one microbe-promoting agent is uniformly distributed along at least a portion of at least one of the first surface and the second surface of the substrate. In some embodiments of an adjunct for a gastrointestinal device, the at least one microbe-promoting agent is associated with one or more portions of the surface of the substrate. In an aspect, the at least one microbe-promoting agent forms a pattern on the surface of the substrate of the adjunct.

Figure 29:
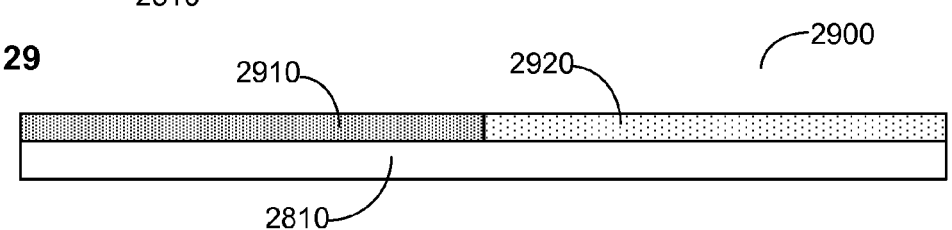
FIG. 29 is a schematic of a longitudinal cross-section through an embodiment of an adjunct for a gastrointestinal device including at least one microbe-promoting agent.

In an aspect, at least a portion of at least one of the first surface and the second surface of the substrate includes two or more microbe-promoting agents. In an aspect, the substrate of the adjunct includes at least one first microbe-promoting agent on a first portion of the substrate and at least one second microbe-promoting agent on a second portion of the substrate. FIG. 29 shows a longitudinal cross-section through an embodiment of an adjunct for a gastrointestinal device. Adjunct 2900 includes substrate 2810 and at least one first microbe-promoting agent 2910 (shown as a first stippled pattern) associated with at least one first portion of the substrate 2810 and at least one second microbe-promoting agent 2920 (shown as a second stippled pattern) associated with at least one second portion of the substrate 2810. For example, the adjunct can include a first microbe-promoting agent associated with at least one first portion of the substrate and a second microbe-promoting agent associated with at least one second portion of the substrate. For example, the adjunct can include a first mix of two or more microbe-promoting agents on at least one first portion of the substrate and a second mix of two or more microbe-promoting agents on at least one second portion of the substrate.

Figure 30:
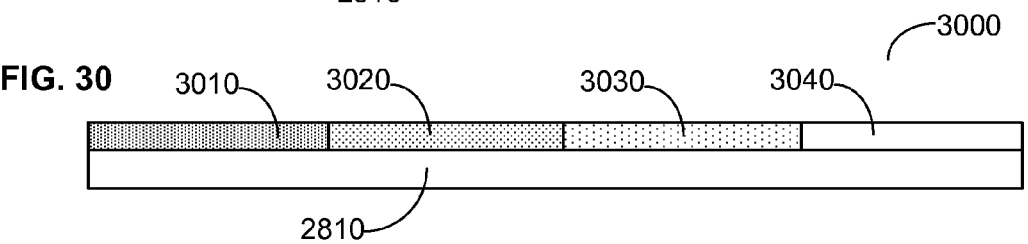
FIG. 30 is a schematic of a longitudinal cross-section through an embodiment of an adjunct for a gastrointestinal device including at least one microbe-promoting agent.

In an aspect, the at least one microbe-promoting agent forms a gradient on at least a portion of at least one of the first surface and the second surface of the substrate. For example, the at least one microbe-promoting agent can be distributed in a gradient along the length of at least a portion of the first surface and/or the second surface of the substrate. For example, the concentration of the at least one microbe-promoting agent can be greater at the proximal end of the substrate than at the distal end of the substrate. For example, the concentration of the at least one microbe-promoting agent can be greater at the distal end of the substrate than at the proximal end of the substrate. FIG. 30 shows a longitudinal cross-section through an embodiment of an adjunct for a gastrointestinal device. Adjunct 3000 includes substrate 2810 and a gradient of the at least one microbe-promoting agent. For example, substrate 2810 includes the at least one microbe-promoting agent at a first concentration 3010 (shown as a first stippled pattern), at a second concentration 3020 (shown as a second stippled pattern), at a third concentration 3030 (shown as a third stippled pattern), and a fourth concentration 3040. In an aspect, the adjunct can include a gradient of a microbe-promoting agent. In an aspect, the adjunct can include a gradient of two or more microbe-promoting agents. In an aspect, the adjunct can include two or more gradients of at least one microbe-promoting agent associated with the substrate. For example, the adjunct can include a first gradient including at least one first microbe-promoting agent and a second gradient including at least one second microbe-promoting agent. For example, the at least one first microbe-promoting agent forms a gradient from high to low concentration from the proximal end to the distal end of the substrate while the at least one second microbe-promoting agent forms a gradient from high to low concentration from the distal end to the proximal end of the substrate.

In an aspect, different combinations and/or concentrations of microbe-promoting agents can be incorporated at different positions along the length of the substrate to allow for temporal and spatial interaction between the microbe-promoting agents and ingested products flowing through the device. In an aspect, different combinations and/or concentrations of microbe-promoting agents can be incorporated at different positions along the length of the substrate to allow for temporal and spatial interaction between microbe-promoting agents and components of the gastrointestinal wall.

Figure 31:
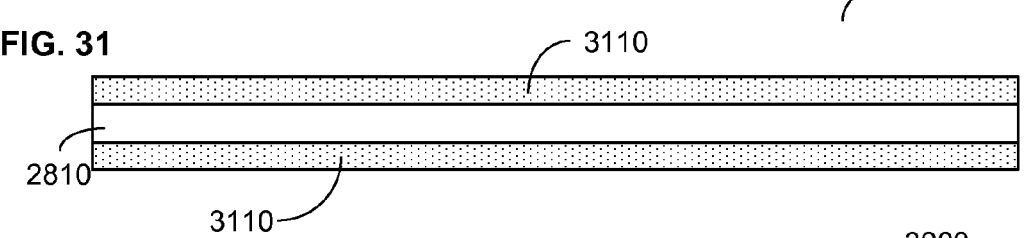
FIG. 31 is a schematic of a longitudinal cross-section through an embodiment of an adjunct for a gastrointestinal device including at least one microbe-promoting agent.
Figure 32:
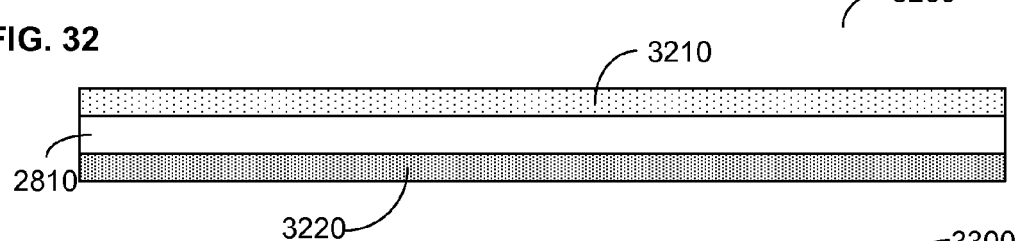
FIG. 32 is a schematic of a longitudinal cross-section through an embodiment of an adjunct for a gastrointestinal device including at least one microbe-promoting agent.
Figure 33:
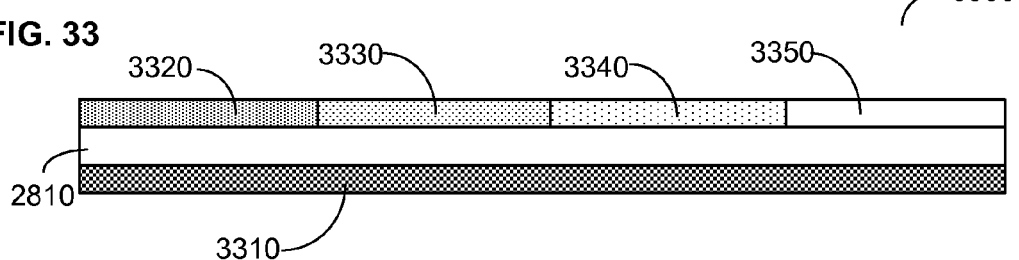
FIG. 33 is a schematic of a longitudinal cross-section through an embodiment of an adjunct for a gastrointestinal device including at least one microbe-promoting agent.

FIG. 31 shows a longitudinal cross-section through an embodiment of an adjunct for a gastrointestinal device. Adjunct 3100 includes substrate 2810 and at least one microbe-promoting agent 3110 (shown as a stippled pattern) on both the first and second surface of the substrate 2810. In an aspect, the at least one microbe-promoting agent 3110 is associated with at least a portion of a first surface and at least a portion of a second surface of substrate 2810. FIG. 32 shows a longitudinal cross-section through an embodiment of an adjunct for a gastrointestinal device. Adjunct 3200 includes substrate 2810 and at least one first microbe-promoting agent 3210 on a first surface of the substrate 2810 and at least one second microbe-promoting agent 3220 on a second surface of the substrate 2810. In an aspect, the at least one first microbe-promoting agent 3210 is associated with at least a portion of the first surface of substrate 2810 and the at least one second microbe-promoting agent 3220 is associated with at least a portion of the second surface of substrate 2810. FIG. 33 shows a longitudinal cross-section through an embodiment of an adjunct for a gastrointestinal device. Adjunct 3300 includes substrate 2810 and a gradient of at least one first microbe-promoting agent on a first surface of substrate 2810 and at least one second microbe-promoting agent 3210 on a second surface of substrate 2810. The gradient includes the at least one first microbe-promoting agent at a first concentration 3320, a second concentration 3330, a third concentration 3340, and a fourth concentration 3350.

In some embodiments, the substrate of the adjunct for a gastrointestinal device including at least one microbe-promoting agent includes a tubular structure. In an aspect, the tubular structure defines a lumen. In an aspect, the substrate of the adjunct for a gastrointestinal device forms a sleeve or liner. For example, the adjunct can include a tubular sleeve or liner including at least one microbe-promoting agent associated with the inner and/or the outer surface of the tubular sleeve or liner. For example, the substrate of the adjunct for a gastrointestinal device can form a sleeve or liner configured to fit over a commercially available gastrointestinal device, e.g., a commercially available sleeve, liner, or stent. For example, the substrate of the adjunct for a gastrointestinal device can form a sleeve or liner configured to fit inside a commercially available gastrointestinal device, e.g., a commercially available sleeve, liner, or stent. In an aspect, a lumen defined by a substrate that is a tubular structure may form a flow conduit through which ingested products are able to flow. In an aspect, the substrate of the adjunct for a gastrointestinal device is flexible. For example, the substrate is formed from a flexible material, e.g., a flexible polymer, the flexible material conforming to a shape defined by the gastrointestinal device. In an aspect, the substrate of the adjunct of the gastrointestinal device includes a flexible tubular structure.

Figure 34:
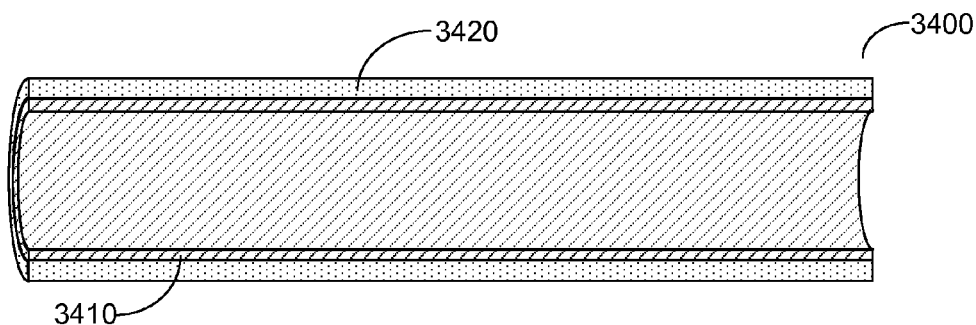
FIG. 34 is a schematic of a longitudinal cross-section through an embodiment of a tubular adjunct for a gastrointestinal device including at least one microbe-promoting agent.

FIGS. 34-38 illustrate aspects of a substrate of an adjunct for a gastrointestinal device that includes a tubular structure, the tubular structure including at least one microbe-promoting agent associated with at least one of a first surface and a second surface of the tubular structure. FIG. 34 shows a longitudinal cross-section through an embodiment of a tubular adjunct for a gastrointestinal device. Tubular adjunct 3400 includes tubular substrate 3410 (diagonal pattern) and at least one microbe-promoting agent 3420 (stippled pattern) associated with an outer surface of tubular substrate 3410. In an aspect, the tubular adjunct includes a single microbe-promoting agent. In an aspect, tubular adjunct includes a mixture of two or more microbe-promoting agents. In an aspect, the at least one microbe-promoting agent 3420 is associated with the entirety of the outer surface of tubular substrate 3410. In an aspect, the at least one microbe-promoting agent 3420 is associated with at least a portion of the outer surface of tubular substrate 3410.

Figure 35:
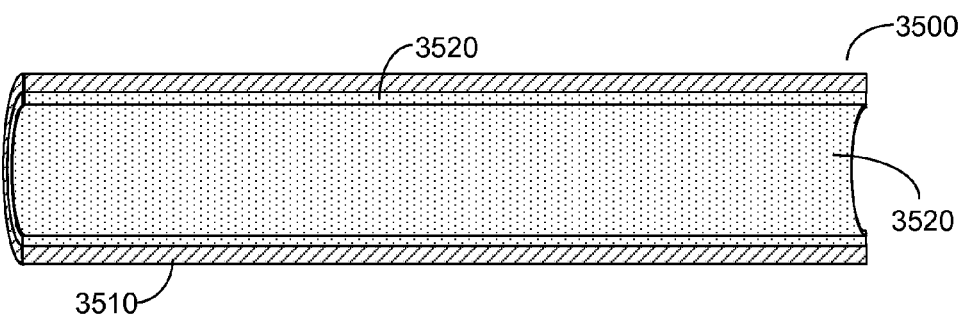
FIG. 35 is a schematic of a longitudinal cross-section through an embodiment of a tubular adjunct for a gastrointestinal device including at least one microbe-promoting agent.

FIG. 35 shows a longitudinal cross-section through an embodiment of a tubular adjunct for a gastrointestinal device. Tubular adjunct 3500 includes tubular substrate 3510 (diagonal pattern) and at least one microbe-promoting agent 3520 (stippled pattern) associated with an inner surface of tubular substrate 3510. In an aspect, the at least one microbe-promoting agent 3520 includes a microbe-promoting agent. In an aspect, the at least one microbe-promoting agent 3520 includes a mixture of two or more microbe-promoting agents. In an aspect, the at least one microbe-promoting agent 3520 is associated with the entirety of the inner surface of tubular substrate 3510. In an aspect, the at least one microbe-promoting agent 3520 is associated with at least a portion of the inner surface of tubular structure 3510.

Figure 36:
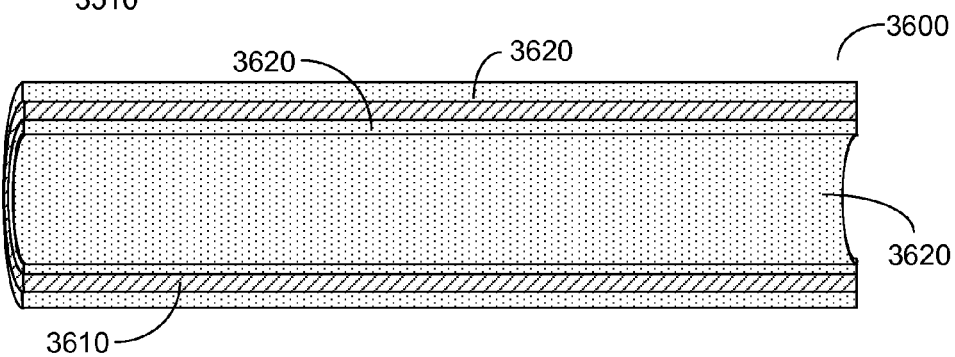
FIG. 36 is a schematic of a longitudinal cross-section through an embodiment of a tubular adjunct for a gastrointestinal device including at least one microbe-promoting agent.

FIG. 36 shows a longitudinal cross-section through an embodiment of a tubular adjunct for a gastrointestinal device. Tubular adjunct 3600 includes tubular substrate 3610 (diagonal pattern) and at least one microbe-promoting agent 3620 (stippled pattern) on the inner surface and the outer surface of tubular substrate 3610. In an aspect, the at least one microbe-promoting agent 3620 includes a microbe-promoting agent. In an aspect, the at least one microbe-promoting agent 3620 includes a mixture of two or more microbe-promoting agents. In an aspect, the at least one microbe-promoting agent 3620 is associated with the entirety the inner surface and/or the outer surface of tubular substrate 3610. In an aspect, the at least one microbe-promoting agent 3620 is associated with at least a portion of the inner surface and/or the outer surface of tubular structure 3610. In an aspect, tubular adjunct 3600 includes at least one first microbe-promoting agent on the inner surface of the tubular substrate 3610 and at least one second microbe-promoting agent on the outer surface of the tubular structure 3610.

Figure 37:
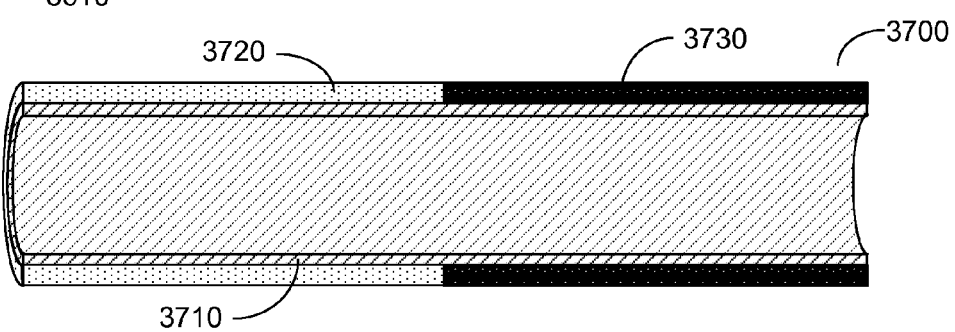
FIG. 37 is a schematic of a longitudinal cross-section through an embodiment of a tubular adjunct for a gastrointestinal device including at least one microbe-promoting agent.

FIG. 37 shows a longitudinal cross-section through an embodiment of a tubular adjunct for a gastrointestinal device. Tubular adjunct 3700 includes tubular substrate 3710 (diagonal pattern) and at least one first microbe-promoting agent 3720 (stippled pattern) on a first portion of the outer surface of tubular substrate 3710 and at least one second microbe-promoting agent 3730 (dark filled pattern) on a second portion of the outer surface of tubular structure 3710. In some embodiments, a tubular adjunct includes a tubular substrate and at least one first microbe-promoting agent on a first portion of the outer and/or inner surface of the tubular substrate and at least one second microbe-promoting agent on a second portion of the outer and/or inner surface of the tubular substrate.

Figure 38:
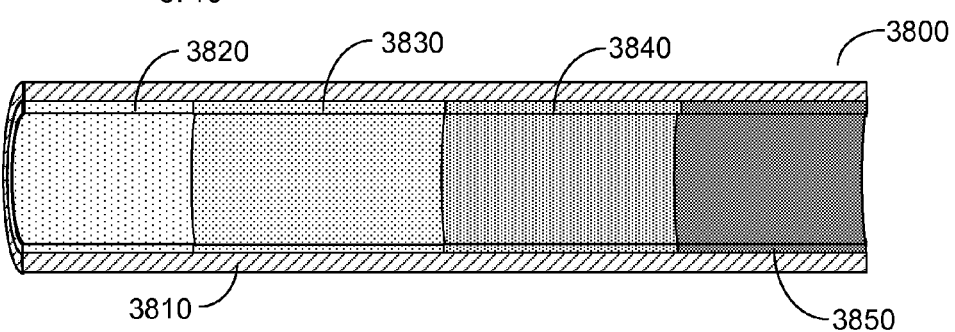
FIG. 38 is a schematic of a longitudinal cross-section through an embodiment of a tubular adjunct for a gastrointestinal device including at least one microbe-promoting agent.

FIG. 38 shows a longitudinal cross-section through an embodiment of a tubular adjunct for a gastrointestinal device. Tubular adjunct 3800 includes tubular substrate 3810 (diagonal pattern) and at least one microbe-promoting agent forming a gradient on the inner surface of the tubular substrate. In this example, tubular adjunct 3800 includes at least one microbe-promoting agent at a first concentration 3820 on a first portion of the inner surface of tubular substrate 3810, the at least one microbe-promoting agent at a second concentration 3830 on a second portion of the inner surface of tubular substrate 3810, the at least one microbe-promoting agent at a third concentration 3840 on a third portion of the inner surface of tubular substrate 3810, and the at least one microbe-promoting agent at a fourth concentration 3850 on a fourth portion of the inner surface of tubular substrate 3810. In some embodiments, the at least one microbe-promoting agent forms a gradient on the inner surface and/or the outer surface of a tubular substrate. In some embodiments, the tubular adjunct includes a gradient of at least one first microbe-promoting agent on the inner surface and/or the outer surface of a tubular substrate and a gradient of at least one second microbe-promoting agent on the inner surface and/or the outer surface of the tubular substrate.

The substrate of the adjunct for a gastrointestinal device including at least one microbe-promoting agent is configured to attach to a gastrointestinal device. In an aspect, the substrate includes an adhesive on at least one of the first surface and the second surface. In an aspect, the substrate includes an adhesive on at least one of the first surface and the second surface of the substrate conforming to a surface of the gastrointestinal device. For example, the substrate can include a pressure sensitive adhesive or an epoxy that adheres the adjunct for a gastrointestinal device to a surface of the gastrointestinal device. In an aspect, the adhesive forms a layer across the entirety of the at least one of the first surface and the second surface of the substrate. In an aspect, the adhesive forms a layer across at least a portion or portions of the at least one first surface and the second surface of the substrate. For example, the at least one microbe promoting agent can be associated with a central portion of the surface of a substrate, e.g., a patch, and an adhesive associated with the edges of the patch.

In an aspect, the substrate includes at least one anchor structure configured to attach the substrate to the gastrointestinal device. In an aspect, the at least one anchor is associated with at least one of a proximal end and a distal end of the substrate. For example, the at least one anchor structure can be associated with the proximal end of the substrate, e.g., the end of the adjunct that attaches to the proximal end of the gastrointestinal device. For example, the at least one anchor structure can be associated with the distal end of the substrate, e.g., the end of the adjunct that attaches to the distal end of the gastrointestinal device. In an aspect, the at least one anchor structure is incorporated into the substrate. In an aspect, the at least one anchor structure includes at least one hook, barb, snap, pin, clip, staple, or prong. In an aspect, the at least one anchor structure is inflatable. In an aspect, the at least one anchor structure is expandable. Non-limiting examples of anchor structures have been described above herein.

In some embodiments, an adjunct for a gastrointestinal device includes a flexible tubular substrate configured to attach to a gastrointestinal device, the flexible tubular substrate including an inner surface and an outer surface; and at least one microbe-promoting agent associated with at least one the inner surface and the outer surface of the flexible tubular substrate, the at least one microbe-promoting agent configured to promote at least one of attraction, colonization, and growth of at least one type of commensal microbe. For example, the flexible tubular substrate can include a sleeve, liner, or stent including at least one microbe-promoting agent on at least one surface and configured to attach to a gastrointestinal device. In an aspect, the flexible tubular substrate includes an adhesive on at least one of the inner surface and the outer surface. In an aspect, the flexible tubular substrate includes an adhesive on a surface conforming to a surface of the gastrointestinal device. In an aspect, the flexible tubular substrate includes at least one anchor structure configured to attach the flexible tubular substrate to the gastrointestinal device. For example, the flexible tubular substrate can include at least one hook, barb, snap, pin, clip, staple, or prong. For example, the flexible tubular substrate can include at least one inflatable or expandable anchor structure.

In an aspect, the substrate includes a layered wall, the substrate including the at least one microbe-promoting agent encased in the layered wall. In an aspect, the substrate includes a layered wall configured to allow an interaction between the at least one microbe-promoting agent and at least one ingested product and/or gastrointestinal component. For example, an adjunct for a gastrointestinal device can include a substrate configured to attach to a gastrointestinal device, the substrate including a layered wall, the substrate including at least one microbe-promoting agent encased in the layered wall, the layered wall configured to allow an interaction between the at least one microbe-promoting agent and at least one ingested product and/or gastrointestinal component. For example, the substrate can include a layered wall configured to allow components of ingest food or chyme to come in contact with the at least one microbe-promoting agent encased or entrapped in the layered wall. For example, the substrate can include a layered wall configured to allow components of the gastrointestinal tract to come in contact with the at least one microbe-promoting agent encased or entrapped in the layered wall.

In an aspect, the substrate includes a layered wall including a first layer, a second layer, and an internal space, wherein the internal space is disposed between the first layer and the second layer and includes the at least one microbe-promoting agent. For example, the substrate can include a patch including a first layer, a second layer, and an internal space, the internal space of the patch including at least one microbe-promoting agent disposed between the first layer and the second layer of the patch. In an aspect, the first layer and/or the second layer of the layered wall is formed from a semi-permeable material. For example, the substrate can include a sheet or a tubular structure, the sheet or the tubular structure including a layered wall, the layered wall including a first layer and/or a second layer formed from a semi-permeable material.

In an aspect, a substrate including a layered wall includes at least one first microbe-promoting agent in a first portion of the internal space and at least one second microbe-promoting agent in a second portion of the internal space. In an aspect, a substrate including a layered wall includes a gradient of at least one microbe-promoting agent in the internal space of the layered wall. In an aspect, the substrate includes at least one first microbe-promoting agent in the internal space and at least one second microbe-promoting agent on at least a portion the first surface and/or second surface of the substrate. In some embodiments, the at least one first and second microbe-promoting agent are the same microbe-promoting agent. In some embodiments, the at least one first and second microbe-promoting agent are different microbe-promoting agents.

In an aspect, the layered wall of the substrate includes an attachment mechanism for holding the first layer and the second layer together. In an aspect, the attachment mechanism includes a material, e.g., an adhesive, adherent, gel, or matrix, in the internal space that holds the first layer and the second layer together. For example, the internal space including the at least one microbe-promoting agent can include a material, e.g., an adhesive, adherent, gel, or matrix, to which the first layer and the second layer adhere. In an aspect, the attachment mechanism includes one or more staples, stitches, pins, or like mechanism for holding the first layer and the second layer together. For example, the layered wall can include staples to hold the inner layer and the outer layer together. For example, the inner layer and the outer layer can be stitched together with a form of biocompatible thread, e.g., suture thread. In an aspect, the inner layer and the outer layer are fused together at specific points along the length of the substrate in response to a stimulus, e.g., pressure, heat, or chemical stimulus. In an aspect, the attachment mechanism is degradable. For example, an adhesive may lose adhesive strength overtime. For example, the layered wall may include degradable staples or sutures.

In an aspect, the substrate including the at least one microbe-promoting agent in an internal space of a layered wall includes a permeable material in the internal space. In an aspect, the permeable material includes at least one of a mucus material, a gel material, a porous material, or a fibrous material. For example, the internal space of the layered wall of the substrate can include a material that allows for free flow of fluid and materials through the internal space within the confines of the first layer and second layer of the layered wall. In an aspect, at least one microbe-promoting agent is associated with at least one of a porous material, a fibrous material, a mucus material, or a gel material in the layered wall. In an aspect, the at least one microbe-promoting agent is immobilized in the layered wall. For example, at least one microbe-promoting agent can adhere to materials (e.g., fibers) or pores associated with an internal space of the layered wall. For example, the at least one microbe-promoting agent can line an exposed surface of a pore, allowing for interaction between the at least one microbe-promoting agent and an ingested product and/or gastrointestinal component. In an aspect, the at least one microbe-promoting agent is diffusible from the layered wall. For example, at least one of the first layer and/or the second layer can be formed from a material sufficiently porous enough to allow passage of the at least one microbe-promoting agent.

Figure 39A:
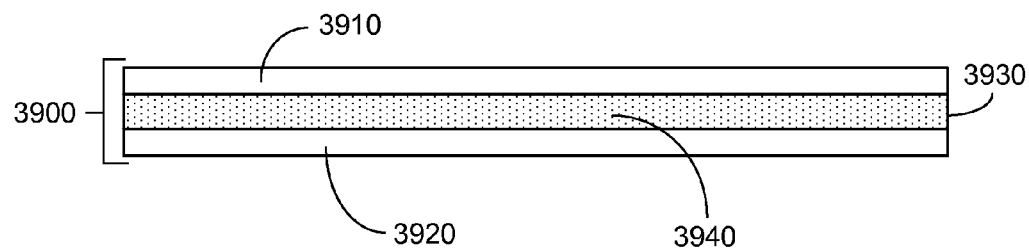
FIG. 39A is a schematic of a longitudinal cross-section through an adjunct for a gastrointestinal device including a substrate having a layered wall.
Figure 39B:
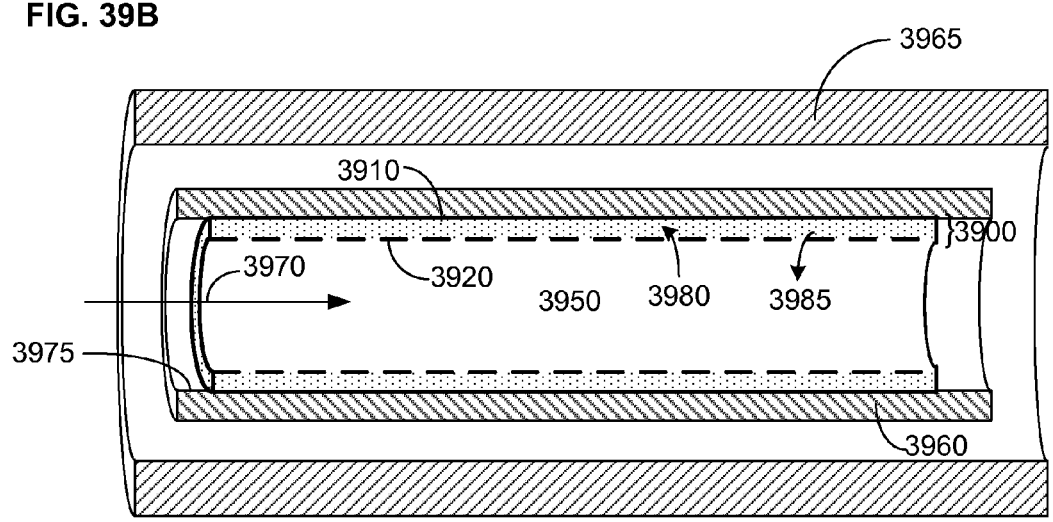
FIG. 39B is a schematic of a longitudinal cross-section through a tubular adjunct including a layered wall attached to a gastrointestinal device positioned in the gastrointestinal tract.
Figure 39C:
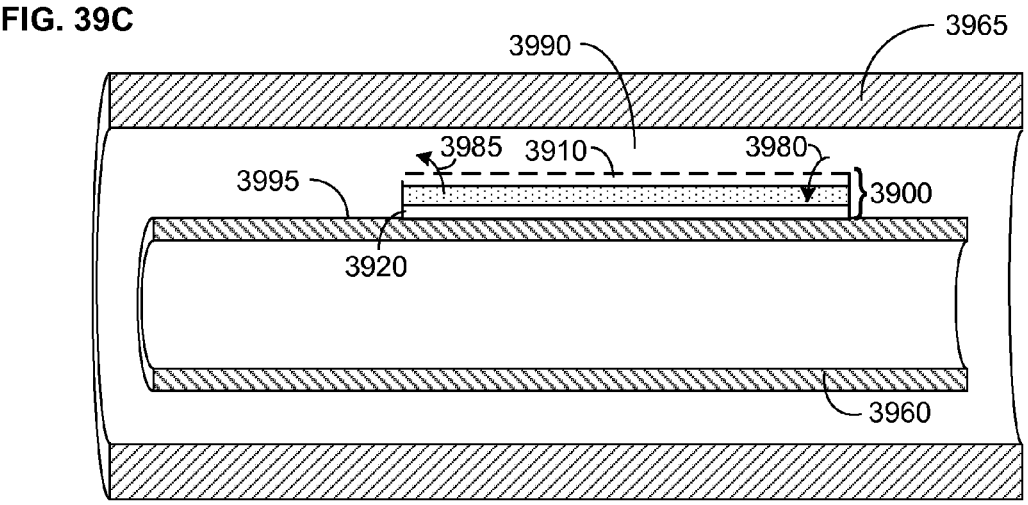
FIG. 39C is a schematic of a longitudinal cross-section through an adjunct including a layered wall attached to a gastrointestinal device positioned in the gastrointestinal tract.

FIGS. 39A-39C illustrate aspects of an embodiment of an adjunct for a gastrointestinal device including a substrate with a layered wall. FIG. 39A shows a longitudinal cross-section through a substrate of an adjunct for a gastrointestinal device. Substrate 3900 includes a layered wall including a first layer 3910, a second layer 3920, and an internal space 3930 disposed between first layer 3910 and second layer 3920. Internal space 3930 further includes at least one microbe-promoting agent 3940 (stippled pattern).

In an aspect, the adjunct for a gastrointestinal device including a substrate with a layered wall includes a tubular substrate with a layered wall. In an aspect, the tubular substrate including the layered wall is associated with at least a portion of an inner or outer surface of a gastrointestinal device, e.g., a gastrointestinal sleeve, liner, or stent. FIG. 39B illustrates aspects of an adjunct for a gastrointestinal device including a tubular substrate disposed in the gastrointestinal tract. FIG. 39B shows a longitudinal cross-section through a gastrointestinal device 3960 disposed in a gastrointestinal tract 3965. Arrow 3970 designates the flow of ingested components through gastrointestinal device 3960. Adjunct 3950 is shown attached to an inner surface 3975 of gastrointestinal device 3960. In an aspect, adjunct 3950 includes an adhesive on an outer surface of the first layer 3910 of the substrate 3900 conforming to a surface of gastrointestinal device 3960. In an aspect, adjunct 3950 includes at least one anchor structure configured to attach adjunct 3950 to gastrointestinal device 3960. Second layer 3920 of substrate 3900 includes a semi-permeable material allowing for interaction between the ingested components and the at least one microbe-promoting agent encased in the internal space of substrate 3900, as indicated by the in arrows 3975 and the out arrows 3980.

In an aspect, the adjunct for a gastrointestinal device including a substrate with a layered wall includes a substrate that is a patch or a sheet. In an aspect, the patch or sheet substrate including the layered wall is associated with at least a portion of an inner or outer surface of a gastrointestinal device. FIG. 39C illustrates aspects of an adjunct for a gastrointestinal device including a patch substrate disposed in the gastrointestinal tract. FIG. 39C shows a longitudinal cross-section through gastrointestinal device 3960 disposed in gastrointestinal tract 3965. Adjunct 3990 is shown attached to an outer surface 3995 of gastrointestinal device 3960. In an aspect, adjunct 3990 includes an adhesive on an outer surface of the second layer 3920 of the substrate 3900 conforming to a surface of gastrointestinal device 3960. In an aspect, adjunct 3990 includes at least one anchor structure configured to attach adjunct 3990 to gastrointestinal device 3960. First layer 3910 of substrate 3900 includes a semi-permeable material allowing for interaction between components of the gastrointestinal tract and the at least one microbe-promoting agent encased in the internal space of substrate 3900, as indicated by the in arrows 3980 and the out arrows 3985.

In an aspect, the adjunct for a gastrointestinal device includes a substrate configured to attach to a surface of the gastrointestinal device to form a layered section, the at least one microbe-promoting agent distributed in the layered section, the layered section configured to allow an interaction between the at least one microbe-promoting agent and the gastrointestinal tract of a subject. In an aspect, the layered section includes a first layer, a second layer, and an internal space, the first layer associated with the substrate of the adjunct, the second layer associated with the gastrointestinal device, and the internal space disposed between the first layer and the second layer and including the at least one microbe-promoting agent. In an aspect, an adjunct for a gastrointestinal device that includes a substrate configured to attach to a surface of the gastrointestinal device to form a layered section includes an adhesive and/or at least one anchor structure associated with the surface of the substrate including the at least one microbe-promoting agent. For example, a surface of the substrate of the adjunct can include an adhesive and at least one microbe-promoting agent, the surface configured to face and adhere to a surface of the gastrointestinal device.

In an aspect, at least a portion of the substrate is formed from a semi-permeable material. In an aspect, the at least a portion of the substrate includes a first layer and/or a second layer of a substrate including a layered wall. For example, the semi-permeable material may include pores sized to allow transit of ingested products and/or gastrointestinal components into the internal space of the layered wall. For example, the semi-permeable material may include pores sized to allow transit of the at least one microbe-promoting agent out of the internal space and into the gastrointestinal tract. In some embodiments, the semi-permeable material includes pores sized to allow transit of at least one type of commensal microbe into the internal space to interact with the at least one microbe-promoting agent. In an aspect, the semi-permeable material is selectively permeable. In an aspect, the semi-permeable material is selectively permeable based on size. In an aspect, the semi-permeable material is selectively permeable based on hydrophobicity. In an aspect, the semi-permeable material is selectively permeable based on charge. In an aspect, the semi-permeable material includes a plurality of pores. In an aspect, the semi-permeable material includes a fibrous material.

In an aspect, at least a portion of the substrate is formed from a substantially impermeable material. For example, the substrate can be formed from an impermeable material (e.g., an impermeable plastic) that prevents lateral transit of ingested products or components of the gastrointestinal tract through the substrate. In an aspect, a first layer of a substrate including a layered wall is formed from a substantially impermeable material and a second layer of the substrate including the layered wall is formed from a semi-permeable material.

In an aspect, at least a portion of the substrate includes a degradable material. For example, the substrate can be formed from a semi-permeable material or a substantially impermeable material that is degradable. In an aspect, at least a portion of the substrate includes a stimulus-responsive degradable material. For example, the stimulus-degradable material can include at least one of a time-responsive degradable material, a moisture-responsive degradable material, a temperature-responsive degradable material, a pH-responsive degradable material, or a chemical-responsive degradable material. In an aspect, the substrate is noncontiguous. For example, the substrate may be formed from a mesh-like material. For example, the substrate may resemble the lattice structure of a stent. For example, the substrate may be formed from two or more segments. For example, the substrate may be formed from two or more segment connected to one another through a degradable linkage. Non-limiting aspects of substrates of adjuncts for a gastrointestinal device have been described above herein.

An adjunct for a gastrointestinal device described herein includes at least one microbe-promoting agent configured to promote at least one of attraction, colonization, and growth of at least one type of commensal microbe. In an aspect, the at least one microbe-promoting agent includes properties, e.g., chemical or physical properties, that promote at least one of attraction, colonization, and growth of at least one type of commensal microbe. For example, the at least one microbe-promoting agent can include a chemoattractant for attracting at least one type of commensal microbe. For example, the at least one microbe-promoting agent can include a matrix, e.g., a mucus matrix, that provides a beneficial environment for colonization of at least one type of commensal microbe. For example, the at least one microbe-promoting agent can include a growth factor, e.g., a nutrient, that promotes the growth of at least one type of commensal microbe.

In an aspect, the at least one microbe-promoting agent is configured to promote at least one of attraction, colonization, and growth of at least one type of commensal gut microbe. In an aspect, the at least one microbe-promoting agent is configured to promote at least one of attraction, colonization, and growth of at least part of a gut microbiota. In an aspect, the at least one microbe-promoting agent is configured to promote at least one of attraction, colonization, and growth of at least one type of commensal microbe derived from a fecal sample. In an aspect, the at least one microbe-promoting agent is configured to promote at least one of attraction, colonization, and growth of at least one type of genetically engineered microbe. In an aspect, the at least one microbe-promoting agent is configured to promote at least one of attraction, colonization, and growth of at least one type of commensal microbe derived from in vitro culture. In an aspect, the at least one microbe-promoting agent is configured to promote at least one of attraction, colonization, and growth of at least one type of probiotic.

In an aspect, the at least one microbe-promoting agent is configured to promote at least one of attraction, colonization, and growth of at least one type of endogenous commensal microbe. For example, the at least one microbe-promoting agent can be configured to promote attraction, colonization, and/or growth of at least one type of commensal microbe resident in the gastrointestinal tract of the subject. In an aspect, the at least one microbe-promoting agent is configured to promote at least one of attraction, colonization, and growth of at least one type of administered commensal microbe. For example, the at least one microbe-promoting agent can be configured to promote attraction, colonization, and/or growth of an orally ingested commensal microbe, e.g., a commensal gut microbe, at least part of a gut microbiota, at least one type of commensal microbe from a fecal sample, a probiotic, a genetically engineered microbe, and/or a commensal microbe derived from in vitro culture. For example, the at least one microbe-promoting agent can be configured to promote attraction, colonization, and/or growth of an orally ingested commensal microbe administered in a dehydrated form (e.g., in powder, capsule, or pill form), liquid form, suspended form, or paste form.

In an aspect, the at least one microbe-promoting agent is configured to promote at least one of attraction, colonization, and growth of at least one type of commensal microbe beneficial to a subject. In an aspect, the at least one microbe-promoting agent is configured to promote at least one of attraction, colonization, and growth of at least one type of commensal microbe beneficial to a subject having a medical condition. In an aspect, the at least one microbe-promoting agent is configured to promote at least one of attraction, colonization, and growth of at least one type of commensal microbe beneficial to a subject having at least one of diabetes, obesity, metabolic syndrome, colitis, cancer, inflammatory bowel disease, irritable bowel syndrome, an autoimmune disorder, or a microbial infection. In an aspect, the at least one microbe-promoting agent is configured to promote at least one of attraction, colonization, and growth of at least one type of commensal microbe beneficial to the immune system of the subject. In an aspect, the at least one microbe-promoting agent is configured to promote at least one of attraction, colonization, and growth of at least one type of commensal microbe beneficial to a dietary condition of the subject. In an aspect, the dietary condition of the subject includes a dietary need of the subject (e.g., a nutritional need), weight control of the subject (e.g., obesity), or a food sensitivity of the subject (e.g., a gluten sensitivity or inability to digest lactose).

In an aspect, the at least one microbe-promoting agent is configured to promote formation of a microbiome. For example, the at least one microbe-promoting agent is configured to promote attraction, colonization, and growth of one or more types of microbes of the microbiome.

In an aspect, the at least one microbe-promoting agent includes at least one prebiotic agent. In an aspect, the at least one prebiotic agent includes at least one of a mucopolysaccharide, a chitin, a carrageenan, an arabinogalactin, a starch polysaccharide, an oligosaccharide, a fructo-oligosaccharide, or inulin. In an aspect, the at least one prebiotic agent includes at least one of a protein, a peptide, a lipid, a nutrient, a vitamin, a mineral, or a salt. Other non-limiting examples of prebiotic agents have been described above herein.

In an aspect, the at least one microbe-promoting agent includes at least one chemoattractant for attracting a microbe. In an aspect, the chemoattractant includes a ligand that interacts with microbial-chemoreceptors. For example, the chemoattractant can include sugars, e.g., D-maltose, D-ribose, or D-galactose. For example, the chemoattractant can include formyl peptides, e.g., di-, tri-, or tetrapeptides including a formyl group. See, e.g., Neumann et al (2010), *EMBO J.* 29:3484-3495, which is incorporated herein by reference. For example, the chemoattractant can include formyl peptides. For example, the chemoattractant can include chemokines. In an aspect, the at least one chemoattractant is in a coating. In an aspect, the at least one chemoattractant is in a degradable coating. For example, the at least one chemoattractant is slowly releasable from the degradable coating over time. For example at least two chemoattractants are releasable at different rates, e.g., chemoattractant that acts over longer distances is released first, and one that acts over shorter distances is subsequently released.

In an aspect, the at least one microbe-promoting agent includes a mucus. In an aspect, at least one of the first surface and the second surface of the substrate includes a mucus layer to promote attraction, colonization, and growth of at least one type of commensal microbe. In an aspect, the mucus includes natural mucus. For example, the microbe-promoting agent can include components of natural mucus isolated from a mammalian gastrointestinal tract. In an aspect, the mucus includes synthetic mucus. For example, the microbe-promoting agent can include components of synthetic mucus, e.g., mucin glycoproteins. Other non-limiting examples of mucus and mucus components have been described above herein.

In an aspect, the at least one microbe-promoting agent includes one or more mucins, heavily glycosylated proteins naturally produced by cells including those in epithelial tissues. In an aspect, the at least one microbe-promoting agent includes the gel-forming glycoprotein MUC2, the primary intestinal secreted mucin. In an aspect, the at least one microbe-promoting agent includes anti-bacterial proteins such as RegIIIγ, IgA, and IgM, constituents of mammalian mucus that inhibit pathogenic bacteria. In an aspect, the one or more mucins form an organized structure on at least one of the first surface and the second surface of the substrate, the organized structure of mucins containing both a dense area and a loose layer, the loose layer amenable to infiltration by commensal bacteria. For example, probiotic *Lactobacillus* species are known to have mucus-binding proteins that facilitate association of *Lactobacillus* species with intestinal mucus. See, e.g., Van Tassell & Miller (2011) *Nutrition* 3:613-636, which is incorporated herein by reference. In an aspect, a probiotic species is provided to promote the expression and synthesis of mucins as part of a mucus layer. For example, addition of probiotic *Lactobacillus casei* can be used to up-regulate the expression of MUC2 in cultured intestinal cells. See, e.g., Mattar et al. (2002) *Pediatr. Surg. Int.* 18:586-590, which is incorporated herein by reference.

In an aspect, the mucus is produced by a monolayer of cells grown on at least one of the first surface and the second surface of the substrate. In an aspect, at least one of the first surface and the second surface of the substrate includes a type of epithelial cell. For example, the epithelial cells can include intestinal epithelial cells. For example, the epithelial cells can include primary epithelial cells, e.g., isolated from the subject. For example the epithelial cells can include cultured cells. Non-limiting examples of cultured intestinal epithelial cells are available from ATCC (American Type Culture Collection) Manassas, Va. In an aspect, the epithelial cells are derived from stem cells. For example, the epithelial cells can include stem cells, e.g., embryonic or mesenchymal stem cells. For example, various lineages of intestinal epithelial cells can be derived from crypt base columnar cells isolated from the bottom of intestinal crypts. See, e.g., Fujii & Sato (2014) *Frontiers in Genetics,* 5:169, which is incorporated herein by reference. For example, at least one of the first surface and the second surface of the substrate can include a monolayer of intestinal submucosal cells. In some embodiments, the mucus is produced by a population of cells (e.g., intestinal epithelial cells, stem cells, submucosal cells) grown in an internal space of a substrate including a layered wall, and the mucus secreted from the internal space through a semi-permeable layer forming the layered wall of the substrate.

In an aspect, the mucus layer further includes antiseptic enzymes, e.g., lysozyme, immunoglobulins, inorganic salts, and proteins, e.g., lactoferrin. In an aspect, the mucus layer is formed on a surface of the substrate from a layer of mucus-producing cells cultured on or in the selectively permeable material of the substrate. In an aspect, the artificial mucus layer includes a buffer to buffer the low pH of the chyme entering the small intestine from the stomach.

In an aspect, the at least one microbe-promoting agent includes a binding agent. For example, at least one surface of the substrate of the adjunct for a gastrointestinal device can include a binding agent configured to bind at least one type of commensal microbe to promote attraction, colonization and/or growth of said at least one type of commensal microbe. For example, at least one surface of the substrate of the adjunct for a gastrointestinal device can include a binding agent configured to bind at least one first type of commensal microbe to promote attraction, colonization and/or growth of at least one second type of commensal microbe. In an aspect, the binding agent is configured to hold the at least one type of commensal microbe in a specific position on the substrate. In an aspect, the binding agent is configured to bind endogenous microbes. For example, the binding agent can be configured to bind endogenous commensal microbes. For example, the binding agent can be configured to bind pathogenic microbes, e.g., ingested pathogenic microbes. In an aspect, the binding agent is configured to bind administered microbes. For example, the binding agent can be configured to bind at least one type of orally administered commensal microbes, e.g., a commensal gut microbe, at least part of a gut microbiota, at least one type of commensal microbe from a fecal sample, a probiotic, a genetically engineered microbe, and/or a commensal microbe derived from in vitro culture. For example, orally administered microbes can include microbes administered in a liquid form or in a dehydrated form, capsule, or pill form. For example, orally administered microbes can include microbes administered via endoscope. For example, the binding agent can be configured to bind at least one type of rectally administered commensal microbes, e.g., a commensal gut microbe, at least part of a gut microbiota, at least one type of commensal microbe from a fecal sample, a probiotic, a genetically engineered microbe, and/or a commensal microbe derived from in vitro culture. For example, rectally administered microbes can include microbes administered via a colonoscope.

In an aspect, the binding agent includes a non-selective binding agent. For example, the at least one microbe-promoting agent can include at least one non-selective binding agent that non-selectively binds at least one type of commensal microbe. In an aspect, the non-selective binding agent includes an adhesive, an absorbent, an adsorbent, or a gel. In an aspect, the non-selective binding agent includes a biomolecule-binding polymer. For example, the non-selective binding agent can include a material, e.g., a gel, which non-selectively binds microbes to the substrate of the adjunct. In an aspect, the at least one binding agent interacts with biomolecules on the outer surface of microbes, e.g., proteins, polysaccharides, carbohydrates, phospholipids, proteoglycans, and the like, non-limiting examples of which include poly-ionic surfaces, e.g., poly-cationic surfaces such as polyamino acids (e.g., polylysine), fibronectin, nitrocellulose, cellulose nitrate, hydrophobic polymers, polyvinylidene fluoride coating, nylon coating, streptavidin or biotin, proteins, peptides, Concanavalin A, epoxy for binding proteins and peptides, aldehydes for immobilizing amino modified oligos and cDNAs, native proteins, tissues, and cells, and amines for immobilizing long oligos and cDNAs. Other non-limiting examples include adhesives, absorbents, adsorbents, gels (e.g., hydrogels, colloids, agar, or gelatin), biomolecule-binding polymers (e.g., nitrocellulose or poly-L-lysine), and extracellular matrix components (e.g., collagen, laminin, fibronectin, mucopolysaccharides, heparin sulfate, hyaluronidate, and chondroitin sulfate).

In an aspect, the binding agent includes a selective binding agent. For example, the at least one microbe-promoting agent can include at least one selective binding agent that selectively binds at least one type of commensal microbe. In an aspect, the selective binding agent is configured to selectively capture at least one type of commensal microbe. For example, the specific binding agent can be configured to recognize and bind a feature of a specific type of commensal microbe, e.g., a surface protein, lipopolysaccharide, carbohydrate, and the like. In an aspect, the selective binding agent includes an antibody, an aptamer, a DNA fragment, an RNA fragment, a protein, or a peptide. Other non-limiting examples of binding agents include antibody fragments, peptides, DNA, RNA, peptide nucleic acids, proteins, viruses, lipid, glycolipids, sphingolipids, phospholipids, carbohydrates, enzymes, receptors, lectins, peptide aptamers, bacteria, cells, cell fragments, inorganic molecules, organic molecules, artificial binding substrates (e.g., those formed by molecular imprinting), or combinations thereof.

In an aspect, the binding agent can include a ligand that specifically recognizes one or more microbes. For example, the binding agent can include CD14, which is a protein associated with monocyte/macrophages and known to bind lipopolysaccharide associated with Gram-negative bacteria as well as lipoteichoic acid associated with the Gram-positive bacteria *Bacillus subtilis* (see, e.g., Fan, et al. (1999) *Infect. Immun.* 67: 2964-2968, which is incorporated herein by reference). In an aspect, the binding agent can include all or part of a pattern recognition receptor that recognizes microbe-specific molecules (e.g., bacterial carbohydrates, bacterial or viral DNA or RNA, bacterial peptides, peptidoglycans, lipoteichoic acids, N-formylmethionine, lipoproteins, and fungal glucans). Non-limiting examples of pattern recognition receptors with microbe-binding properties include toll-like receptors, C-type lectin receptors, NOD-like receptors, RIG-I-like receptors, RNA helicases, complement receptors, collectins, ficolins, pentraxins, C-reactive proteins, lipid transferases, and the like. See, e.g., Modlin (2012) *J. Invest. Dermatol.* 132:882-886; Gauglitz et al. (2012) *Acta Derm. Venereol.* 92:291-298, which are incorporated herein by reference.

In an aspect, the at least one microbe-promoting agent includes at least one lectin. Lectins include carbohydrate-binding proteins that bind cell surface glycoproteins and/or glycolipids. Non-limiting examples of lectins include algal lectins, e.g., b-prism lectin; animal lectins, e.g., tachylectin-2, C-type lectins, C-type lectin-like proteins, calnexin-calreticulin, capsid protein, chitin-binding protein, ficolins, fucolectin, H-type lectins, I-type lectins, sialoadhesin, siglec-5, siglec-7, micronemal protein, P-type lectins, pentrxin, b-trefoil, galectins, congerins, selenocosmia huwena lectin-I, Hcgp-39, Ym1; bacterial lectins, e.g., *Pseudomonas* PA-IL, *Burkholderia* lectins, chromobacterium CV-IIL, *Pseudomonas* PA IIL, Ralsonia RS-ILL, ADP-ribosylating toxin, *Ralstonia* lectin, *Clostridium* hemagglutinin, botulinum toxin, tetanus toxin, cyanobacterial lectins, FimH, GafD, PapG, Staphylococcal enterotoxin B, toxin SSL11, toxin SSL5; fungal and yeast lectins, e.g., *Aleuria aurantia* lectin, integrin-like lectin, *Agaricus* lectin, *Sclerotium* lectin, *Xerocomus* lectin, *Laetiporus* lectin, *Marasmius oreades* agglutinin, agrocybe galectin, *coprinus* galectin-2, Ig-like lectins, L-type lectins; plant lectins, e.g., alpha-D-mannose-specific plant lectins, *amaranthus* antimicrobial peptide, hevein, pokeweed lectin, *Urtica dioica* UD, wheat germ WGA-1, WGA-2, WGA-3, artocarpin, *artocarpus* hirsute AHL, banana lectin, Calsepa, heltuba, jacalin, *Maclura pomifera* MPA, MornigaM, Parkia lectins, abrin-a, *abrus* agglutinin, amaranthin, castor bean ricin B, ebulin, mistletoe lectin, TKL-1, cyanovirin-N homolog, and various legume lectins; and viral lectins, e.g., capsid protein, coat protein, fiber knob, hemagglutinin, and tailspike protein. See, e.g., Kumar & Mittal (2011) *Bioinformation* 6:134-136, which is incorporated herein by reference.

In an aspect, the at least one microbe-promoting agent forms a coating on the at least one of the first surface and the second surface of the substrate. For example, the at least one microbe-promoting agent can include a coating of mucin-like proteins to form an artificial mucus layer on one or more surfaces of the substrate. In an aspect, the at least one microbe-promoting agent is embedded in the at least one of the first surface and the second surface of the substrate. For example, the at least one microbe-promoting agent can be embedded into a degradable material forming the substrate, e.g., a degradable polymer material.

In an aspect, the at least one microbe-promoting agent is covalently attached to the at least one of the first surface and the second surface of the substrate. For example, the at least one microbe-promoting agent can be covalently attached to the substrate through a crosslinking reagent, e.g., a homobifunctional, heterobifunctional, and/or photoreactive cross-linking reagent. For example, the at least one microbe-promoting agent can be cross-linked to at least a portion of the first surface and/or the second surface of the substrate through amine groups, carbohydrate groups, sulfhydryl groups, or combinations thereof associated with a surface component, e.g., a protein or carbohydrate, of the at least one type of commensal microbe. A variety of crosslinking reagents are known and available from commercial sources (from, e.g., Pierce-Thermo Fisher Scientific, Inc., Rockford, Ill.). In an aspect, the at least one microbe-promoting agent is non-covalently attached to the at least one of the first surface and the second surface of the substrate.

In an aspect, the at least one microbe-promoting agent is incorporated into a coating on the at least one of the first surface and the second surface of the substrate. In an aspect, the at least one microbe-promoting agent is incorporated into a degradable coating on the at least one of the first surface and the second surface of the substrate. For example, the at least one microbe-promoting agent can be incorporated into a coating material that degrades over time to release the at least one microbe-promoting agent. In an aspect, the at least one microbe-promoting agent is incorporated into a stimulus-responsive degradable coating on the at least one of the first surface and the second surface of the substrate. For example, the at least one microbe-promoting agent can be incorporated into a coating material that degrades in response to a stimulus, e.g., time, moisture, temperature, pH, or chemicals.

In an aspect, the stimulus-responsive degradable coating includes at least one of a time-responsive degradable coating, a moisture-responsive degradable coating, a temperature-responsive degradable coating, a pH-responsive degradable coating, or a chemical-responsive degradable coating. For example, the at least one microbe-promoting agent can be incorporated into a time-responsive degradable coating that degrades over time to release the at least one microbe-promoting agent. For example, the at least one microbe-promoting agent can be incorporated into a moisture-responsive degradable coating that degrades over time in responsive to moisture associated with the gastrointestinal tract to release the at least one microbe-promoting agent. For example, the at least one microbe-promoting agent can be incorporated into a temperature-responsive degradable coating that degrades over time in response to body heat, e.g., 37 degrees centigrade, associated with the gastrointestinal tract to release the at least one microbe-promoting agent. For example, the at least one microbe-promoting agent can be incorporated into a pH-responsive degradable coating that degrades over time in response to pH changes in the gastrointestinal tract as ingested material moves from the stomach (pH 1.0-3.0) into the upper (pH 4.8-8.2) and the lower (pH 7.0-7.5) intestinal tract to release the at least one microbe-promoting agent. Non-limiting examples of temperature-responsive and pH-responsive polymers are described in Schmaljohann (2006) *Adv. Drug Deliv. Rev.* 58:1655-1670, which is incorporated herein by reference. For example, the at least one microbe-promoting agent can be incorporated into a chemical-responsive degradable coating that degrades in response to either an endogenous chemical or an administered/ingested chemical to release the at least one microbe-promoting agent. For example, the chemical-responsive degradable coating can include a hydrogel that is responsive to a chemical, e.g., glucose, a protein, an antibody, or an aptamer. See, e.g., Yang et al. (2008) *J. Am. Chem. Soc.* 130:6320-6321; Miyata et al. (2006) *Proc. Natl. Acad. Sci.* 103:1190-1193, which are incorporated herein by reference.

In an aspect, the adjunct for a gastrointestinal device includes at least one first microbe-promoting agent in a first degradable coating and at least one second microbe-promoting agent in a second degradable coating. In an aspect, the first degradable coating and the second degradable coating degrade at different rates. For example, the at least one first microbe-promoting agent can be in a first time-responsive degradable coating configured to degrade at a first rate and the at least one second microbe-promoting agent can be in a second time-responsive degradable coating configured to degrade at a second rate. For example, the at least one first microbe-promoting agent can be in a first stimulus-responsive degradable coating and the at least one second microbe-promoting agent in a second stimulus-responsive degradable coating, the first stimulus-responsive degradable coating degrading at a different pH or temperature than the second stimulus-responsive degradable coating. For example, the at least one first microbe-promoting agent can be in a first chemical-responsive degradable coating and the at least one second microbe-promoting agent in a second chemical-responsive degradable coating, the first chemical-responsive degradable coating degrading in response to a first chemical and the second chemical-responsive degradable coating degrading in response to a second chemical.

In an aspect, an adjunct for a gastrointestinal device including at least one microbe-promoting agent further includes at least one therapeutic agent. For example, the adjunct for a gastrointestinal device including the at least one microbe-promoting agent can include at least one anti-inflammatory agent, chemotherapeutic agent, or antimicrobial agent. In an aspect, the at least one therapeutic agent is associated with at least a portion of the first surface and/or the second surface of the substrate of the adjunct. In an aspect, the at least one therapeutic agent is included in a degradable coating or matrix associated with at least a portion of the first surface and/or the second surface of the substrate of the adjunct. In an aspect, the at least one therapeutic agent is associated with the internal space of a substrate including a layered wall. Non-limiting examples of therapeutic agents have been described above herein.

In an aspect, an adjunct for a gastrointestinal device including at least one microbe-promoting agent further includes at least one bioactive agent. For example, the adjunct for a gastrointestinal device including the at least one microbe-promoting agent can include at least one digestive enzyme. For example, the at least one bioactive agent can further include antiseptic enzymes (e.g., lysozyme) immunoglobulins, inorganic salts, and proteins (e.g., lactoferrin). In an aspect, the at least one bioactive agent is associated with at least a portion of the first surface and/or the second surface of the substrate of the adjunct. In an aspect, the at least one bioactive agent is included in a degradable coating or matrix associated with at least a portion of the first surface and/or the second surface of the substrate of the adjunct. In an aspect, the at least one bioactive agent is associated with the internal space of a substrate including a layered wall. Non-limiting examples of bioactive agents and bioactive agents have been described above herein.

Gastrointestinal System Including at Least One Microbe-Promoting Agent

A gastrointestinal system including at least one microbe-promoting agent is described herein. In an aspect, a gastrointestinal system includes a gastrointestinal device; and an adjunct configured to attach to the gastrointestinal device, the adjunct including a substrate, the substrate including a first surface and a second surface, and at least one microbe-promoting agent associated with at least one of the first surface and the second surface of the substrate, the at least one microbe-promoting agent configured to promote at least one of attraction, colonization, and growth of at least one type of commensal microbe.

FIGS. 40A and 40B illustrate aspects of a gastrointestinal system. FIG. 40A shows gastrointestinal system 4000 includes gastrointestinal device 4010 and adjunct 4020 configured to attach to gastrointestinal device 4010. Adjunct 4020 includes a tubular substrate 4030. Tubular substrate includes an inner and an outer surface, the inner surface including at least one microbe-promoting agent. In some embodiments, the system can include an adjunct including a tubular substrate with at least one microbe-promoting agent on an outer surface of the tubular substrate. In an aspect, adjunct 4020 is configured to insert into gastrointestinal device 4010. Adjunct 4020 further includes an anchor structure 4040 configured to attach adjunct 4020 to gastrointestinal device 4010. In some embodiments, the adjunct is configured to attach to gastrointestinal device through an adhesive associated with at least one surface of the substrate. In some embodiments, the adjunct is configured to attach to gastrointestinal device through at least one anchor structure, e.g., at least one hook, barb, prong, or other anchoring structure. Gastrointestinal device 4010 can include a gastrointestinal sleeve, liner, or stent. In the non-limiting example shown in FIG. 40A, gastrointestinal device 4010 includes a sleeve 4050 and an anchoring mechanism 4060.

FIG. 40B illustrates placement of gastrointestinal system 4000 in a gastrointestinal tract 4060. In this non-limiting example, gastrointestinal system 4000 including gastrointestinal device 4010 and adjunct 4020 is positioned in the upper portion of the small intestine. Adjunct 4020 is disposed in and extends along at least a portion of the inner lumen of gastrointestinal device 4010. In some embodiments, adjunct 4020 is attached to the inner surface of gastrointestinal device 4010 such that the at least one microbe-promoting agent can interact with the contents of ingested food or chyme passing through the gastrointestinal device. In some embodiments, the adjunct is attached to the outer surface of gastrointestinal device such that the at least one microbe-promoting agent can interact with components of the gastrointestinal tract.

Figure 41A:
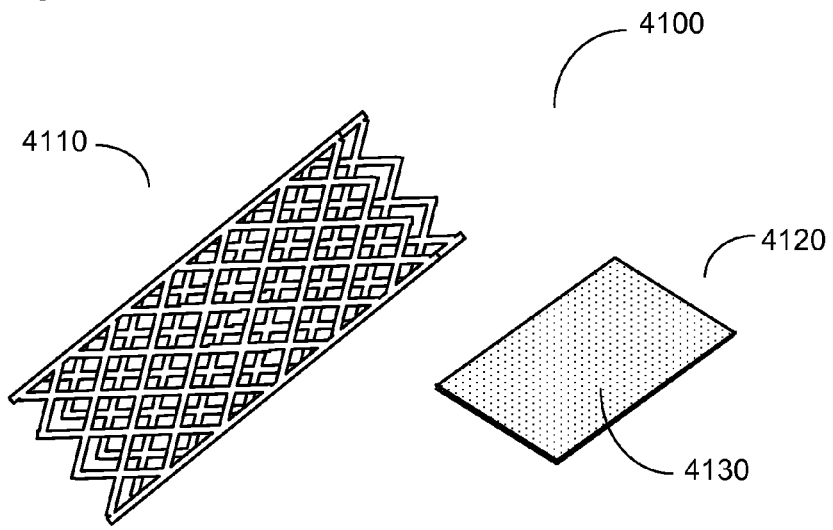
FIG. 41A is a schematic of an embodiment of a gastrointestinal system including a gastrointestinal device and an adjunct for a gastrointestinal device including at least one microbe-promoting agent.
Figure 41B:
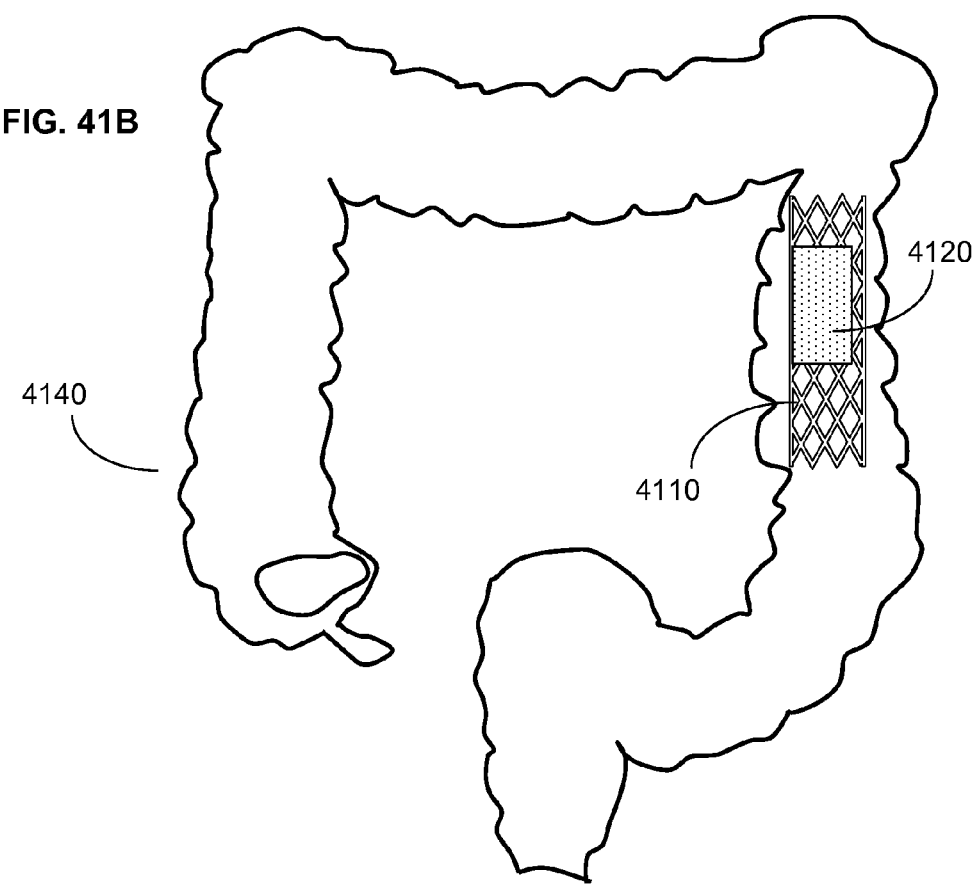
FIG. 41B is a schematic of an embodiment of a gastrointestinal system positioned in a gastrointestinal tract.

FIGS. 41A and 41B illustrate aspects of a gastrointestinal system including at least one microbe-promoting agent. FIG. 41 shows gastrointestinal system 4100 including gastrointestinal device 4110 and adjunct 4120 configured to attach to gastrointestinal device 4110. Adjunct 4120 includes a substrate and at least microbe-promoting agent 4130 (stippled pattern) on at least one surface of the substrate. In some embodiments, adjunct 4120 is configured to attach to gastrointestinal device 4110 through an adhesive associated with at least one surface of the substrate. In some embodiments, adjunct 4120 is configured to attach to gastrointestinal device 4110 through at least one anchor structure, e.g., at least one hook, barb, prong, or other anchoring structure. Gastrointestinal device 4110 can include a gastrointestinal stent.

FIG. 41B illustrates placement of gastrointestinal system 4100 in a lower gastrointestinal tract 4140 of a subject. In this non-limiting example, gastrointestinal system 4100 including gastrointestinal device 4110 and adjunct 4120 is positioned in the lower portion of the large intestine. In some embodiments, adjunct 4120 is attached to the inner surface of gastrointestinal device 4110 such that the at least one microbe-promoting agent can interact with the contents of ingested food or chyme passing through gastrointestinal device 4110. In some embodiments, adjunct 4120 is attached to the outer surface of gastrointestinal device 4110 such that the at least one microbe-promoting agent can interact with components of the gastrointestinal tract. In some embodiments, gastrointestinal device 4110 is non-contiguous, e.g., has a mesh-like framework common in stents, such that a surface of the substrate including the at least one microbe-promoting agent can face a surface of the gastrointestinal device and still allow interaction of the at least one microbe-promoting agent to interact with either the contents of ingested food or chyme, or components of the gastrointestinal tract.

A gastrointestinal system including at least one microbe-promoting agent such as described herein includes a gastrointestinal device. The gastrointestinal device is sized for placement in a portion of the gastrointestinal tract of a subject. It is anticipated that the entirety of the gastrointestinal device will reside within the gastrointestinal tract. In an aspect, the gastrointestinal device is sized for placement in a mouth, in a mouth, an esophagus, a stomach, a pylorus, a duodenum, a jejunum, an ileum, a caecum, an ascending colon, a transverse colon, a descending colon, a sigmoid colon, a rectum, an anus, a gland, a duct, a sphincter, or a combination thereof of the subject. In an aspect, the gastrointestinal system including the gastrointestinal device and the adjunct with the at least one microbe-promoting agent replaces or supports a defective or at risk portion of the gastrointestinal tract. In an aspect, the gastrointestinal system including the gastrointestinal device and the adjunct with the at least one microbe-promoting agent acts as an artificial gut. For example, the adjunct can provide at least one microbe-promoting agent to promote at least one of attraction, colonization, and growth of at least one type of commensal microbe, either ingested or associated with the gastrointestinal wall. In an aspect, the adjunct of the gastrointestinal system includes at least one microbe-promoting agent that promotes at least one of attraction, colonization, and growth of at least one type of commensal microbe that replaces the digestive and/or nutritional functions of endogenous microbes that are otherwise covered by a portion of the gastrointestinal device. In an aspect, the at least one microbe-promoting agent promotes at least one of attraction, colonization, and growth of at least one type of commensal microbe that forms a microbiome.

In an aspect, the gastrointestinal device includes a sleeve, a liner, or a stent. For example, the gastrointestinal device can include a sleeve with an anchoring mechanism, the sleeve configured to extend into the gastrointestinal tract. Non-limiting examples of gastrointestinal devices including a sleeve are described in U.S. Pat. No. 7,037,344 to Kagan et al. titled "Apparatus and Methods for Treatment of Morbid Obesity;" U.S. Patent Application No. 2013/0331759 from Neisz et al. titled "Device and Methods for Gastrointestinal Bypass;" and U.S. Patent Application No. 2014/0012178 from Chin titled "System and Methods for Bariatric Therapy," which are incorporated herein by reference. In an aspect, the gastrointestinal device includes a gastrointestinal liner. For example, the gastrointestinal device can include an implantable gastrointestinal liner, for example, a duodenal-jejunal bypass liner. A non-limiting example of a duodenal-jejunal bypass liner is described in Escalona et al. (2012) "Weight Loss and Metabolic Improvement in Morbidly Obese Subjects Implanted for 1 Year with an Endoscopic Duodenal-Jejunal Bypass Liner," *Ann. Surg.* 255:1080-1085, which is incorporated herein by reference. For example, the method can include using a commercially available intestinal sleeve, e.g., the EndoBarrier® gastrointestinal liner from GI Dynamics, Inc., Lexington, Mass. See, e.g., Rohde et al. (2013) *BMJ Open* 3:e003417, which is incorporated herein by reference. In an aspect, the gastrointestinal device includes a gastrointestinal stent. For example, the gastrointestinal device can include an esophageal stent, a biliary stent, a gastric stent, a enteral stent, and/or a colorectal stent. Non-limiting examples of gastrointestinal stents are described in Loch & Kahaleh (2007) "Stents for Gastrointestinal Tract and Nutritional Implications," *Practical Gastroenterology* January 2007: 48-57; and Lam-Tsai et al. (2011) "A Review of Gastrointestinal Stenting," *Gastroenterology & Endoscopy News*, June 2011: 1-8, which are incorporated herein by reference. Also see, e.g., U.S. Pat. No. 7,025,791 to Levine et al. titled "Bariatric Sleeve;" U.S. Pat. No. 7,976,488 to Levine & Melanson titled "Gastrointestinal Anchor Compliance;" U.S. Patent Application No. 2012/0158026 to Behan titled "Gastrointestinal Implant Device;" U.S. Patent Application No. 2021/0184893 to Thompson et al. titled "Anchors and Methods for Intestinal Bypass Sleeves;" U.S. Patent Application No. 2013/0281911 to Babkes et al. titled "Anchored Non-Piercing Duodenal Sleeve and Delivery Systems;" which are incorporated herein by reference.

In an aspect, the gastrointestinal device is of a type configured for treating a medical condition of a subject. For example, the gastrointestinal device can be of a type configured for treating diabetes, obesity, metabolic syndrome, colitis, cancer, inflammatory bowel disease, irritable bowel syndrome, an autoimmune disorder, trauma, stricture, or a microbial infection.

A gastrointestinal system such as described herein includes an adjunct. In an aspect, the adjunct includes a patch. In an aspect, the adjunct includes a sheet. In an aspect, the adjunct includes a tubular structure. In an aspect, the adjunct is flexible. In an aspect, the adjunct includes a flexible tubular structure. In an aspect, the adjunct includes a substrate that includes a patch, sheet, or tubular structure. In an aspect, the adjunct includes a substrate that includes a flexible patch, sheet, or tubular structure.

The adjunct of the gastrointestinal system is configured to attach to the gastrointestinal device. In an aspect, the adjunct includes an adhesive on a surface of the substrate. In an aspect, the adhesive is on a surface of the substrate conforming to a surface of the gastrointestinal device. For example, the substrate of the adjunct can include glue, epoxy, sealant, mucilage, paste, or other adhesive or binder material. For example, the substrate of the adjunct can include a pressure sensitive adhesive, e.g., a styrene copolymer pressure-sensitive adhesive. Non-limiting examples adhesives have been described above herein.

In an aspect, the adjunct includes at least one anchor structure configured to attach the adjunct to the gastrointestinal device. In an aspect, the at least one anchor structure is associated with at least one of a proximal and a distal end of the adjunct. In an aspect, the at least one anchor structure is incorporated into the adjunct. In an aspect, the at least one anchor structure includes at least one hook, barb, snap, pin, clip, staple, or prong. In an aspect, the at least one anchor structure is inflatable. In an aspect, the at least one anchor structure is expandable. Non-limiting examples of anchor structures associated with adjunct for a gastrointestinal device have been described above herein.

In an aspect, the adjunct is configured to attach to an inner surface of the gastrointestinal device. For example, the adjunct can be configured to attach to an inner surface of a gastrointestinal sleeve, liner, or stent, allowing the at least one microbe-promoting agent associated with the adjunct to come in contact with the contents of ingested food or chyme transiting through the gastrointestinal sleeve, liner, or stent. In an aspect, the adjunct is configured to attach to an outer surface of the gastrointestinal device. For example, the adjunct can be configured to attach to an outer surface of a gastrointestinal sleeve, liner, or stent, allowing the at least one microbe-promoting agent associated with the adjunct to come in contact with components of the gastrointestinal tract.

In an embodiment, a gastrointestinal system includes a gastrointestinal device and an adjunct for the gastrointestinal device including a layered wall, the at least one microbe-promoting agent encased in the layered wall. For example, the gastrointestinal system can include a gastrointestinal device (e.g., a sleeve, liner, or stent) and an adjunct for the gastrointestinal device including a substrate (e.g., a patch, sheet, or tubular structure) having a layered wall encasing at least one microbe-promoting agent. In an aspect, the substrate of the adjunct includes a layered wall, the substrate including the at least one microbe-promoting agent encased in the layered wall. In an aspect, the layered wall includes a first layer, a second layer, and an internal space, the internal space disposed between the first layer and the second layer and including the at least one microbe-promoting agent.

Figure 42A:
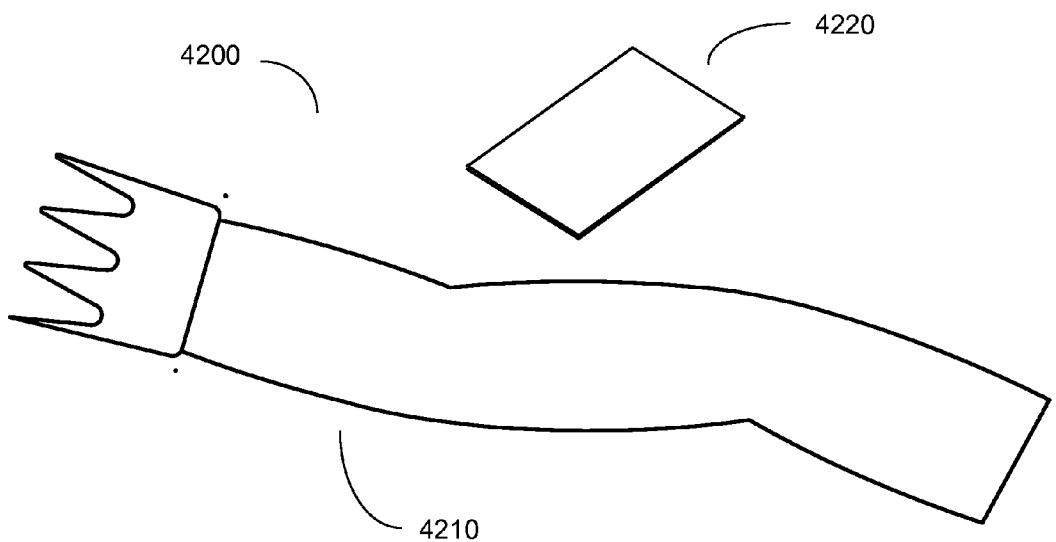
FIG. 42A is a schematic of an embodiment of a gastrointestinal system including a gastrointestinal device and an adjunct for a gastrointestinal device including at least one microbe-promoting agent in a layered wall.
Figure 42B:
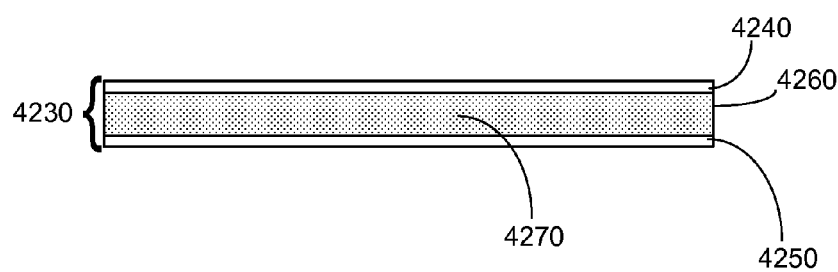
FIG. 42B is a longitudinal cross-section through an embodiment of an adjunct for a gastrointestinal device including at least one microbe-promoting agent associated with a layered wall.
Figure 42C:
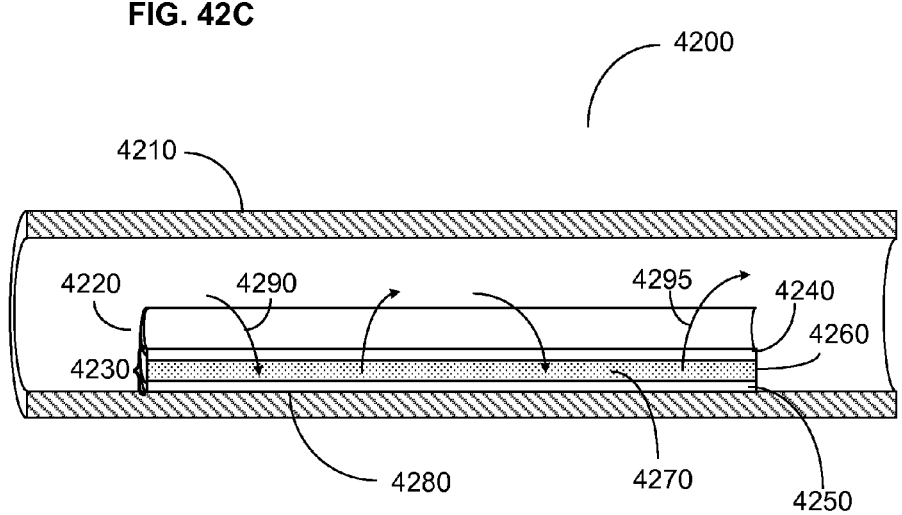
FIG. 42C is longitudinal cross-section through an embodiment of a system including a gastrointestinal device and an adjunct for a gastrointestinal device including at least one microbe-promoting agent associated a with layered wall.

FIGS. 42A-42C illustrate aspects of an embodiment of a gastrointestinal system including a gastrointestinal device and an adjunct for the gastrointestinal device including a layered wall. FIG. 42A shows gastrointestinal system 4200 including gastrointestinal device 4210 (e.g., a gastrointestinal sleeve or liner) and adjunct 4220. In this non-limiting example, adjunct 4220 includes a substrate (e.g., a patch or sheet), the substrate including a layered wall, the plurality of the at least one type of commensal microbe encased in the layered wall. At least one surface of adjunct 4220 includes an adhesive and/or at least one anchor structure configured to attach the adjunct 4220 to a surface of gastrointestinal device 4210. In some embodiments, the gastrointestinal system includes an adjunct having a tubular substrate including a layered wall that attaches to and at least partially covers an inner or an outer surface of the gastrointestinal device. A non-limiting example is shown in FIG. 39B. FIG. 42B shows a longitudinal cross-section through substrate 4230 of adjunct 4220. Substrate 4230 can include a patch, a sheet, or a tubular substrate. Substrate 4230 includes a first layer 4240, a second layer 4250, and internal space 4260. Internal space 4260 is disposed between first layer 4240 and second layer 4250 and includes at least one microbe-promoting agent 4270 (stippled pattern). In an aspect, at least one of the first layer and the second layer of the layered wall is formed from a semi-permeable material. FIG. 42C shows a longitudinal cross-section through a portion of gastrointestinal system 4200 including adjunct 4220 attached to an inner surface 4280 of gastrointestinal device 4210. In some embodiments, adjunct 4220 includes an adhesive for attaching to gastrointestinal device 4210. In some embodiments, adjunct 4220 includes at least one anchoring structure for attaching to gastrointestinal device 4210. Adjunct 4220 includes substrate 4230 including a layered wall with a first layer 4240, a second layer 4250, internal space 4260, and at least one microbe-promoting agent 4270. First layer 4240 of adjunct 4220 is further formed from a semi-permeable material, allowing for material to transit in (arrow 4290) and transit out (arrow 4295) the portion of the layered section including the at least one microbe-promoting agent 4270. For example, ingested components can transit into the layered wall to interact with the at least one microbe-promoting agent and/or the at least one microbe-promoting agent can transit out of the layered wall to interact with the ingested components. For example, an ingested at least one type of commensal microbe can transit into the layered wall to interact with the at least one microbe-promoting agent and/or the at least one microbe-promoting agent can transit out of the layered wall to interact with an ingested at least one type of commensal microbe. In some embodiments, the adjunct including the layered wall is attached to an outer surface of the gastrointestinal device, allowing gastrointestinal components associated with the gastrointestinal wall to interact with the at least one microbe-promoting agent encased in the layered wall. For example, at least one type of commensal microbe resident in the gastrointestinal tract can transit into the layered wall to interact with the at least one microbe-promoting agent and/or the at least one microbe-promoting agent can transit out of the layered wall to interact with at least one type of commensal microbe resident in the gastrointestinal tract. Other non-limiting aspects of an adjunct for a gastrointestinal device including a layered wall have been described above herein.

In an embodiment, a gastrointestinal system includes a gastrointestinal device and an adjunct for a gastrointestinal device configured to attach to at least a portion of the gastrointestinal device to form a layered section. In an aspect, the adjunct includes a substrate, the substrate including at least one microbe-promoting agent associated with a surface of the substrate, the at least one microbe-promoting agent configured to promote at least one of attraction, colonization, and growth of at least one type of commensal microbe, the surface of the substrate including the at least one microbe-promoting agent configured to face a surface of the gastrointestinal device to form the layered section. In an aspect, the first surface or the second surface of the substrate including the at least one microbe-promoting agent is configured to face a surface of the gastrointestinal device to form the layered section, wherein the layered section is configured to allow an interaction between the at least one microbe-promoting agent and the gastrointestinal tract of a subject. For example, the adjunct can include a substrate formed from a semi-permeable material, the at least one microbe-promoting agent coating a first surface of the substrate, the first surface affixed to a surface of the gastrointestinal device to form a layered section.

Figure 43A:
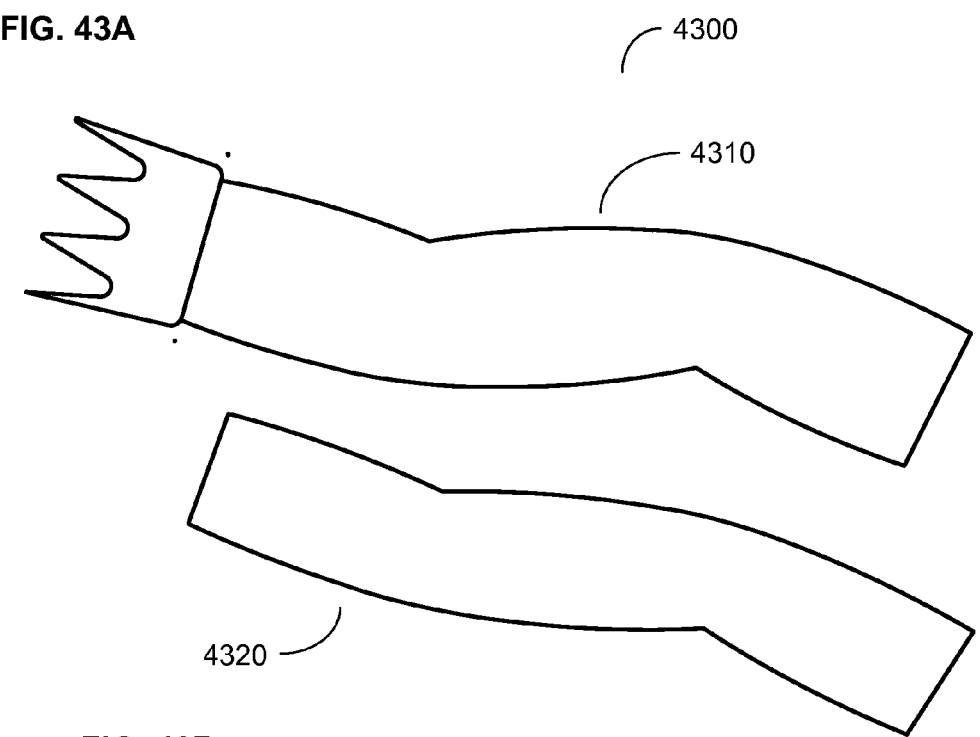
FIG. 43A is a schematic of an embodiment of a gastrointestinal system including a gastrointestinal device and a tubular adjunct for a gastrointestinal device including at least one microbe-promoting agent.
Figure 43B:
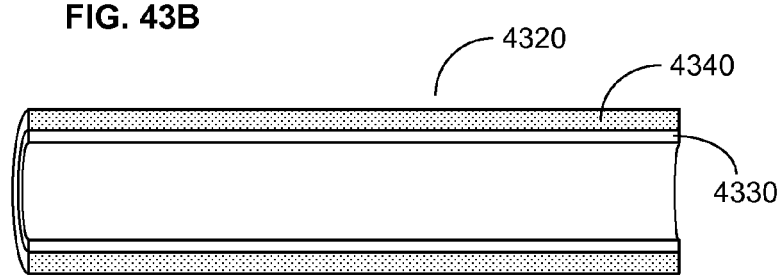
FIG. 43B is a longitudinal cross-section through of an embodiment a tubular adjunct for a gastrointestinal device including at least one microbe-promoting agent.
Figure 43C:
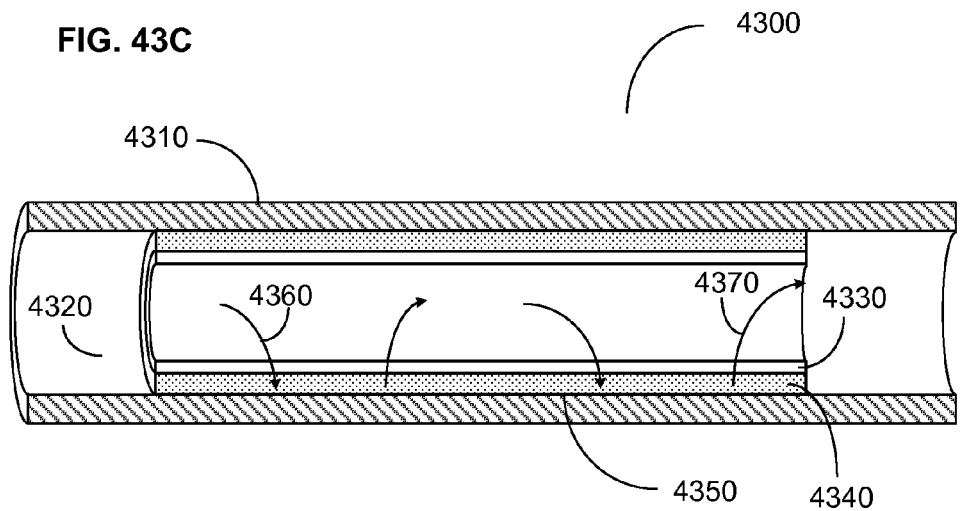
FIG. 43C is a longitudinal cross-section through an embodiment of a gastrointestinal system including a gastrointestinal device and a tubular adjunct for a gastrointestinal device including at least one microbe-promoting agent associated with a layered section.

FIGS. 43A-43C illustrate aspects of an embodiment of a gastrointestinal system including a gastrointestinal device and an adjunct for the gastrointestinal device configured to form a layered section. FIG. 43A shows gastrointestinal system 4300 including gastrointestinal device 4310 (e.g., a gastrointestinal sleeve or liner) and adjunct 4320 (e.g., a tubular adjunct). Adjunct 4320 includes a tubular substrate and at least one microbe-promoting agent associated with at least one surface of the substrate. At least one surface of adjunct 4320 including the at least one microbe-promoting agent further includes an adhesive and/or at least one anchor structure configured to attach the at least one surface to a surface of gastrointestinal device 4310. FIG. 43B shows a longitudinal cross-section through a portion of adjunct 4320. Adjunct 4320 includes substrate 4330 (e.g., a tubular substrate) and at least one microbe-promoting agent 4340 (stippled pattern) associated with the outer surface of substrate 4330. FIG. 43C shows a longitudinal cross-section through a portion of gastrointestinal system 4300 including adjunct 4320 attached to an inner surface 4350 of a portion of gastrointestinal device 4310. In an aspect, adjunct 4320 is attached to gastrointestinal device 4310 with an adhesive. In an aspect, adjunct 4320 is attached to gastrointestinal device 4310 with at least one anchoring structure. Adjunct 4320 includes substrate 4330 and at least one microbe-promoting agent 4340 associated with a surface of substrate 4330. Adjunct 4320 is attached to gastrointestinal device 4310 such that the inner surface of the gastrointestinal device 4310 and substrate 4330 form a layered section, the layered section including the at least one microbe-promoting agent 4340 disposed between the inner surface 4350 of gastrointestinal device 4310 and substrate 4330. Substrate 4330 is further formed from a semi-permeable material, allowing for material to transit in (arrows 4360) and transit out (arrows 4370) the portion of the layered section including the at least one microbe-promoting agent 4340. For example, ingested components can transit into the layered section to interact with the at least one microbe-promoting agent and/or the at least one microbe-promoting agent can transit out of the layered section to interact with the ingested components. For example, an ingested at least one type of commensal microbe can transit into the layered section to interact with the at least one microbe-promoting agent and/or the at least one microbe-promoting agent can transit out of the layered section to interact with the ingested at least one type of commensal microbe. In some embodiments, the adjunct forms a layered section on the outer surface of the gastrointestinal device, allowing gastrointestinal components associated with the gastrointestinal wall to transit into the layered section to interact with the at least one microbe-promoting agent and/or the at least one microbe-promoting agent can transit out of the layered section to interact with the components of the gastrointestinal wall.

In an aspect, the substrate of the adjunct includes a patch, sheet, or tubular structure. In an aspect, the substrate of the adjunct includes a flexible patch, sheet, or tubular structure. In an aspect, the substrate of the adjunct is formed from a semi-permeable material. For example, the substrate of the adjunct can be formed from a semi-permeable material that allows for selective transit of materials depending upon size, pH, or hydrophobicity of the materials. In an aspect, the substrate of the adjunct is formed from a substantially impermeable material.

In an aspect, at least a portion of the adjunct includes a degradable material. In an aspect, at least a portion of the adjunct includes a stimulus-responsive degradable material. For example, the stimulus-responsive degradable material can include at least one of a time-responsive degradable material, a moisture-responsive degradable material, a temperature-sensitive degradable material, a pH-responsive degradable material, or a chemical-responsive degradable material. Non-limiting examples of stimulus-responsive materials have been described above herein. In an aspect, the adjunct is noncontiguous. For example, the adjunct can include segments, e.g., segments connected by degradable portions.

The adjunct of the gastrointestinal system includes at least one microbe-promoting agent configured to promote at least one of attraction, colonization, and growth of at least one type of commensal microbe. In an aspect, the at least one microbe-promoting agent is configured to promote at least one of attraction, colonization, and growth of at least one type of commensal gut microbe. In an aspect, the at least one microbe-promoting agent is configured to promote at least one of attraction, colonization, and growth of at least part of a gut microbiota. In an aspect, the at least one microbe-promoting agent is configured to promote at least one of attraction, colonization, and growth of at least one type of endogenous commensal microbe. In an aspect, the at least one microbe-promoting agent is configured to promote at least one of attraction, colonization, and growth of at least one type of administered commensal microbe. In an aspect, the at least one microbe-promoting agent is configured to promote at least one of attraction, colonization, and growth of at least one type of commensal microbe derived from a fecal sample. In an aspect, the at least one microbe-promoting agent is configured to promote at least one of attraction, colonization, and growth of at least one type of genetically engineered microbe. In an aspect, the at least one microbe-promoting agent is configured to promote at least one of attraction, colonization, and growth of at least one type of commensal microbe derived from in vitro culture. In an aspect, the at least one microbe-promoting agent is configured to promote at least one of attraction, colonization, and growth of at least one type probiotic. In an aspect, the at least one microbe-promoting agent is configured to promote at least one of attraction, colonization, and growth of at least one type of commensal microbe beneficial to a subject. In an aspect, the at least one microbe-promoting agent is configured to promote at least one of attraction, colonization, and growth of at least one type of commensal microbe beneficial to at least one of the immune system of the subject, a dietary condition of the subject, or a medical condition of the subject. In an aspect, the at least one microbe-promoting agent is configured to promote formation of a microbiome.

In an aspect, the at least one microbe-promoting agent includes at least one prebiotic agent. For example, the at least one prebiotic agent can include at least one of a mucopolysaccharide, a chitin, a carrageenan, an arabinogalactin, a starch polysaccharide, an oligosaccharide, a fructosaccharide, or inulin. For example, the at least one prebiotic agent can include at least one of a protein, peptide, lipids, nutrients, vitamins, minerals, or salts. In an aspect, the at least one microbe-promoting agent includes a mucus. For example, the mucus can include natural mucus, synthetic mucus, or a combination thereof. In an aspect, the at least one microbe-promoting agent includes a binding agent. In an aspect, the binding agent includes a non-selective binding. For example, the non-selective binding agent can include an adhesive, an absorbent, an adsorbent, of a gel. For example, the non-selective binding agent can include a biomolecule-binding polymer, e.g., poly-L-lysine. In an aspect, the binding agent includes a selective binding agent, e.g., an antibody, an aptamer, a DNA fragment, an RNA fragment, a protein, or a peptide. In an aspect, the at least one microbe-promoting agent includes at least one lectin. In an aspect, the at least one microbe-promoting agent includes at least one chemoattractant.

In an aspect, the at least one microbe-promoting agent forms a gradient on the at least one of the first surface and the second surface of the substrate of the adjunct. In an aspect, at least one first microbe-promoting agent is associated with at least one first portion of the substrate of the adjunct and at least one second microbe-promoting agent is associated with at least one second portion of the substrate of the adjunct. In an aspect, the at least one first microbe-promoting agent and the at least one second microbe-promoting agent form a gradient on the substrate of the adjunct. Non-limiting examples the at least one microbe-promoting agent associated with the substrate of an adjunct for a gastrointestinal device have been described above herein.

In an aspect, the at least one microbe-promoting agent forms a coating on the at least one of the first surface and the second surface of the substrate of the adjunct. In an aspect, the at least one microbe-promoting agent is embedded in the at least one of the first surface and the second surface of the substrate of the adjunct. In an aspect, the at least one microbe-promoting agent is covalently attached to the at least one of the first surface and the second surface of the substrate of the adjunct. In an aspect, the at least one microbe-promoting agent is non-covalently attached to the at least one of the first surface and the second surface of the substrate of the adjunct.

In an aspect, the at least one microbe-promoting agent is incorporated into a coating on the at least one of the first surface and the second surface of the substrate of the adjunct. In an aspect, the at least one microbe-promoting agent is incorporated into a degradable coating on the at least one of the first surface and the second surface of the substrate of the adjunct. In an aspect, the at least one microbe-promoting agent is incorporated into a stimulus-responsive degradable coating on the at least one of the first surface and the second surface of the substrate of the adjunct. For example, the stimulus-responsive degradable coating can include at least one of a time-responsive degradable coating, a moisture-responsive degradable coating, a temperature-responsive degradable coating, a pH-responsive degradable coating, or a chemical-responsive degradable coating. In an aspect, the adjunct of the gastrointestinal system includes at least one first microbe-promoting agent in a first degradable coating and at least one second microbe-promoting agent in a second degradable coating. In an aspect, the first degradable coating and the second degradable coating degrade at different rates.

In some embodiments, the gastrointestinal system further includes at least one therapeutic agent. In an aspect, the at least one therapeutic agent is associated with the gastrointestinal device and/or the adjunct for the gastrointestinal device. Non-limiting examples of therapeutic agents have been described above herein.

In some embodiments, the gastrointestinal system further includes at least one bioactive agent. In an aspect, the at least one bioactive agent is associated with the gastrointestinal device and/or the adjunct for the gastrointestinal device. Non-limiting examples of bioactive agents have been described above herein.

In an aspect, the gastrointestinal system includes at least one of one or more therapeutic agents and one or more bioactive agents associated with the adjunct. In an aspect, the gastrointestinal system includes at least one of a therapeutic agent or a bioactive agent incorporated into a degradable coating associated with the adjunct. In an aspect, the adjunct of the gastrointestinal system includes the at least one microbe-promoting agent in a first degradable coating and at least one of a therapeutic agent or a bioactive agent in a second degradable coating. In an aspect, the first degradable coating and the second degradable coating degrade at different rates.

In an aspect, the gastrointestinal device is sufficiently flexible to be moved through the bends of the gastrointestinal tract without damaging, e.g., perforating, the gastrointestinal wall. For example, the gastrointestinal device is flexible enough to be placed deep within the gastrointestinal tract using a catheter, endoscope, or enteroscope-like device. For example, the gastrointestinal device is flexible enough to be moved through the gastrointestinal tract attached to a device designed to travel through the lumen of the gastrointestinal tract. See, e.g., U.S. Pat. No. 7,998,060 to Ferren et al. titled "Lumen-traveling delivery device," which is incorporated herein by reference. For example, the gastrointestinal device is flexible enough to be moved through the gastrointestinal tract using an endoscope.

In an aspect, the adjunct is attached to the gastrointestinal device prior to placing the gastrointestinal device in the gastrointestinal tract of a subject. For example, an adjunct including an adhesive on at least one surface can be adhered to a surface, e.g., an inner or outer surface, of a gastrointestinal device prior to placement. For example, an adjunct including at least one of an anchor structure (e.g., at least one hook, barb, prong, or the like) can be attached to the gastrointestinal device using the at least one anchor structure. For example, an adjunct can be hooked, clipped, sewn, stapled, or adhered to the gastrointestinal device prior to placement.

In an aspect, the adjunct is attached to a gastrointestinal device that is already resident in the gastrointestinal tract of a subject. For example, the adjunct can be placed using a catheter, endoscope or enteroscope-like device. For example, the adjunct can be placed using a lumen-traveling device. For example, the adjunct including an inflatable or expandable anchor structure can be positioned relative to the gastrointestinal device and the anchor structure inflated or expanded to fix the adjunct in place. For example, the adjunct can be hooked, clipped, sewn, stapled, or adhered to a gastrointestinal device resident in the gastrointestinal tract of a subject.

Methods

Described herein are methods for generating an adjunct for a gastrointestinal device including a plurality of at least one type of commensal microbe, the adjunct for a gastrointestinal device including a substrate, the substrate including a first surface and a second surface, the plurality of the at least one type of commensal microbe associated with at a portion of at least one of the first surface and the second surface of the substrate.

In an aspect, the method includes distributing on at least a portion of at least one of the first surface and the second surface of the substrate the plurality of at least one type of commensal microbe. In an aspect, the method includes distributing the plurality of at least one type of commensal microbe on at least a portion of at least one of the first surface and the second surface of the substrate formed from a semi-permeable material. In an aspect, the method includes distributing the plurality of at least one type of commensal microbe on at least a portion of at least one of the first surface and the second surface of the substrate formed from a substantially impermeable material.

In an aspect, the method includes coating on at least a portion of at least one of the first surface and the second surface of the substrate the plurality of at least one type of commensal microbe. In an aspect, coating includes spraying the at least a portion of the at least one of the inner surface and the outer surface of the substrate with a composition including the plurality of the at least one type of commensal microbe. In an aspect, coating includes dipping the at least a portion of the at least one of the first surface and the second surface of the substrate into a composition including the plurality of the at least one type of commensal microbe. In an aspect, coating includes spreading a composition including the plurality of the at least one type of microbe onto the at least a portion of the at least one of the first surface and the second surface of the substrate.

In an aspect, the method includes distributing on the at least a portion of the at least one of the first surface and the second surface of the substrate the plurality of the at least one type of commensal microbe in a coating material. In an aspect, the method includes distributing on the at least a portion of the at least one of the first surface and the second surface of the substrate the plurality of the at least one type of commensal microbe in at least one of a degradable coating material, a matrix coating material, a fibrous coating material, a hydrogel coating material, or a mucus coating material.

In an aspect, the method includes applying the plurality of the at least one type of commensal microbe and the coating material to the at least a portion of the at least one of the first surface and the second surface of the substrate simultaneously. In an aspect, the method includes applying the plurality of the at least one type of commensal microbe and the coating material to the at least a portion of the at least one of the first surface and the second surface of the substrate simultaneously from a common source, e.g., a reservoir containing the combination. In an aspect, the method includes applying the plurality of the at least one type of commensal microbe and the coating material to the at least a portion of the at least one of the first surface and the second surface of the substrate simultaneously from different sources, e.g., one source, e.g., a first reservoir, providing the plurality of the at least one type of commensal microbe and a second source, e.g., a second reservoir, providing the coating material. In an aspect, method includes applying the plurality of the at least one type of commensal microbe and the coating material to the at least a portion of the at least one of the first surface and the second surface of the substrate sequentially. For example, method can include applying the plurality of the at least one type of commensal microbe first to the at least a portion of the at least one of the first surface and the second surface of the substrate followed by application of the coating material. For example, the method can include applying the plurality of the at least one type of commensal microbe to the at least a portion of the at least one of the first surface and the second surface of the substrate to which a coating material has already been applied.

In an aspect, the method includes distributing on the at least a portion of the at least one of the first surface and the second surface of the substrate the plurality of the at least one type of commensal microbe in a stimulus-responsive coating material (e.g., a time-responsive coating material, a moisture-responsive coating material, a temperature-responsive coating material, a pH-responsive coating material, or a chemical-responsive coating material).

In an aspect, the method further includes coating the at least a portion of the at least one of the first surface and the second surface of the substrate with a coating material (e.g., a degradable coating material, a matrix coating material, a fibrous coating material, a hydrogel coating material, or a mucus coating material). In an aspect, the method includes coating the at least a portion of the at least one of the first surface and the second surface of the substrate with a coating material, and adding the plurality of the at least one type of commensal microbe to the coated portion of the at least one of the first surface and the second surface of the substrate. In an aspect, the method includes coating the at least a portion of the at least one of the first surface and the second surface of the substrate with a non-selective binding material, e.g., an adhesive, an absorbent, an adsorbent, a gel, a matrix, or a biopolymer. In an aspect, the method includes coating the at least a portion of the at least one of the first surface and the second surface of the substrate with a selective-binding agent, e.g., an antibody, an aptamer, an oligonucleotide, ligand, a receptor, or a lectin.

In an aspect, the method includes binding on the at least a portion of the at least one of the first surface and the second surface of the substrate the plurality of the at least one type of commensal microbe. In an aspect, the method includes binding on the at least a portion of the at least one of the first surface and the second surface of the substrate the plurality of the at least one type of commensal microbe with at least one selective binding agent (e.g., an antibody, a protein, a peptide, a DNA fragment, an RNA fragment, a lectin, or an aptamer) or non-selective binding agent (e.g., adhesive, an absorbent, an adsorbent, a gel, or a matrix). For example, the method can include binding the plurality of the at least one type of commensal microbe to an antibody cross-linked to the substrate, the antibody configured to recognize and bind a component of the surface of the at least one type of commensal microbe.

In an aspect, the method includes impregnating the at least a portion of the at least one of the first surface and the second surface of the substrate with the plurality of the at least one type of commensal microbe. For example, the method can include impregnating the first and/or second surface of a porous or fibrous material forming the substrate with the plurality of the at least one type of commensal microbe. In an aspect, the method includes embedding into the at least a portion of the at least one of the first surface and the second surface of the substrate the plurality of the at least one type of commensal microbe. In an aspect, the method includes adsorbing, absorbing, covalently binding, or non-covalently binding to the at least a portion of the at least one of the first surface and the second surface of the substrate the plurality of the at least one type of commensal microbe. In an aspect, the method includes embedding the plurality of the at least one type of commensal microbe into the substrate at the time of manufacture. For example, the plurality of the at least one type of commensal microbe can be incorporated into a polymer during a liquid or gel phase prior to forming a solid phase.

In an aspect, the method includes distributing on the at least a portion of the at least one of the first surface and the second surface of the substrate at least one type of gut microbe. In an aspect, the method includes distributing on the at least a portion of the at least one of the first surface and the second surface of the substrate at least one type of commensal gut microbe. For example, the method can include coating the substrate with a plurality of at least one type of Firmicutes (e.g., one or more representatives of *Lactobacillus*), Bacteroidetes, Actinobacteria (e.g., one or more representatives of *Bifidobacterium*) and/or Proteobacteria.

In an aspect, the method includes distributing on the at least a portion of the at least one of the first surface and the second surface of the substrate at least one type of genetically modified microbe. For example, the method can include coating the substrate with a plurality of a type of microbe genetically modified to produce a specific digestive enzyme or therapeutic agent.

In an aspect, the method includes distributing on the at least a portion of the at least one of the first surface and the second surface of the substrate at least one type of commensal microbe derived from a fecal sample. For example, the method can include distributing on at least one surface of the substrate at least one type of commensal microbe from a fecal sample derived from the subject, a relative, or a healthy donor.

In an aspect, the method includes distributing on the at least a portion of the at least one of the first surface and the second surface of the substrate at least part of a gut microbiota. In an aspect, the method includes distributing on the at least a portion of the at least one of the first surface and the second surface of the substrate at least part of a gut microbiota of the subject. In an aspect, the method includes distributing on the at least a portion of the at least one of the first surface and the second surface of the substrate at least part of a gut microbiota of one or more other individuals. In an aspect, the method includes distributing on the at least a portion of the at least one of the first surface and the second surface of the substrate at least part of a healthy gut microbiota, a preferred gut microbiota, or a theoretical gut microbiota. In an aspect, the method includes distributing on the at least a portion of the at least one of the first surface and the second surface of the substrate at least part of the gut microbiota from a fecal sample. In an aspect, the method includes preparing the at least part of the gut microbiota from in vitro culture of one or more types of gut microbes.

In an aspect, the method includes distributing on the at least a portion of the at least one of the first surface and the second surface of the substrate a phylogentically diverse mini-microbiota. In an aspect, method includes distributing on the at least a portion of the at least one of the first surface and the second surface of the substrate at least one type of probiotic. In an aspect, the method includes distributing on the at least a portion of the at least one of the first surface and the second surface of the substrate at least one type of commensal microbe is beneficial to the subject. In an aspect, the at least one type of commensal microbe is beneficial to at least one of the immune system of the subject, a dietary condition of the subject, or a medical condition of the subject. For example, the method can include distributing on at least one surface of the substrate a plurality of at least one type of genetically modified microbe configured to secrete a digestive enzyme or therapeutic agent beneficial to a condition of the subject. In an aspect, the at least one type of commensal microbe is beneficial to the subject with a *Clostridium difficile* infection. In an aspect, the at least one type of commensal microbe is beneficial to the subject with Crohn's disease.

In an aspect, the method further includes distributing on at least a portion of the at least one of the first surface and the second surface of the substrate at least one of a prebiotic agent, a therapeutic agent, or a bioactive agent. For example, the method can include distributing on at least one surface of the substrate an oligosaccharide prebiotic agent. For example, the method can include distributing on at least one surface of the substrate an antibiotic. For example, the method can include distributing on at least one surface of the substrate a digestive enzyme. In an aspect, the method includes distributing on at least a portion of the at least one of the first surface and the second surface of the substrate at least one of a prebiotic agent, a therapeutic agent, or a bioactive agent in a coating material (e.g., a degradable coating material, a matrix coating material, a fibrous coating material, a hydrogel coating material, a mucus coating material, or a stimulus-responsive coating material).

Described herein are methods for generating an adjunct for a gastrointestinal device including at least one microbe-promoting agent, the adjunct for a gastrointestinal device including a substrate, the substrate including a first surface and a second surface, the at least one microbe-promoting agent associated with at least one of the first surface and the second surface of the substrate, the at least one microbe-promoting agent configured to promote at least one of attraction, colonization, and growth of at least one type of commensal microbe.

In an aspect, the method includes distributing on at least one of the first surface and the second surface of the substrate the at least one microbe-promoting agent. In an aspect, the method includes distributing the at least one microbe-promoting agent on at least one of the first surface and the second surface of the substrate formed from a semi-permeable material. In an aspect, the method includes distributing the at least one microbe-promoting agent on at least one of the first surface and the second surface of the substrate formed from a substantially impermeable material.

In an aspect, the method includes coating on at least one of the first surface and the second surface of the substrate the at least one microbe-promoting agent. In an aspect, coating includes spraying the at least one of the first surface and the second surface of the substrate with a composition including the at least one microbe-promoting agent. In an aspect, coating includes dipping the at least one of the first surface and the second surface of the substrate into a composition including the at least one microbe-promoting agent. In an aspect, coating includes spreading a composition including the at least one microbe-promoting agent onto the at least one of the first surface and the second surface of the substrate.

In an aspect, the method includes distributing on the at least one of the first surface and the second surface of the substrate the at least one microbe-promoting agent in a coating material. In an aspect, the method includes distributing on the at least one of the first surface and the second surface of the substrate the at least one microbe-promoting agent in at least one of a degradable coating material, a matrix coating material, a fibrous coating material, a hydrogel coating material, or a mucus coating material.

In an aspect, the method includes applying the at least one microbe-promoting agent and the coating material to the at least one of the first surface and the second surface of the substrate simultaneously. In an aspect, the method includes applying the at least one microbe-promoting agent and the coating material to the at least one of the first surface and the second surface of the substrate simultaneously from a common source, e.g., a reservoir containing the combination. In an aspect, the method includes applying the at least one microbe-promoting agent and the coating material to the at least one of the first surface and the second surface of the substrate simultaneously from different sources, e.g., a first reservoir, providing the at least one microbe-promoting agent and a second source, e.g., a second reservoir, providing the coating material. In an aspect, method includes applying the at least one microbe-promoting agent and the coating material to the at least one of the first surface and the second surface of the substrate sequentially. For example, method can include applying the at least one microbe-promoting agent first to the at least one of the first surface and the second surface of the substrate followed by application of the coating material. For example, the method can include applying the at least one microbe-promoting agent to the at least one of the first surface and the second surface of the substrate to which a coating material has already been applied.

In an aspect, the method includes distributing on the at least one of the first surface and the second surface of the substrate the at least one microbe-promoting agent in a stimulus-responsive coating material (e.g., a time-responsive coating material, a moisture-responsive coating material, a temperature-responsive coating material, a pH-responsive coating material, or a chemical-responsive coating material).

In an aspect, the method further includes coating the at least one of the first surface and the second surface of the substrate with a coating material (e.g., a degradable coating material, a matrix coating material, a fibrous coating material, a hydrogel coating material, or a mucus coating material). In an aspect, the method includes coating the at least one of the first surface and the second surface of the substrate with a coating material, and adding the at least one microbe-promoting agent to the coated portion of the at least one of the first surface and the second surface of the substrate. In an aspect, the method includes coating the at least one of the first surface and the second surface of the substrate with a non-selective binding material, e.g., an adhesive, an absorbent, an adsorbent, a gel, a matrix, or a biopolymer. In an aspect, the method includes coating the at least one of the first surface and the second surface of the substrate with a selective-binding agent, e.g., an antibody, an aptamer, an oligonucleotide, ligand, a receptor, or a lectin.

In an aspect, the method includes binding on the at least one of the first surface and the second surface of the substrate the at least one microbe-promoting agent. In an aspect, the method includes binding on the at least one of the first surface and the second surface of the substrate the at least one microbe-promoting agent with at least one selective binding agent (e.g., an antibody, a protein, a peptide, a DNA fragment, an RNA fragment, a lectin, or an aptamer) or non-selective binding agent (e.g., adhesive, an absorbent, an adsorbent, a gel, or a matrix).

In an aspect, the method includes impregnating the at least one of the first surface and the second surface of the substrate with the at least one microbe-promoting agent. For example, the method can include impregnating the first and/or second surface of a porous or fibrous material forming the substrate with the at least one microbe-promoting agent. In an aspect, the method includes embedding into the at least one of the first surface and the second surface of the substrate the at least one microbe-promoting agent. In an aspect, the method includes adsorbing, absorbing, covalently binding, or non-covalently binding to the at least one of the first surface and the second surface of the substrate the at least one microbe-promoting agent. In an aspect, the method includes embedding the at least one microbe-promoting agent into the substrate at the time of manufacture. For example, the at least one microbe-promoting agent can be incorporated into a polymer during a liquid or gel phase prior to forming a solid phase.

In an aspect, the method includes distributing on the at least one of the first surface and the second surface of the substrate at least one microbe-promoting agent configured to promote at least one of attraction, colonization, and growth of at least one type of commensal gut microbe. In an aspect, the method includes distributing on the at least one of the first surface and the second surface of the substrate at least one microbe-promoting agent configured to promote at least one of attraction, colonization, and growth of at least part of a gut microbiota. In an aspect, the method includes distributing on the at least one of the first surface and the second surface of the substrate at least one microbe-promoting agent configured to promote at least one of attraction, colonization, and growth of at least one type of endogenous commensal microbe. In an aspect, the method includes distributing on the at least one of the first surface and the second surface of the substrate at least one microbe-promoting agent configured to promote at least one of attraction, colonization, and growth of at least one type of administered commensal microbe. In an aspect, the method includes distributing on the at least one of the first surface and the second surface of the substrate at least one microbe-promoting agent configured to promote at least one of attraction, colonization, and growth of at least one type of commensal microbe derived from a fecal sample. In an aspect, the method includes distributing on the at least one of the first surface and the second surface of the substrate at least one microbe-promoting agent configured to promote at least one of attraction, colonization, and growth of at least one type of genetically engineered microbe. In an aspect, the method includes distributing on the at least one of the first surface and the second surface of the substrate at least one microbe-promoting agent configured to promote at least one of attraction, colonization, and growth of at least one type of commensal microbe derived from in vitro culture. In an aspect, the method includes distributing on the at least one of the first surface and the second surface of the substrate at least one microbe-promoting agent configured to promote at least one of attraction, colonization, and growth of at least one type of probiotic. In an aspect, the method includes distributing on the at least one of the first surface and the second surface of the substrate at least one microbe-promoting agent configured to promote at least one of attraction, colonization, and growth of a phylogenetically diverse mini-microbiota.

In an aspect, the method includes distributing on at least one of the first surface and the second surface of the substrate at least one microbe-promoting agent configured to promote at least one of attraction, colonization, and growth of at least one type of commensal microbe beneficial to the subject. In an aspect, the method includes distributing on at least one of the first surface and the second surface of the substrate at least one microbe-promoting agent configured to promote at least one of attraction, colonization, and growth of at least one type of commensal microbe beneficial to at least one of the immune system of the subject, a dietary condition of the subject, or a medical condition of the subject. In an aspect, the method includes distributing on at least one of the first surface and the second surface of the substrate at least one microbe-promoting agent configured to promote at least one of attraction, colonization, and growth of at least one type of commensal microbe beneficial to the subject with a *Clostridium difficile* infection. In an aspect, the method includes distributing on at least one of the first surface and the second surface of the substrate at least one microbe-promoting agent configured to promote at least one of attraction, colonization, and growth of at least one type of commensal microbe beneficial to the subject with Crohn's disease.

In an aspect, the method includes distributing on at least one of the first surface and the second surface of the substrate at least one microbe-promoting agent configured to promote formation of a microbiome. For example, the at least one microbe-promoting agent can be configured to promote formation of a healthy microbiome or preferred microbiome. The microbiome can include the environment as well as microbes associated with the environment. For example, the at least one microbe-promoting agent directly promote attraction, colonization, and/or growth of microbes associated with a microbiome. For example, the at least one microbe-promoting agent can indirectly promote attraction, colonization, and/or growth of microbes associated with a microbiome by altering the environment, e.g., the pH of the environment.

In an aspect, the method includes distributing on at least one of the first surface and the second surface of the substrate at least one prebiotic agent. For example, the at least one prebiotic agent can include inulin. Non-limiting examples of prebiotic agents have been described above herein. In an aspect, the method includes distributing on to at least one of the first surface and the second surface of the substrate a mucus. For example, the at least one microbe-promoting agent can include natural mucus, synthetic mucus, or a combination thereof. In an aspect, the method includes distributing on at least one of the first surface and the second surface of the substrate at least one a binding agent. For example, the at least one microbe-promoting agent can include an antibody or an aptamer that recognizes and binds at least one type of commensal microbe. In an aspect, the method includes distributing on to at least one of the first surface and the second surface of the substrate at least one lectin. For example, the at least one microbe-promoting agent can include mannan-binding lectin for interaction with D-mannose and/or L-fucose residues on microbes, including intestinal pathogens such as *Salmonella*.

In an aspect, the method further includes distributing on at least one first portion of the substrate at least one first microbe-promoting agent and distributing on at least one second portion of the substrate at least one second microbe-promoting agent.

In an aspect, the method includes distributing on at least one of the first surface and the second surface of the substrate at least one therapeutic agent. For example, the method can include distributing on at least one surface of the substrate an antibiotic or anti-inflammatory agent. Non-limiting example of therapeutic agents have been described above herein. In an aspect, the method includes distributing on at least a portion of at least one of the first surface and the second surface of the substrate at least one first therapeutic agent and at least one second therapeutic agent. In an aspect, the method includes distributing on at least one of the first surface and the second surface of the substrate at least one therapeutic agent in a coating material (e.g., a degradable coating material, a matrix coating material, a fibrous coating material, a hydrogel coating material, a mucus coating material, or a stimulus-responsive coating material).

In an aspect, the method includes distributing on at least one of the first surface and the second surface of the substrate at least one bioactive agent. For example, the method can include distributing on at least one surface of the substrate a digestive enzyme. Non-limiting examples of bioactive agents have been described above herein. In an aspect, the method includes distributing on at least a portion of at least one of the first surface and the second surface of the substrate at least one first bioactive agent and at least one second bioactive agent. In an aspect, the method includes distributing on at least one of the first surface and the second surface of the substrate at least one bioactive agent in a coating material (e.g., a degradable coating material, a matrix coating material, a fibrous coating material, a hydrogel coating material, a mucus coating material, or a stimulus-responsive coating material).

Described herein are methods for generating an adjunct for a gastrointestinal device including a substrate with a layered wall. In an aspect, the layered wall includes a first layer formed from a first material, a second layer formed from a second material, and an internal space disposed between the first layer and the second layer. In an aspect, the internal space includes a plurality of at least one type of commensal microbe. In an aspect, the internal space includes at least one microbe-promoting agent.

In some embodiments, the method includes distributing on one surface of a first material a plurality of at least one type of commensal microbe and applying a second material over the plurality of the at least one type of commensal microbe. Non-limiting aspects of commensal microbes have been described above herein. In other embodiments, the method includes distributing on one surface of a first material a plurality of at least one microbe-promoting agent and applying a second material over the at least one microbe-promoting agent. Non-limiting aspects of microbe-promoting agents have been described above herein. In an aspect, at least one of the first material and the second material includes a semi-permeable material. In an aspect, at least one of the first material and the second material includes a selectively permeable material. In an aspect, the selectively permeable material is selectively permeable based on size, hydrophobicity, or charge. In an aspect, the first material includes a first semi-permeable material and the second material includes a second semi-permeable material. In an aspect, the first semi-permeable material differs from the second semi-permeable material. For example, the first semi-permeable material can differ from the second semi-permeable material based on selectivity to size, hydrophobicity, or charge.

In some embodiments, the method includes coating the one surface of the first material with the plurality of the at least one type of commensal microbe. In other embodiments, the method includes coating the one surface of the first material with the at least one microbe-promoting agent. In an aspect, coating includes spraying, dipping, or spreading a composition including the plurality of the at least one type of commensal microbe or the at least one microbe-promoting agent on the one surface of the first material. In an aspect, the method includes distributing on the one surface of the first material the plurality of the at least one type of commensal microbe or the at least one microbe-promoting agent in a coating material (e.g., a degradable coating material, a matrix coating material, a fibrous coating material, a porous coating material, a gel coating material, or a mucus coating material). In an aspect, the method includes distributing on the one surface of the first material the plurality of the at least one type of commensal microbe or the at least one microbe-promoting agent in a stimulus-responsive coating material (e.g., a time-responsive coating material, a moisture-responsive coating material, a temperature-responsive coating material, a pH-responsive coating material, or a chemical-responsive coating material).

In some embodiments, the method includes binding to the one surface of the first material the plurality of the at least one type of commensal microbe. In other embodiments, the method includes binding to the one surface of the first material the at least one microbe-promoting agent. In an aspect, the method includes binding the plurality of the at least one type of commensal microbe or the at least one microbe-promoting agent to the one surface of the first material with at least one non-selective binding (e.g., adhesive, an absorbent, an adsorbent, a gel, or a matrix agent) or selective binding agent (e.g., an antibody, a protein, a peptide, a DNA fragment, an RNA fragment, a lectin, or an aptamer).

In some embodiments, the method includes impregnating into the one surface of the first material the plurality of the at least one type of commensal microbe. In some embodiments, the method includes impregnating into the one surface of the first material the at least one microbe-promoting agent. In some embodiments, the method includes embedding into the one surface of the first material the plurality of the at least one type of commensal microbe. In some embodiments, the method includes embedding into the one surface of the first material the at least one microbe-promoting agent. In an aspect, the method includes adsorbing, absorbing, covalently binding, or non-covalently binding onto the one surface of the first material the plurality of the at least one type of commensal microbe or the at least one microbe-promoting agent. In an aspect, the method further includes embedding the plurality of the at least one type of commensal microbe or the at least one microbe-promoting agent into the substrate at the time of manufacture.

In an aspect, the method further includes distributing on a surface of the first material at least one of a prebiotic agent, a therapeutic agent, or a bioactive agent.

In an aspect, the method includes applying a second material over the plurality of the at least one type of commensal microbe to form substrate with a layered wall. In an aspect, the method includes applying a second material over the at least one microbe-promoting agent to form a substrate with a layered wall. In an aspect, the method includes applying a second material that is substantially identical to the first material. In an aspect, the method includes applying a second material with a permeability property that differs from a permeability property of the first material. In an aspect, the permeability property includes at least one of a sized-based permeability property, a charge-based permeability property, a pH-based permeability property, or a hydrophobicity-based permeability property.

In an aspect, the method further includes attaching the first material including the plurality of the at least one type of commensal microbe or the at least one microbe-promoting agent to the second material. In an aspect, the method includes adhering (e.g., gluing) the first material to the second material. In an aspect, the method includes stapling the first material to the second material. In an aspect, the method includes stitching the first material to the second material. In an aspect, the method includes fusing the first material to the second material. For example, the first material can be fused in one or more positions along the length of the substrate using pressure, heat, or a chemical.

In an aspect, the method further includes distributing on at least one surface of the second material at least one of a prebiotic agent, a therapeutic agent, or a bioactive agent.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "operably coupled to" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components can be referred to herein as "configured to," "configured by," "configurable to," "operable/operative to," "adapted/adaptable," "able to," "conformable/conformed to," etc. Those skilled in the art will recognize that such terms (e.g. "configured to") can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications can be made without departing from the subject matter described herein and its broader aspects and, therefore, the appended claims are to encompass within their scope all such changes and modifications as are within the true spirit and scope of the subject matter described herein.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

Various non-limiting embodiments are described herein as Prophetic Examples.

PROPHETIC EXAMPLE 1

An Adjunct for a Gastrointestinal Device Including Microbes, to Treat an Inflammatory Bowel Disease An adjunct for a gastrointestinal device is designed for use with a gastrointestinal device of a type configured to treat patients with an inflammatory bowel disease (IBD) and resulting inflamed section of colon. The adjunct for a gastrointestinal device comprises a tubular substrate, e.g., a sleeve, and an anchor structure configured to attach the adjunct for a gastrointestinal device, e.g., a gastric stent, anchored in the transverse colon of an IBD patient. The adjunct is constructed for insertion into the gastric stent. At least one surface of the tubular substrate of the adjunct is coated with a set of microbes that approximates the microbiota at the site in a healthy subject and aids in protecting the inflamed section of the transverse colon of an IBD patient, providing microbial functions at the site and replenishing the microbiota of nearby tissues.

Tubular substrate of the adjunct is formed from a biocompatible semipermeable membrane, for example, polyethylene-co-vinyl acetate (PEVA) (available from Polysciences, Inc., Warrington, Pa.; see PEVA info sheet). Methods and materials to manufacture semipermeable membranes with a desired porosity and physical properties (e.g., flexibility, tensile strength and biocompatibility) are described (see e.g., Handbook of Membrane Separations: Chemical, Pharmaceutical, Food, and Biotechnological Applications, edited by Anil K. Pabby, Syed S. H. Rizvi, Ana Maria Sastre, 2009, CRC Press, Boca Raton, Fla., which is incorporated herein by reference). The tubular substrate formed from the biocompatible semipermeable membrane includes pores approximately 20 µm in diameter.

The adjunct further includes an anchor structure at the proximal end of the tubular structure that is configured to hold the tubular structure in place in conjunction with the gastric stent. The anchor structure is cast from PEV at the time of device manufacture, and is shaped like an umbrella that expands after placement of the adjunct into the gastric stent by colonoscopy. Anchors to retain tubular structures are described (see e.g., U.S. Patent Appl. No. 2013/0281911 by Babkes et al. published on Oct. 24, 2013, which is incorporated herein by reference).

The inner surface of the tubular substrate of the adjunct is coated with microbes that are normally associated with a healthy transverse colon. The microbes include Firmicutes (including at least one *Lactobacillus*), Bacteroidetes, Actinobacteria (including *Bifidobacterium*) and/or Proteobacteria in a desired ratio that is determined based on data including the patient's characteristics such as age, ethnicity, and location, as well as population data. The microbes function as they would in a healthy colon by further digesting the chyme to release nutrients and preparing the chyme for downstream digestion. The microbes further aid in re-establishing and replenishing microbes at the affected site as well as nearby and downstream regions of the colon. The microbes are encapsulated in a coating to support continued health of the microbes, and to allow exposure to the chyme. The coating is formed of a hydrogel made of a synthetic monomer, for example polyethylene glycol diacrylate/dimethacrylate (PEGDA/PEGDMA), as described in Lin & Metters (2006), ibid, and includes the synthetic mucin MUC2.

The outer surface of the tubular substrate of the adjunct is coated with degradable coating that can release microbes over time. For example, PLGA (polylactic coglycolic acid) may be used to encapsulate the commensal microbes and to coat the regions of the outer surface of the sleeve. Fabrication techniques and polymer compositions for PLGA biodegradable carriers are described (see e.g., Makadia et al., *Polymers* 3: 1377-1397, 2011, which is incorporated herein by reference). The ratio of lactic acid to glycolic acid in the PLGA is adjusted to control the rate of PLGA degradation and release of the microbes. For example PLGA composed of 85% lactic acid and 15% glycolic acid biodegrades and releases its contents starting on day 22 following implantation and completes release by approximately day 110 (see e.g., Makadia et al., Ibid.). Microbes needed to reestablish a healthy microbiome for IBD patients may be identified for individual patients or from group studies. IBD patients display abnormal microbiota, or dysbiosis, with depletion of some phyla and overrepresentation of others. For example, IBD patient's microbiota may contain elevated numbers of injurious bacteria belonging to Proteobacteria and Actinobacteria phyla while protective bacteria from Firmicutes are underrepresented (see e.g., Wu and Lewis, *Clin. Gastroent. Hepatol.* 11: 774-777, 2013, which is incorporated herein by reference). Thus, the tubular substrate is coated on the outer surface (facing the intestinal wall) with PLGA containing Firmicutes *Fecalibacterium prauzsnitzii*.

PROPHETIC EXAMPLE 2

An Adjunct for a Gastrointestinal Device, Including Fecal Microbiota, for Treatment of Recurrent *Clostridium Difficile* Infection An adjunct for a gastrointestinal device is manufactured with microbes isolated from fecal transplants embedded in a degradable polymer, and used to treat recurrent or relapsing *Clostridium difficile* infections (CDI). The adjunct includes a substrate formed from a biodegradable polymer, which degrades and releases fecal microbes. The adjunct is designed as a patch with an adhesive that holds the adjunct for a gastrointestinal device, e.g., a gastric stent, until substrate undergoes biodegradation and is excreted. The adjunct is designed to provide beneficial fecal microbiota to reestablish a healthy microbiome and correct the dysbiosis that occurs in CDI.

The substrate of the adjunct is manufactured from a biodegradable polymer as a rectangular patch. The patch may be formed from a degradable polymer by casting or extrusion as a strip, for example a strip approximately 5 cm long and 1 cm wide. Semipermeable, biodegradable polymers are described (see, e.g., Pal et al., *Designed Monomers and Polymers* 12:197-220, 2009, which is incorporated herein by reference). The rate of degradation of a copolymer may be controlled by adjusting the molar ratio of the monomers (see, e.g., Makadia et al., *Polymers* 3: 1377-1397, 2011 and Kong, et al., *Biomacromolecules* 5: 1720-1727, 2004, which are incorporated herein by reference). For example, a copolymer composed of 85% lactic acid and 15% glycolic acid biodegrades and releases its contents starting on day 22 following implantation and completes release by approximately day 110 (see e.g., Makadia et al., Ibid.). At least one surface of the substrate includes an adhesive, e.g., a surgical adhesive.

The adjunct is manufactured with fecal microbiota embedded in the biodegradable patch. Fecal material is obtained from healthy donors and prepared by dilution, homogenization, and filtration according to established protocols (see e.g., Bakken et al., *Clin. Gastroenterol. Hepatol.* 9: 1044-1049, 2011, which is incorporated herein by reference).

Fecal microbiota donors are screened for HIV, Hepatitis B or Hepatitis C infections, risky behavior, exposure to traveler's diarrhea, Creutzfeldt-Jakob disease, gastrointestinal disease (e.g., IBD, chronic diarrhea or constipation), and factors that may affect an individual's microbiome (e.g., antibiotics, and immunosuppressive medications such as glucocorticoids, biologics). Microbiota donors are excluded if they have had gastric bypass surgery, metabolic syndrome, systemic autoimmunity, atopic disease, or fibromyalgia. Also donor stools are tested for *Clostridium difficile* toxins by PCR or immunoassay, enteric pathogens, fecal *Giardia* antigen, and *Cryptosporidium*.

Fecal microbes are obtained from approximately 50 grams of feces using a combination of dilution in saline, homogenization, filtration and centrifugation. The microbes are concentrated and suspended in 10% glycerol in saline and stored frozen at −80 degrees C. Microbe sample aliquots obtained from 50 grams of feces are typically used for a fecal transplant (see, e.g., Hamilton et al., *Gut Microbes* 4: 125-135, 2013, which is incorporated herein by reference). However, the adjunct may contain multiple aliquots of microbes to be released from the device over an extended period, e.g., 110 days. The adjunct is constructed with fecal microbiota embedded in sodium alginate. Methods to extrude alginate and to encapsulate intestinal bacteria in alginate are described (see e.g., Lotfipour et al., *Advanced Pharmaceutical Bulletin* 2: 71-78, 2012, which is incorporated herein by reference). Moreover, the rate of degradation of alginate hydrogels can be modified using oxidized, low MW alginates. The degradation rate of alginate hydrogels for in vivo use is altered to deliver microbes on a preferred timescale without changing elasticity or gel formation (see, e.g., Kong, et al., *Biomacromolecules* 5: 1720-1727, 2004, which is incorporated herein by reference). The adjunct may be fabricated with layers of different alginate hydrogels having different degradation rates. For example, following implantation of the adjunct the outer layer of alginate may degrade and release fecal microbes from days 7-10, and then an inner layer may degrade at a later time, e.g., from days 30-36.

PROPHETIC EXAMPLE 3

An Adjunct for a Gastrointestinal Device, with Microbial Coating, for Treating Obese Patients An adjunct for a gastrointestinal device is described that includes a substrate and microbial coatings to treat obese patients. The adjunct is configured for attachment to an inner surface of gastrointestinal device, e.g., a gastric liner. The gastric liner is configured to restrict caloric intake by preventing digestion and absorption of nutrients until they have passed the duodenum. The microbial coating on the surface of the adjunct supplies microbes that function in place of the natural flora that normally reside in the section of the digestive tract covered by the gastrointestinal device.

The adjunct includes a flexible tubular structure, e.g., a sleeve, composed of an impermeable membrane and includes an anchor structure at the proximal end and a microbial coating. A biocompatible polymer, for example expanded polytetrafluoroethylene (ePTFE), with a thickness of approximately 0.001 inches is used to make a sleeve about 25 cm in length with a diameter ranging between 10 mm and 35 mm. The sleeve extends the length from the stomach through the pyloric sphincter and through the duodenum to the jejunum. Methods to manufacture a cylindrical flexible tube have been described. For example, an impermeable sleeve may be made by extrusion of ePTFE into a tube form and expansion of sections to fill differing intestinal diameters (see e.g., U.S. Patent Application No. 2012/0184893 by Thompson et al. published on Jul. 19, 2012, which is incorporated herein by reference). The sleeve is constructed with an expandable anchor at the proximal end, which retains the proximal end of the sleeve upstream of the proximal end of the gastric liner into which it will be inserted. The expandable anchor, fabricated out of a polymer (e.g., PTFE), is approximately 10 to 30 mm in outside diameter. Methods to manufacture the expandable anchor, which may include laser cutting, and heat setting are described (see e.g., U.S. Patent No. 2012/0184893, ibid.).

The inner surface of the sleeve of the adjunct is coated with microbes that are normally associated with a healthy gut, as described below, and may include *Clostridium, Streptococcus, Escherichia*, Firmicutes, Bacteroidetes, Actinobacteria and/or Proteobacteria. The microbes are arranged along the inside surface in a gradient of changing ratio that reflect the changes along the normal digestive lumen at the site of implantation. The ratios can be determined based on data including the patient's characteristics such as age, ethnicity, and location, as well as population data. The microbes function as they would in a healthy intestine by digesting the chyme and preparing it for further processing downstream. The microbes are encapsulated in a coating to support continued health of the microbes and to allow exposure to the chyme. The coating is formed of a hydrogel made of a synthetic monomer, for example polyethylene glycol diacrylate/dimethacrylate (PEGDA/PEGDMA), as described in Lin & Metters (2006), ibid, and includes the synthetic mucin MUC2.

PROPHETIC EXAMPLE 4

An Adjunct for a Gastrointestinal Device, with Microbial Coating, for Treatment of Obese Patients An adjunct for a gastrointestinal device is described that includes a substrate and microbial coating to treat obese patients. The adjunct is configured for attachment to an outer surface of gastrointestinal device, e.g., a gastric liner. The gastric liner is configured to restrict caloric intake by preventing digestion and absorption of nutrients until they have passed the duodenum. The microbial coating on the outside surface of the adjunct supplies microbes to the gastrointestinal tract to promote a healthy microbiome. The microbial coating on the outside surface of the adjunct includes a degradable polymer that releases microbes in a time-dependent fashion.

The adjunct includes a flexible tubular structure, e.g., a sleeve, composed of an impermeable membrane and includes a microbial coating on the outer surface of the sleeve and an adhesive on at least a portion of the inner surface of the sleeve. A biocompatible polymer, for example expanded polytetrafluoroethylene (ePTFE), with a thickness of approximately 0.001 inches is used to make an adjunct sleeve about 25 cm in length with a diameter ranging between 10 mm and 35 mm. The adjunct sleeve is configured to attach to and extend the length of the outer portion of a gastrointestinal device, e.g., a gastric liner, from the stomach through the pyloric sphincter and through the duodenum to the jejunum. Methods to manufacture a cylindrical flexible tube have been described. For example, an impermeable sleeve may be made by extrusion of ePTFE into a tube form and expansion of sections to fill differing intestinal diameters (see e.g., U.S. Patent Application No. 2012/0184893 by Thompson et al. published on Jul. 19, 2012, which is incorporated herein by reference). At least a portion of the inner surface of the sleeve is coated with a pressure-sensitive adhesive, e.g., a styrene copolymer pressure-sensitive adhesive, such that when the sleeve is pulled over the gastric liner, the sleeve can be adhered to the outside surface of the gastric liner. In this configuration, the outer surface of the adjunct including the coating of microbes faces the gastrointestinal wall.

Microbes are coated on the outside surface of the sleeve in a degradable polymer designed to release microbes to correct imbalances in microbiota associated with obesity and metabolic dysfunction. Microbiome changes at the level of bacterial phyla (e.g., reduced numbers of Bacteroidetes and increased numbers of Firmicutes) are associated with obesity and metabolic dysfunction (see e.g., Tilg and Kaiser, *J. Clin. Invest.* 121:2126-2132, 2011, which is incorporated herein by reference). Conversely weight loss in obese animals is associated with increased populations of Proteobacteria (*Escherichia*) and Verrucomicrobia (see e.g., Cox and Blaser, *Cell Metab.* 17: 883-894, 2013, which is incorporated herein by reference). Thus, to treat obese patients, the microbial coating contains, for example, $10^6$ to $10^{10}$ Bacteroidetes, Proteobacteria and Verrucomicrobia, which are suspended in a biocompatible, degradable polymer, e.g., PLGA (polylactic coglycolic acid) and coated onto the outer surface of the sleeve. Administration and dosing of microbes are described (see, e.g., U.S. Pat. No. 7,101,565 to Monte titled "Probiotic/Prebiotic Composition and Delivery Method," which is incorporated herein by reference). Fabrication techniques and polymer compositions for PLGA degradable carriers are described (see e.g., Makadia et al., *Polymers* 3: 1377-1397, 2011, which is incorporated herein by reference). The ratio of lactic acid to glycolic acid in the PLGA is adjusted to control the rate of PLGA degradation and release of the bacteria. For example PLGA composed of 85% lactic acid and 15% glycolic acid biodegrades and releases its contents starting on day 22 following implantation, and completes release by approximately day 110 (see e.g., Makadia et al., Ibid.).

PROPHETIC EXAMPLE 5

An Adjunct for a Gastrointestinal Device, and Microbe-Promoting Agents to Treat Inflammatory Bowel Disease An adjunct for a gastrointestinal device is designed for use with a gastrointestinal device of a type configured to treat patients with an inflammatory bowel disease (IBD) and resulting inflamed section of colon. The adjunct for a gastrointestinal device comprises a tubular substrate, e.g., a sleeve, and an anchor structure configured to attach the adjunct for a gastrointestinal device, e.g., a gastric stent, anchored in the transverse colon of an IBD patient. The adjunct is constructed for insertion into the gastric stent. At least one surface of the tubular substrate of the adjunct is coated with at least one microbe-promoting agent configured to promote attraction, colonization, and growth of at least one type of commensal microbe and aids in protecting the inflamed section of the transverse colon, providing microbial functions at the site and replenishing the microbiota of nearby tissues.

Tubular substrate of the adjunct is formed from a biocompatible semipermeable membrane, for example, polyethylene-co-vinyl acetate (PEVA) (available from Polysciences, Inc., Warrington, Pa.; see PEVA info sheet). Methods and materials to manufacture semipermeable membranes with a desired porosity and physical properties (e.g., flexibility, tensile strength and biocompatibility) are described (see e.g., Handbook of Membrane Separations: Chemical, Pharmaceutical, Food, and Biotechnological Applications, edited by Anil K. Pabby, Syed S. H. Rizvi, Ana Maria Sastre, 2009, CRC Press, Boca Raton, Fla., which is incorporated herein by reference). The tubular substrate formed from the biocompatible semipermeable membrane includes pores approximately 20 µm in diameter.

The adjunct further includes an anchor structure at the proximal end of the tubular structure and is configured to hold the tubular structure in place in conjunction with the gastric stent. The anchor structure is cast from PEV at the time of device manufacture, and is shaped like an umbrella that expands after placing the adjunct into the gastric stent by colonoscopy. Anchors to retain tubular structures are described (see e.g., U.S. Patent Appl. No. 2013/0281911 by Babkes et al. published on Oct. 24, 2013, which is incorporated herein by reference).

The inner surface of the tubular substrate of the adjunct is coated with at least one microbe-promoting agent configured to promote the attraction, colonization, and growth of commensal microbes that are normally associated with a healthy transverse colon. The microbes within the device can then function as they would in a healthy colon by further digesting the chyme to release nutrients and prepare the chyme for downstream digestion. The microbes further aid in re-establishing and replenishing microbes at the affected site as well as nearby and downstream regions of the colon. The microbe-promoting agents are encapsulated in a coating to support continued health of the microbes and to allow exposure to the chyme. The coating is formed of a hydrogel made of a synthetic monomer, for example polyethylene glycol diacrylate/dimethacrylate (PEGDA/PEGDMA), as described in Lin & Metters (2006). Microbe-promoting agents encapsulated in the hydrogel can include at least one chemoattractant, e.g., serine or alpha-methyl-DL-aspartate, for attraction; prebiotics and nutrients for bacterial growth, as described below; and matrix proteins, including mucins, for support. Microbe-promoting agents can include bacterial or mammalian cells, e.g., goblet cells and/or genetically engineered cells, that provide the promoting environment and/or produce the chemoattractant, growth nutrients, or matrix proteins. Microbe-promoting agents are chosen and distributed in a pattern on the tubular substrate depending on the microbial distribution desired based on informational data regarding the patient, such as age, gender, and diet, as well as on populational data. Degradable coatings as described below can be included in the coating of the inner sleeve to release a microbe-promoting agent, e.g., a chemoattractant.

The outer surface tubular substrate of the adjunct is coated with at least one microbe-promoting agent, for example at least one prebiotic agent, to restore a healthy microbiome to the intestine of the IBD patient. Degradable coatings that release prebiotic agents over time into the intestine are used to coat the outside surface of the tubular substrate. For example, PLGA (polylactic coglycolic acid) may be used to encapsulate prebiotics and to coat the outer surface of the tubular substrate. Fabrication techniques and polymer compositions for PLGA biodegradable carriers are described (see e.g., Makadia et al., *Polymers* 3: 1377-1397, 2011, which is incorporated herein by reference). The ratio of lactic acid to glycolic acid in the copolymer, PLGA, is adjusted to control the rate of PLGA degradation and release of the prebiotic agents. For example PLGA composed of 85% lactic acid and 15% glycolic acid biodegrades and releases its contents starting on day 22 following implantation and completes release by approximately day 110 (see e.g., Makadia et al., Ibid.

The microbe-promoting agents coating the inner surface and outer surface of the tubular substrate include prebiotic agents to promote growth of preferred microbes in the endogenous microflora, as well as orally administered bacteria of the Firmicutes species. The prebiotics oligofructose and inulin are carbohydrates that promote the growth of preferred bacteria and lead to production of short chain fatty acids (e.g., butyric acid), which reduce inflammation. For example, PLGA containing oligofructose and inulin is distributed on inner and/or outer surface of the tubular substrate to promote the growth of beneficial bacteria (e.g., Lactobacilli and Bifidobacteria) and to stimulate the production of butryric acid, which reduces inflammation in the colonic mucosa (see e.g., Damaskos and Kollos, *Brit. J. Clin. Pharm.* 65: 453-467, 2008, which is incorporated herein by reference).

All of the above U.S. patents, U.S. patent application publications, U.S. patent applications, foreign patents, foreign patent applications and non-patent publications referred to in this specification and/or listed in any Application Data Sheet, are incorporated herein by reference, to the extent not inconsistent herewith.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A gastrointestinal system, comprising:
   a gastrointestinal sleeve sized for placement in a portion of the gastrointestinal tract of a subject; and
   an adjunct device comprising a patch, sheet, or tube sized to attach to an inner surface or an outer surface of the gastrointestinal sleeve, the adjunct device including
      a flexible tubular structure having
         an inner surface and an outer surface;
         a proximal end and a distal end forming a flow conduit through the flexible tubular structure;
         a stimulus-responsive degradable material associated with at least one of the inner surface and the outer surface of the flexible tubular structure of the removable adjunct device, the stimulus-responsive degradable material responsive to an ingested chemical carried in chyme; and
         a plurality of at least one type of commensal microbe embedded in the stimulus-responsive degradable material associated with the at least one of the inner surface or the outer surface of the flexible tubular structure of the adjunct device, wherein the at least one type of commensal microbe is releasable from the stimulus-responsive degradable material in response to the ingested chemical carried in the chyme;
      at least one anchor structure connected to the flexible tubular structure of the adjunct device and configured to attach the adjunct device to the inner surface or the outer surface of the gastrointestinal sleeve; and
      an adhesive on the inner surface or the outer surface of the flexible tubular structure configured to anchor the adjunct device to the inner surface or the outer surface of the gastrointestinal sleeve.

2. The gastrointestinal system of claim 1, wherein the adjunct device is configured to attach to the gastrointestinal sleeve prior to placement of the gastrointestinal sleeve into the gastrointestinal tract of the subject.

3. The gastrointestinal system of claim 1, wherein the adjunct device is configured to attach to the gastrointestinal sleeve during placement of the gastrointestinal sleeve into the gastrointestinal tract of the subject.

4. The gastrointestinal system of claim 1, wherein the adjunct device is configured to attach to the gastrointestinal sleeve after placement of the gastrointestinal sleeve into the gastrointestinal tract of the subject.

5. The gastrointestinal system of claim 1, wherein the stimulus-responsive degradable material and the plurality of the at least one type of commensal microbe embedded therein are associated with the outer surface of the flexible tubular structure of the removable adjunct device; and wherein the flexible tubular structure of the adjunct device is formed from a sheet of semi-permeable material that is selectively permeable to the ingested chemical carried in the chyme.

6. The gastrointestinal system of claim 1, wherein at least one of the flexible tubular structure or the at least one anchor structure of the adjunct device is formed from a degradable material.

7. The gastrointestinal system of claim 1, wherein the plurality of the at least one type of commensal microbe embedded in the stimulus-responsive degradable material includes a plurality of at least one type of gut microbe embedded in the stimulus-responsive degradable material.

8. The gastrointestinal system of claim 1, wherein the plurality of the at least one type of commensal microbe embedded in the stimulus-responsive degradable material includes a plurality of at least one type of genetically modified microbe embedded in the stimulus-responsive degradable material.

9. The gastrointestinal system of claim 1, wherein the plurality of the at least one type of commensal microbe embedded in the stimulus-responsive degradable material includes at least one type of probiotic embedded in the stimulus-responsive degradable material.

10. The gastrointestinal system of claim 1, further comprising at least one prebiotic agent in a degradable coating associated with at least one of the inner surface and the outer surface of the flexible tubular structure of the adjunct device.

11. The gastrointestinal system of claim 1, wherein the flexible tubular substrate of the adjunct device is formed from a sheet of degradable material.

12. The gastrointestinal system of claim 1, wherein the flexible tubular substrate of the adjunct device is formed from two or more noncontiguous segments connected by at least one degradable linker.

13. The gastrointestinal system of claim 1, wherein the stimulus-responsive degradable material and the plurality of the at least one type of commensal microbe embedded therein form a coating on the at least one of the inner surface and the outer surface of the flexible tubular structure of the adjunct device.

14. The gastrointestinal system of claim 1, wherein the flexible tubular structure of the adjunct device is formed from a sheet of the stimulus-responsive degradable material and the plurality of the at least one type of commensal microbe is embedded therein.

15. The gastrointestinal system of claim 1, wherein the plurality of the at least one type of commensal microbe embedded in the stimulus-responsive degradable material includes a plurality of at least one type of commensal microbe from a fecal sample embedded in the stimulus-responsive degradable material.

16. The gastrointestinal system of claim 1, wherein the plurality of the at least one type of commensal microbe embedded in the stimulus-responsive degradable material includes at least part of a gut microbiota embedded in the stimulus-responsive degradable material.

17. The gastrointestinal system of claim 16, wherein the at least part of the gut microbiota embedded in the stimulus-responsive degradable material includes at least one of a healthy gut microbiota, a preferred gut microbiota, or a theoretical gut microbiota embedded in the stimulus-responsive degradable material.

18. The gastrointestinal system of claim 1, wherein the plurality of the at least one type of commensal microbe includes at least one first type of commensal microbe embedded in the stimulus-responsive degradable material on at least one first portion of the flexible tubular structure of the adjunct device and at least one second type of commensal microbe embedded in the stimulus-responsive degradable material on at least one second portion of the flexible tubular structure of the adjunct device.

19. The gastrointestinal system of claim 1, further comprising a plurality of at least one first type of commensal microbe embedded in a first stimulus-responsive degradable material responsive to a first ingested chemical carried in the chyme and a plurality of at least one second type of commensal microbe embedded in a second stimulus-responsive degradable material responsive to a second ingested chemical carried in the chyme.

20. The gastrointestinal system of claim 1, wherein the plurality of the at least one type of commensal microbe embedded in the stimulus-responsive degradable material forms a gradient of microbes on the at least one of the inner surface and the outer surface of the flexible tubular structure of the adjunct device, wherein the gradient of microbes on the at least one of the inner surface and the outer surface of the flexible tubular structure of the adjunct device is identical to at least a portion of an endogenous gradient of microbes associated with the portion of the gastrointestinal tract of the individual for which the gastrointestinal sleeve is sized.

21. The gastrointestinal system of claim 1, wherein the stimulus-responsive degradable material includes a hydrogel responsive to the ingested chemical carried in the chyme.

22. The gastrointestinal system of claim 1, wherein the stimulus-responsive degradable material is responsive to ingested glucose carried in the chyme.

23. The gastrointestinal system of claim 1, wherein the stimulus-responsive degradable material is responsive to an ingested protein carried in the chyme.

24. The gastrointestinal system of claim 1, wherein the stimulus-responsive degradable material is responsive to an ingested antibody carried in the chyme.

25. The gastrointestinal system of claim 1, wherein the stimulus-responsive degradable material is responsive to an ingested aptamer carried in the chyme.

26. The gastrointestinal system of claim 1, further comprising at least one therapeutic agent in a degradable coating associated with at least one of the inner surface and the outer surface of the flexible tubular structure of the adjunct device.

27. The gastrointestinal system of claim 1, further comprising at least one bioactive agent in a degradable coating associated with at least one of the inner surface and the outer surface of the flexible tubular structure of the adjunct device.

28. The gastrointestinal system of claim 1, wherein the adjunct device includes at least one hook, barb, snap, pin, clip, staple, or prong configured to anchor the adjunct device to the inner surface or the outer surface of the gastrointestinal sleeve.

29. The gastrointestinal system of claim 1, wherein the adjunct device includes an expandable anchor structure configured to anchor the adjunct device to the inner surface or the outer surface of the gastrointestinal sleeve.

30. A gastrointestinal system, comprising:
a gastrointestinal device sized for placement in a portion of the gastrointestinal tract of a subject; and
an adjunct device comprising a patch, sheet, or tube sized to attach to an inner surface or an outer surface of the gastrointestinal device, the adjunct device including
a substrate having
an inner surface and an outer surface;
a stimulus-responsive degradable material associated with at least one of the inner surface and the outer surface of the substrate of the adjunct device, the stimulus-responsive degradable material responsive to an ingested chemical carried in chyme; and
a plurality of at least one type of commensal microbe embedded in the stimulus-responsive degradable material associated with the at least one of the inner surface or the outer surface of the substrate of the adjunct device, wherein the at least one type of commensal microbe is releasable from the stimulus-responsive degradable material in response to the ingested chemical carried in the chyme; and
at least one anchor structure connected to the substrate of the adjunct device and configured to attach the adjunct device to the inner surface or the outer surface of the gastrointestinal device; wherein the at least one anchor structure includes an adhesive on the inner surface or the outer surface of the adjunct device configured to anchor the adjunct device to the inner surface or the outer surface of the gastrointestinal device.

31. The gastrointestinal system of claim 30, wherein the gastrointestinal device is a gastrointestinal sleeve.

32. The gastrointestinal system of claim 30, wherein the gastrointestinal device is a stent.

33. The gastrointestinal system of claim 30, wherein the substrate of the adjunct device is a sheet of material sized to attach to the inner surface or the outer surface of the gastrointestinal device.

34. The gastrointestinal system of claim 30, wherein the substrate of the adjunct device is a tubular sheet of material sized to attach to the inner surface or the outer surface of the gastrointestinal device.

* * * * *